United States Patent
Trifiro et al.

(10) Patent No.: US 10,124,075 B2
(45) Date of Patent: Nov. 13, 2018

(54) BIONANOFLUID FOR USE AS A CONTRAST, IMAGING, DISINFECTING AND/OR THERAPEUTIC AGENT

(71) Applicant: THE ROYAL INSTITUTION FOR THE ADVANCEMENT OF LEARNING / MC GILL UNIVERSITY, Montréal (CA)

(72) Inventors: Mark Trifiro, Montréal (CA); Miltiadis Paliouras, Laval (CA); Philip Roche, Mont-Royal (CA); Idit Dotan, Toronto (CA); Lenore Beitel, Montéal (CA); Carlos Alvarado, Dollard-des-Ormeaux (CA); Matthew Carnevale, Montréal (CA); Elliot Jonathan Mitmaker, Montréal (CA)

(73) Assignee: THE ROYAL INSTITUTION FOR THE ADVANCEMENT OF LEARNING/MC GILL UNIVERSITY, Montreal, Quebec (CA)

( * ) Notice: Subject to any disclaimer, the term of this patent is extended or adjusted under 35 U.S.C. 154(b) by 0 days.

(21) Appl. No.: 15/036,707

(22) PCT Filed: Nov. 14, 2014

(86) PCT No.: PCT/CA2014/051094
§ 371 (c)(1),
(2) Date: May 13, 2016

(87) PCT Pub. No.: WO2015/070351
PCT Pub. Date: May 21, 2015

(65) Prior Publication Data
US 2016/0296640 A1 Oct. 13, 2016

Related U.S. Application Data

(60) Provisional application No. 61/904,264, filed on Nov. 14, 2013.

(51) Int. Cl.
| | | |
|---|---|---|
| A61K 9/00 | (2006.01) |
| A61K 49/00 | (2006.01) |
| C08J 3/075 | (2006.01) |
| A01N 59/00 | (2006.01) |
| A61K 33/44 | (2006.01) |
| A61K 41/00 | (2006.01) |
| A61L 2/18 | (2006.01) |
| A61K 49/18 | (2006.01) |
| A61K 49/22 | (2006.01) |
| A61K 47/68 | (2017.01) |
| A61K 47/69 | (2017.01) |
| B82Y 5/00 | (2011.01) |
| B82Y 15/00 | (2011.01) |

(52) U.S. Cl.
CPC .......... *A61K 49/0095* (2013.01); *A01N 59/00* (2013.01); *A61K 33/44* (2013.01); *A61K 41/0028* (2013.01); *A61K 47/6851* (2017.08); *A61K 47/6903* (2017.08); *A61K 47/6905* (2017.08); *A61K 49/0093* (2013.01); *A61K 49/1803* (2013.01); *A61K 49/1806* (2013.01); *A61K 49/226* (2013.01); *A61L 2/18* (2013.01); *C08J 3/075* (2013.01); *B82Y 5/00* (2013.01); *B82Y 15/00* (2013.01); *C08J 2389/00* (2013.01)

(58) Field of Classification Search
None
See application file for complete search history.

(56) References Cited

U.S. PATENT DOCUMENTS

| | | |
|---|---|---|
| 7,169,329 B2 | 1/2007 | Wong et al. |
| 7,981,362 B2 | 7/2011 | Glezer et al. |
| 8,313,773 B2 | 11/2012 | Kim et al. |
| 9,023,250 B2 | 5/2015 | Li et al. |
| 9,149,833 B2 | 10/2015 | Ramaprabhu et al. |

(Continued)

FOREIGN PATENT DOCUMENTS

| | | |
|---|---|---|
| CA | 2708319 | 2/2009 |
| WO | 2008/154043 A2 | 12/2008 |
| WO | 2010111741 | 10/2010 |

OTHER PUBLICATIONS

Liu et al., "Direct synthesis of carbon nanotubes decorated with size-controllable Fe nanoparticles encapsulated by graphitic layers", Carbon, vol. 46, p. 1417-1423, 2008.
Munkhbayar et al., "Surfactant-free dispersion of silver nanoparticles into MWCNT-aqueous nanofluids prepared by one-step technique and their thermal characteristics", Ceramics International, vol. 39, p. 6415-6425, 2013.
Chen et al., "Enhanced thermal conductivity of nanofluids containing Ag/MWNT composites", Powder Technology, vol. 231, p. 18-20, 2012.
Jha et al., "Synthesis and thermal conductivity of copper nanoparticle decorated multiwalled carbon nanotubes based nanofluids", The Journal of Physical Chermistry C, Vo. 112, p. 9315-9319, 2008.

(Continued)

*Primary Examiner* — James W Rogers
(74) *Attorney, Agent, or Firm* — Merchant & Gould P.C.

(57) ABSTRACT

A bionanofluid includes a carbon-based nanomaterial substantially mono-dispersed in a fluid. The carbon-based nanomaterial is surface modified with a polar group when the fluid is polar or with a non-polar group when the fluid is non-polar, and functionalized with a biological targeting moiety to allow specific association of the carbon-based nanomaterial to a targeted entity. A hybrid bionanofluid includes the bionanofluid, with the carbon-based nanomaterial further modified with a hybrid nanoparticle which includes an alloy, transition metal, semi-conductor, semi-metal or polymer based nanoparticle with biological targeting moiety. A hydrogel, foam, cream, spray or dried product includes the bionanofluid or hybrid bionanofluid. The bionanofluid or hybrid bionanofluid are useful in multimodal imaging (photo-luminescence, luminescence, photo-acoustic, MRI, ultrasound) and/or cellular targeting.

18 Claims, 60 Drawing Sheets

(56) References Cited

U.S. PATENT DOCUMENTS

| | | |
|---|---|---|
| 2007/0280876 A1 | 12/2007 | Tour et al. |
| 2011/0171137 A1 | 7/2011 | Patolsky et al. |
| 2011/0253945 A1 | 10/2011 | Tohji et al. |
| 2012/0183770 A1 | 7/2012 | Bosnyak et al. |
| 2012/0186789 A1 | 7/2012 | Sedarous et al. |
| 2012/0235080 A1 | 9/2012 | Hong et al. |
| 2015/0359886 A1* | 12/2015 | Wu .................. A61K 9/06 604/500 |
| 2016/0296640 A1 | 10/2016 | Trifiro et al. |
| 2016/0376486 A1 | 12/2016 | Atieh et al. |

OTHER PUBLICATIONS

Amiri et al., "Highly dispersed multiwalled carbon nanotubes decorated with Ag nanoparticles in water and experimental investigation of the thermophysical properties", The Journal of Physical Chemistry C., vol. 116, p. 3369-3375, 2012.

Vandsburger et al., "Stabilized aqueous dispersion of multi-walled carbon nanotubes obtained by RF glow-discharge treatment", J. Nanopart. Res., vol. 11, p. 1817-1822, 2009.

Hordy et al., "Plasma functionalization of carbon nanotubes for the systhesis of stable aqueous nanofluids and Poly (vinyl alcohol) nanocomposites", Plasma Process. Polym., vol. 10, p. 110-118, 2013.

Wong et al., "Applications of nanofluids: Current and future, Advances in Mechanical Engineering", vol. 2010, Article ID 519659, p. 1-11.

Sreeja et al., "Linear and nonlinear optical properties of multi walled carbon nanotubes with attached gold nanoparticles", J. Electrochem. Soc., vol. 158, No. 10, p. K187-K191, 2011.

Henley et al., "Laser-induced decoration of carbon naotubes with metal nanoparticles", Applied Physics A, vol. 93, Issue 4, p. 875-879, 2008.

Jha et al., "Thermal conductivity studies of metal dispersed multiwalled carbon nanotubes in water and ethylene glycol based nanofluids", J. Appl. Phys., vol. 106, p. 084317-1 to 084317-6, 2009.

Kaniyoor et al., "Gold nanoparticles decorated multi-walled carbon nanotubes as counter electrode for dye sensitized solar cells", Journal of Nanoscience and Nanotechnology, vol. 12, No. 11, p. 8323-8329, 2012.

Marches et al., "The importance of cellular internalization of antibody-targeted carbon nanotubes in the photothermal ablation of breast cancer", Nanotechnology, vol. 22, Article 095101, 2011.

Nima et al., "Single-walled carbon nanotubes as specific targeting and Raman spectroscopic agents for the detection and discrimination of single human breast cancer cells", Journal of Biomedical Optics, 18/5, Article 055003, 2013.

Yin et al., "Water-dispersible multiwalled carbon nanotube/iron oxide hybrids as contract agents for cellular magnetic resonance imaging", Carbon, vol. 50, p. 2162-2170, 2012.

Du et al., "Sensitive immunosensor for cancer biomarker based on dual signal amplification strategy of graphene sheets and multi-enzyme functionalized carbon nanospheres" Anal. Chem., vol. 83(7), p. 2989-2995, 2010.

Dhar et al., "Targeted single wall carbon nanotube mediated Pt(IV) prodrug delivery using folate as a homing device" J. Am. Chem. Soc., vol. 130(34), p. 11467-11476, 2008.

Chakravarty et al., "Thermal ablation of tumor cells with antibody-functionalized single-walled carbon nanotubes", Proc. Nat. Acad. Sci. USA, vol. 105(25), p. 8697-9702, 2008.

Baac et al., "Carbon nanotube composite optoacoustic transmitters for strong and high frequency ultrasound generation", Appl. Phys. Lett. 97, p. 234104-1 to 234104-3, 2010.

Delogu et al., "Functionalized multiwalled carbon nanotubes as ultrasound contrast agents", PNAS, vol. 109 No. 41, p. 16612-16617, 2012.

Singh et al., "Tissue biodistribution and blood clearance rates of intravenously administered carbon nanotube radiotracers", PNAS, vol. 103 No. 9, p. 3357-3362, 2006.

Wei et al., "Biodistribution of co-exposure to multi-walled carbon nanotubes and nanodiamonds in mice", Nanoscale Research Letters, 7:473, p. 1-9, 2012.

Extended European Search Report for corresponding European Patent Application No. 14862662.5 dated Apr. 20, 2017, 13 pages.

Kim, S.W. et al., "Surface modifications for the effective dispersion of carbon nanotubes in solvents and polymers", Carbon, 50(1): 3-33 (2011).

Rosca, I.D. et al., "Doubly functionalized multiwall carbon nanotubes with enhanced solubility", Carbon, 47(10): 2552-2555 (2009).

Shi, J. et al., "PEGylated fullerene/iron oxide nanocomposites for photodynamic therapy, targeted drug delivery and MR imaging", Biomaterials, 34(37): 9666-9677 (2013).

Wang, B. et al., "A mitochondria-targeted fluorescent probe based on TPP-conjugated carbon dots for both one and two-photon fluorescence cell imaging", RSC Adv., 4(91): 49960-49963 (2014).

* cited by examiner

EDC - 1-Ethyl-3-(3-dimethylaminopropyl) carbodiimide
NHS - *N*-Hydroxysuccinimide Possible ligands:
Antibody
Peptide
Small molecule
Aptamer α-PSMA-Mag-CNT on LNCaP cells α-PSMA-Mag-CNT - laser treated among debris of LNCaP cells α-PSMA-Mag-CNT capture of cluster of LNCaP cells α-TSHR-Mag-CNT capture of cluster of BCPAP cells Bionanofluid concentration (1g/L)

Air in glass tube

Thiol-PEG-CNT Bionanofluid in tube

With modified nanofluid present in all 3 tubes

Modified nanofluid missing from tube 2

BIONANOFLUID FOR USE AS A CONTRAST, IMAGING, DISINFECTING AND/OR THERAPEUTIC AGENT

This application is a National Stage Application of PCT/CA2014/051094, filed 14 Nov. 2014, which claims benefit of U.S. Provisional Ser. No. 61/904,264, filed 14 Nov. 2013, and which applications are incorporated herein by reference. To the extent appropriate, a claim of priority is made to each of the above disclosed applications.

FIELD OF THE INVENTION

The present invention relates to the field of nanotechnology and more particularly concerns a bionanofluid comprising a mono-dispersed carbon-based nanomaterial as a contrast, imaging, disinfecting and/or therapeutic agent.

BACKGROUND

Over the past few years, there has been tremendous interest in exploiting nanotechnology materials and devices in the diagnostic and/or treatment of biological problems or diseases, including the treatment of infections and/or human cellular diseases. However, so far the interactions between carbon nanomaterials and cellular physiology have been characterized as an issue of biochemical mechanisms involving molecular transport, cellular adhesion, etc.

Ultrasound imaging is a widely applied technique in clinical research and treatment, where sound waves are projected towards an object and the reflected waves are analysed. Ultrasound imaging, however, has some major drawbacks. Achieving high axial and spatial resolution comes at the price of penetration depth. Frequencies of 30 to 55 MHz are typically used, providing an image which is highly resolved, but shallow. For deep structures, lower frequencies in the range of 1-18 MHz are applied, enabling a greater penetration depth, but with a limited image resolution in either axis. Several strategies have been developed to resolve this issue, such as image reconstruction techniques to lower background noise, the creation of synthetic apertures, and, finally, by contrast-enhanced ultrasound approaches.

Contrast-enhanced ultrasound (CEUS) is a technique where contrast agents having ligands allowing them to bind to the cells of interest are injected in the patient. The technique is however limited to entities that can cause an intense reflection or generate significant echogenicity, i.e., the ability to reflect sound waves. Currently, the major and only commercial contrast agents are microbubbles, which are filled with a gas, usually using perfluorcarbons. The microbubbles oscillate in the presence of the ultrasonic field, generating the backscatter that can be detected with a strong contrast to surrounding tissues. One drawback of microbubbles is the use of perfluorocarbons, which last but a few short minutes in the blood and are highly expensive, prohibiting their widespread use. The presence of microbubbles is also detrimental to patient health, resulting in head pains, nausea and other side effects of use in a significant number of patients, which provides an incentive to avoid their use from a clinical prospective.

Nanofluids comprising nanoparticles dispersed in a fluid where the physical material is defined as nano and is dispersed. Nanoparticles such as carbon nanotubes (CNT), carbon nanoparticles and hybrid particle systems can be modified by physical or chemical processes to enhance their dispersibility in the fluid. However, these nanofluids are not suitable to enable or elicit bio-specific biological responses. Nanofluids that are not biomodified, are not able of delivering specific targeted effects. Bionanofluid definitions require the inclusion of bio-related or bio-molecular functionalization that is specific to a desired application.

SUMMARY

Bionanofluids can be developed from carbon-based nanomaterials by addition to the nanomaterials surface of bio-affinity agents or biological molecules, these bio-affinity agents or biological molecules are also referred to as targeting moieties. By the addition of biological molecules and/or other biologic modifications, the materials' properties are harnessed and improved. These bionanofluids can deliver a platform for imaging and/or therapeutic action.

Formulations of bionanofluids can be prepared for specific applications and each formulation is a new product designed for a specific function. The range of applications for the bionanofluids is broad as the applications for targeted cell death can encompass fields such as cancer treatment and/or infection control.

The bio-modification of the nanomaterial allows preventing non-specific association with non-targeted entities. In one embodiment, the specific cell targeting that can be achieved with the bionanofluid, combined with the bionanofluid's photonic properties allows enhancing cellular function disruption to the point where cell viability is impossible. Thanks to the combination of its targeting and photonic properties, the bionanofluid can thus be used as a therapeutic agent and/or disinfecting agent. But, the combination of the targeting and photonic properties also allows using the bionanofluid in other applications which do not necessarily involve cell disruption, such as an imaging agent or as a contrast agent for ultrasound.

In one aspect, there is provided a bionanofluid comprising a carbon-based nanomaterial substantially mono-dispersed in a fluid, wherein the carbon-based nanomaterial is surface modified with polar groups when the fluid is polar or with non-polar groups when the fluid is non-polar, and functionalized with targeting moieties to allow specific association of the carbon-based nanomaterial to targeted entities.

In one embodiment, there is provided a bionanofluid comprising a carbon-based nanomaterial substantially mono-dispersed in a fluid, wherein the carbon-based nanomaterial is surface modified with a polar group when the fluid is polar or with a non-polar group when the fluid is non-polar, and functionalized with a targeting moiety to allow specific association of the carbon-based nanomaterial to a targeted entity.

In one embodiment, there is provided a hybrid bionanofluid comprising the bionanofluid described therein, wherein the carbon-based nanomaterial is further modified with a hybrid nanoparticle which comprises an alloy, transition metal, semi-conductor, semi-metal, polymer based nanoparticle or a combination thereof.

In one embodiment, there is provided a hydrogel comprising the bionanofluid described therein or the hybrid bionanofluid described therein, and gelatin.

In one embodiment, there is provided a foam comprising the bionanofluid described therein or the hybrid bionanofluid described therein, and silica or a derivative thereof.

In one embodiment, there is provided a cream or a spray comprising the bionanofluid described therein or the hybrid bionanofluid described therein.

In one embodiment, there is provided a dried product obtained by drying the bionanofluid described therein or the hybrid bionanofluid described therein.

In one embodiment, there is provided a use of the bionanofluid described therein or the hybrid bionanofluid described therein to create disruption of the targeted entity upon application of an external energy including light, ultrasound or radiowaves, when the targeting moiety is associated with the targeted entity, preferably a prokaryote or an eukaryote, more preferably a cell, virus, bacteria, spore, a fungus or a small multi-cellular organism such as a microscopic worm.

In one embodiment, there is provided a use of the bionanofluid described therein or the hybrid bionanofluid described therein as an antiseptic agent, wherein the targeted entity is an infectious agent, preferably a prokaryote or an eukaryote, preferably a cell, bacteria, spore, virus, prion, fungus, or a small multi-cellular organism such as a worm.

In one embodiment, there is provided a use of the bionanofluid described therein or the hybrid bionanofluid described therein as a contrast agent for ultrasound, preferably ultrasound imaging.

In one embodiment, there is provided a use of the bionanofluid described therein or the hybrid bionanofluid described therein as an imaging agent.

Other features as aspects of the invention will be better understood upon reading of preferred embodiments thereof with reference to the appended figures.

BRIEF DESCRIPTION OF THE DRAWINGS

FIG. 1. Coupling chemistry used with Thiol-PEG-CNTs to attach bio-affinity molecules. PEGylation of the Thiol-CNT particles is described in PEG treatment.

FIG. 2. Coupling chemistry used with Mal-PEG-CNTs to attach bio-affinity molecules. Initially EDC/NHS chemistry is used to link maleimide-PEG-amide to COOH-functionalized bionanofluid in Reaction 1. Reaction 2 allows for the coupling of bio-affinity molecule to maleimide component of PEG.

FIG. 3. Total antibody load using an amine-Mal-PEG-Cysteine coupling to carbon-derived bionanofluid, creating antibody labeled chemi-luminescent applications. Horseradish peroxidase (HRP)-Ab conjugates prepared as for conventional antibody linkage. Conjugates were washed three times to exclude non-specific carry-over of residual non-covalently linked HRP-Ab. None was detected in C-PEG control. Total loading of Ab via thioester coupling assessed by presence of reporter HRP-Ab on surface. Possible pre-concentration of HRP-Ab via covalent linkage as serial dilutions generate lower signal at 1/500 μl (v/v) dilution than 0.5 μl Ab conjugate.

FIG. 4. Image of Bacterial streak on Agar plate obliterated by use of Carbon-derived BioNanofluid Hydrogel and laser cell killing. Region of bacterial killing indicated by black box.

FIG. 5. Crystalline purified Carbon Dots (quantity 1 gram) produced from green materials. Material is ready for re-suspension in water and immediately mono-disperse.

FIG. 6. Photoluminescence of Carbon Dots under UV light illumination. A. BSA-Carbon-Dots against water B. Comparison of BSA-Carbon-Dots, Glucose-Carbon-Dots and PEG-Carbon-dots against water, under UV illumination. 1 ml of dots on in the left hand tube and compared to water. Concentration is 0.5 mg/ml.

FIG. 7. Comparison of magnetized-α-TSHR-Thiol-PEG-CNT (left) vs. non-magnetized-α-TSHR-Thiol-PEG-CNTs CNT (right) particles on a magnetic separator.

FIG. 8. α-TSHR-Magnetized-CNT on BCPAP cells exposed to magnetized field. Arrows indicate stationary cells, and yellow boxes indicate movement of cells attached with α-TSHR-magnetized-CNTs over a period of time. A. 3 seconds, B. 15 seconds, and C. 20 seconds.

FIG. 9. Antibody-Magnetized-CNT on LNCaP and BCPAP cells. A. A single LNCaP cell before and after exposure to laser, targeted with magnetized-α-PSMA-Thiol-PEG-CNTs. B. LNCaP and BCPAP cells prior to laser exposure to illustrate the adherence of antibody-magnetized-CNTs on the cells.

FIG. 10. Carbon-derived bionanofluid: Gelatin hydogel (heating at different laser powers. At laser powers >1 W, the observation that the hydrogel becomes liquefied.

FIG. 11. Carbon-derived bionanofluid: Gelatin hydrogel heating increasing BioNanofluid concentration (1 g/L) leads to rapid heating, laser 2 W.

FIG. 12. Carbon-derived bionanofluid foam at different magnifications. A. Spot of bionanofluid foam, with size marker. B. 5× magnification, C. 10× magnification, D. 20× magnification.

FIG. 13. Scanning Electron Microscopy (SEM) images of carbon-derived bionanofluids. A. COOH-functionalized Bionanofluid. B/C. Gold loaded MWCNT, gold particles having defined spherical structure, at two different magnifications.

FIG. 14. Carbon Dots on STEM mesh substrate. Size varies from 100 nm to 5 nm and below. A. PEG-Dots. B. BSA-Dots.

FIG. 15. UV/VIS of Size controlled carbon nanotubes derived bionanofluid. All particles are below 220 nm length, 50 nm diameter.

FIG. 16. Evidence on resonant Au Particles bound to Carbon nanotubes.

FIG. 17. COOH-CNT bionanofluid, size range 0.001-2 μm.

FIG. 18. UV/Vis spectra of Carbon Dots, A. PEG-Carbon dots, B. Glucose-Carbon dots and C. BSA-Carbon dots.

FIG. 19. Carbon Dot Near Infra Red Photo-luminescence.

FIG. 20. Demonstration of the effectiveness of PEG-Thiol-CNT Bionanofluid as an ultrasound contrast agent. A. without and, B. with bionanofluid.

FIG. 21. Thiol-PEG-CNT Bionanofluid encased in an agarose gel. Image of bionanofluid taken above the plane of ultrasound probe set to 30 mHz. The reflection is caused by the interaction with the bionanofluid above the plane of the gel can be noted.

FIG. 22. Thiol-PEG-CNT Bionanofluid end oriented longitudinally to the probe face, covered with gel and brought into contact with the probe face. A. The interaction at the bottom of the tube waves was analyzed. B. Same experiment with tube 2, left blank and lacking modified bionanofluid.

FIG. 23. Potential to agitate/manipulate the PEG-Thiol-CNT bionanofluid by non-contact movement of ultrasound probe at a distance of 2-5 cm.

FIG. 24. Ultrasound contrast of Thiol-PEG-CNT Bionanofluid in the Vena Cava of a mouse. Arrows indicate contrast image of the bionanofluid, over a time course. A. saline injection, B. Bionanofluid injection time point t=1 minute, C. Bionanofluid injection time point t=10 minutes.

FIG. 25. Ultrasound contrast of Thiol-PEG-CNT Bionanofluid in the Aortic Arch of a mouse. Arrows indicate contrast image of the bionanofluid, over a time course. A.

saline injection, B. Bionanofluid injection time point t=1 minute, C. Bionanofluid injection time point t=2 minutes.

FIG. 26. Ultrasound contrast of Thiol-PEG-CNT Bionanofluid in the bladder of a mouse. Box shows a magnified area of the urethra and arrows indicate contrast image of the bionanofluid of the expulsion of the bionanofluid over a period of time. Images represent frame capture of 200 frames total (time course), post bionanofluid injection. A. Frame 7/200, B. Frame 69/200, C. Frame 85/200, and D. Frame 151/200

Figure 27A:
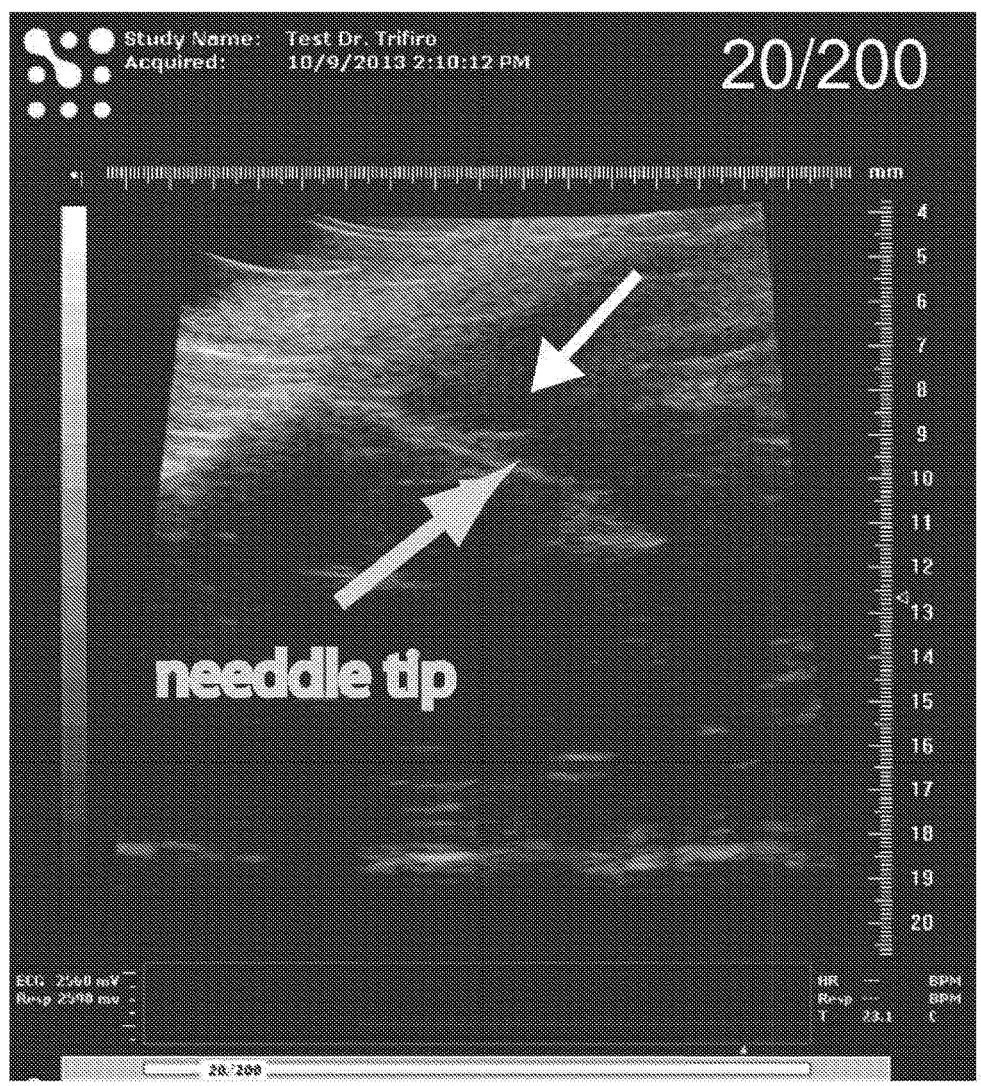
Figure 27B:
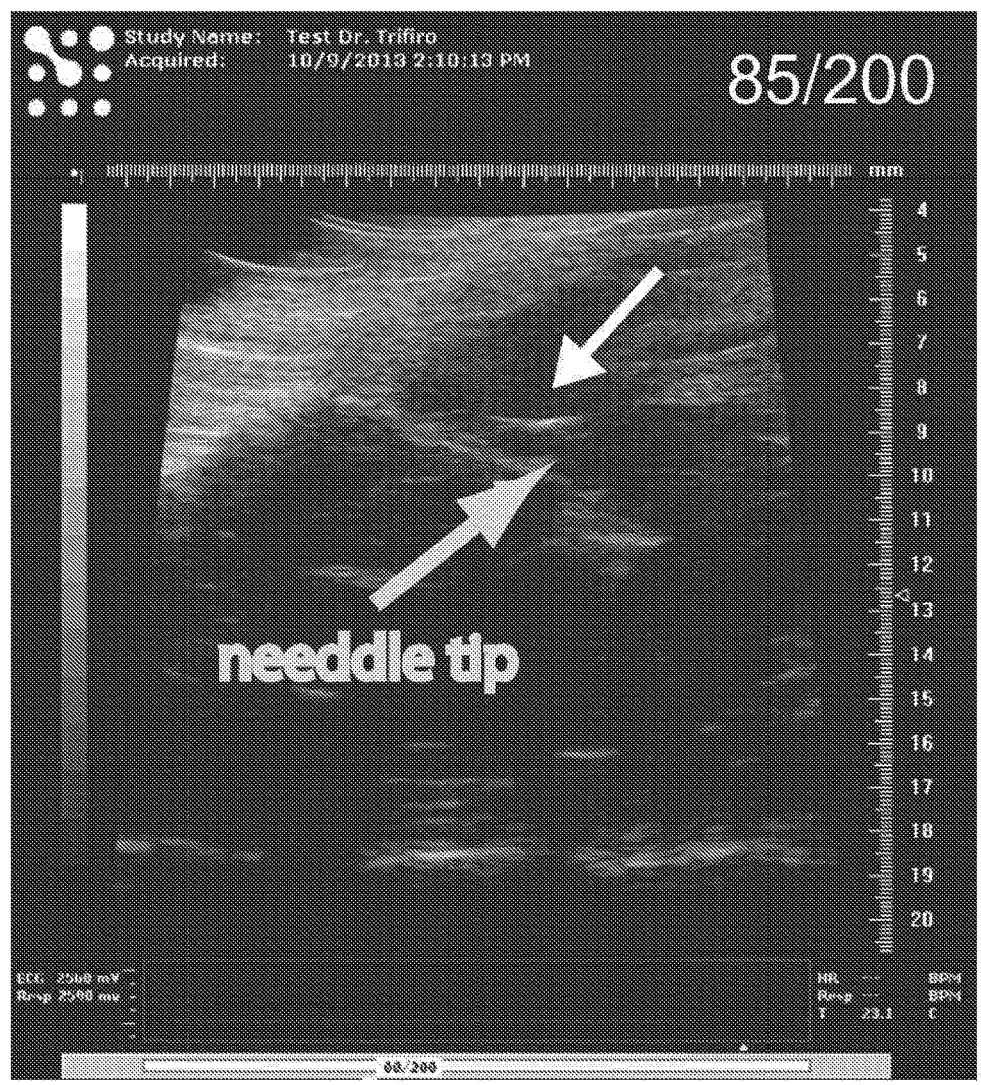
Figure 27C:
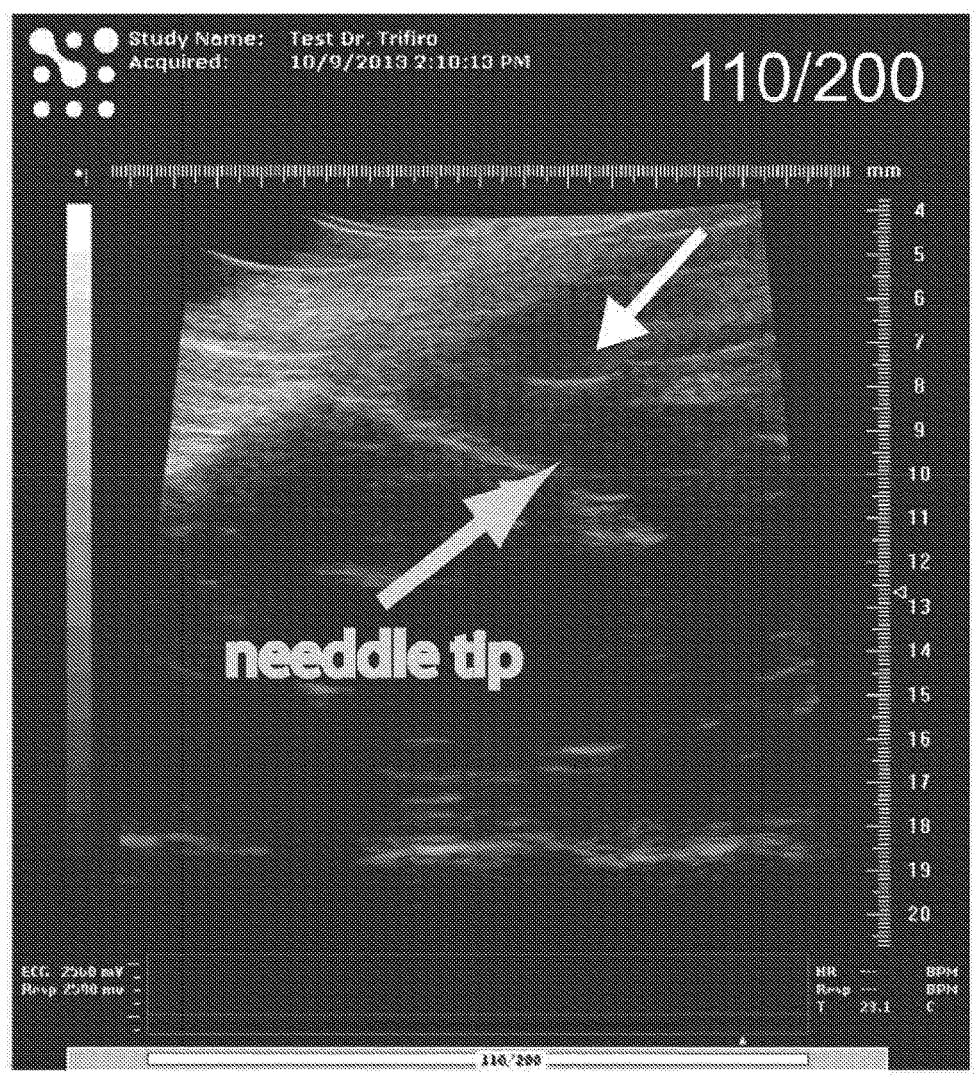

FIG. 27. Ultrasound contrast of Thiol-PEG-CNT Bionanofluid in the kidney of a mouse. White Arrows indicate the bionanofluid movement in the Kidney over a period of time. Yellow arrowheads indicate the needle tip. Images represent frame capture of 200 frames total (time course), post bionanofluid injection. A. Frame 20/200, B. Frame 85/200, and C. Frame 110/200

Figure 28A:
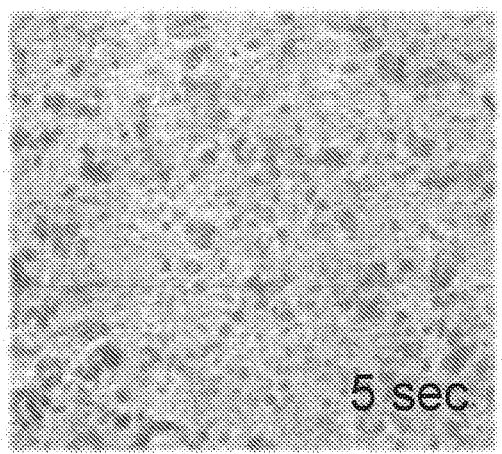
Figure 28B:
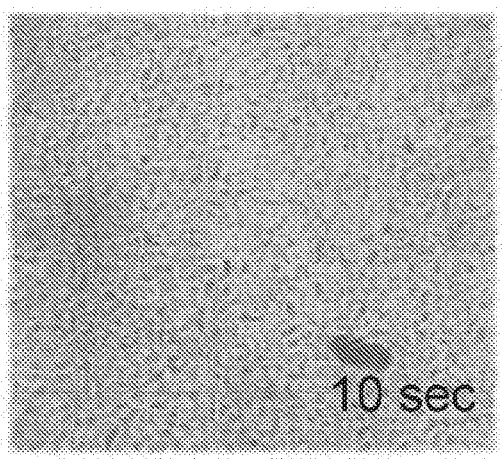
Figure 28C:
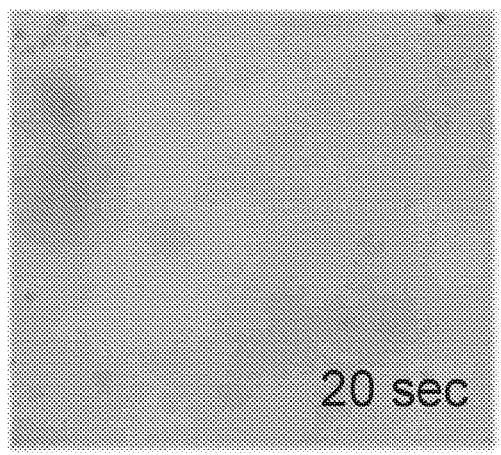

FIG. 28. HEK293 cells mixed with carbon-derived Thiol-PEG-CNT bionanofluid and exposed to laser for different periods of time, A. 5 seconds, B. 10 seconds and C. 20 seconds. After exposure cells were reseeded onto 6-well plates with DMEM+10% FBS growth media. Cells were allowed to grow for 5 days and a picture of the cells in the plate was taken. No live cells were present after 20 sec exposure.

Figure 29:
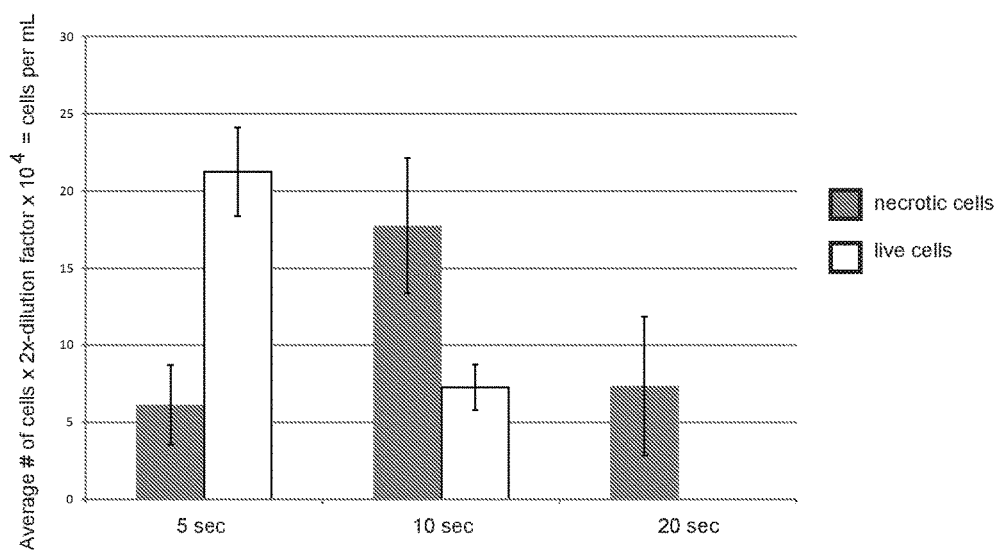

FIG. 29. HEK283 cells mixed with Thiol-PEG-CNT carbon-derived bionanofluid and exposed to laser for different periods of time (5, 10, 20 sec). After exposure cells were mixed with Trypan blue, and counted. Trypan Blue labels necrotic/blue (or dead) cells and live/white cells. Experiment performed n=4. Cells counted using a haemocytometer.

Figure 30:
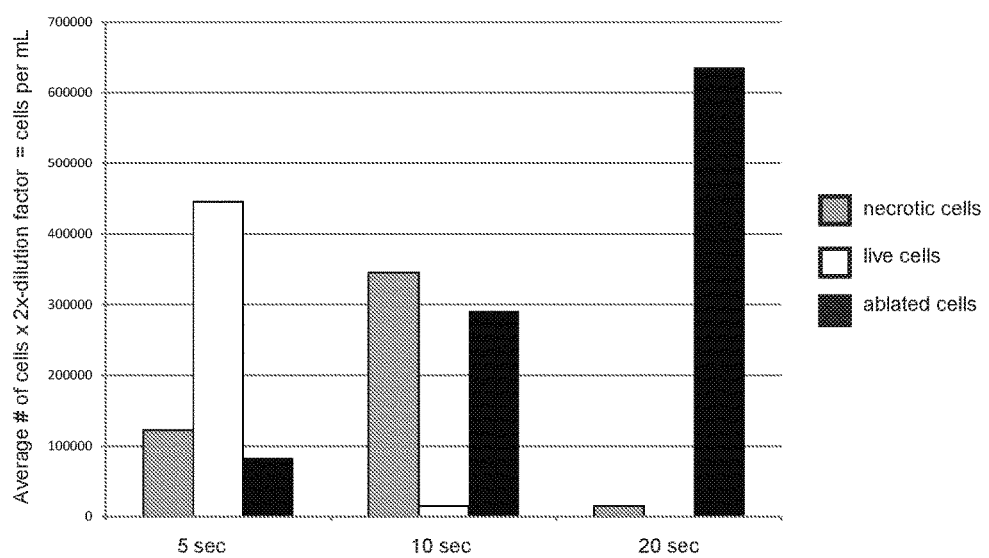

FIG. 30. 650,000 HEK283 cells mixed with Thiol-PEG-CNT carbon-derived bionanofluid and exposed to laser for different periods of time (5, 10, 20 sec). After exposure cells were mixed with Trypan blue, and counted. Trypan Blue labels necrotic/blue (or dead) cells blue and live/white cells. Ablated cell numbers were determined from a per-count of cells prior to exposure to the laser. As the amount of heat generated in the tube, is so high, cells "literally" explode. Experiment performed n=1. Cells counted using a haemocytometer.

Figure 31:
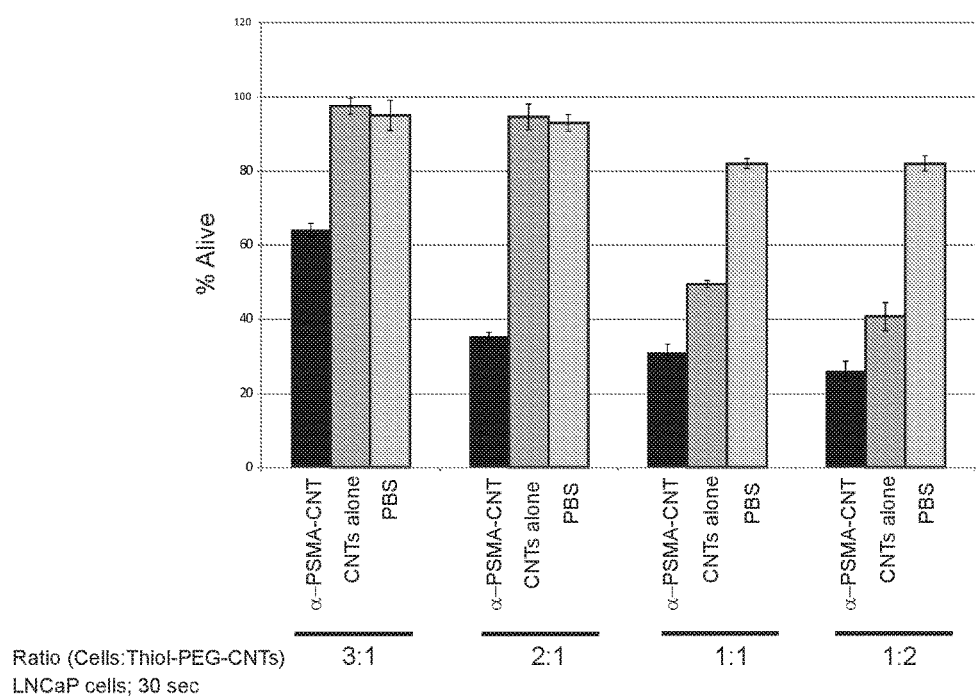

FIG. 31. Cell ablation studies using α-PSMA-Thiol-PEG-CNTs, to determine concentration of cells to CNT particle. Cells were mixed with α-PSMA-Thiol-PEG-CNT-bionanofluid at 37° C. for 1 hr, cells were washed 5× with PBS and re-suspended in PBS and exposed to 532 nm laser for 30 sec. An aliquot of cells were removed to give a pre-count of cells. After laser exposure, cells were mixed with Trypan blue, and white cells or live cells were counted. Results given as Alive and experiment performed n=6. 2:1 ratio cells to bionanofluid was determined optimal, as higher concentrations of bionanofluid results in bulk-heating. Cells counted using a haemocytometer.

Figure 32:
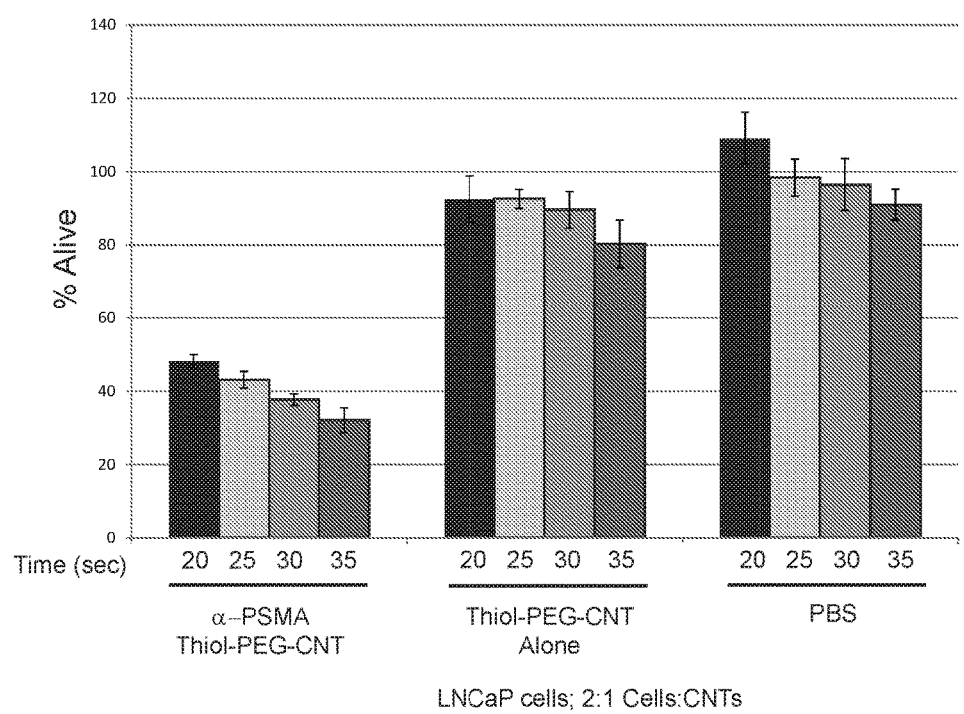

FIG. 32. Cell ablation studies using α-PSMA-Thiol-PEG-CNT, to exposure time of cells to laser. Cells were mixed with α-PSMA-Thiol-PEG-CNT-bionanofluid at 37° C. for 1 hr, cells were washed 5× with PBS and resuspended in PBS and exposed to 532 nm laser for 30 sec. An aliquot of cells were removed to give a pre-count of cells. After laser exposure (20, 25, 30, 35 sec) cells were mixed with Trypan blue, and white cells or live cells were counted. Results given as % Alive and experiment performed n=6. 30 sec exposure of the cells to the bionanofluid was determined optimal, as longer exposure results in bulk-heating. Cells counted using a haemocytometer.

Figure 33:
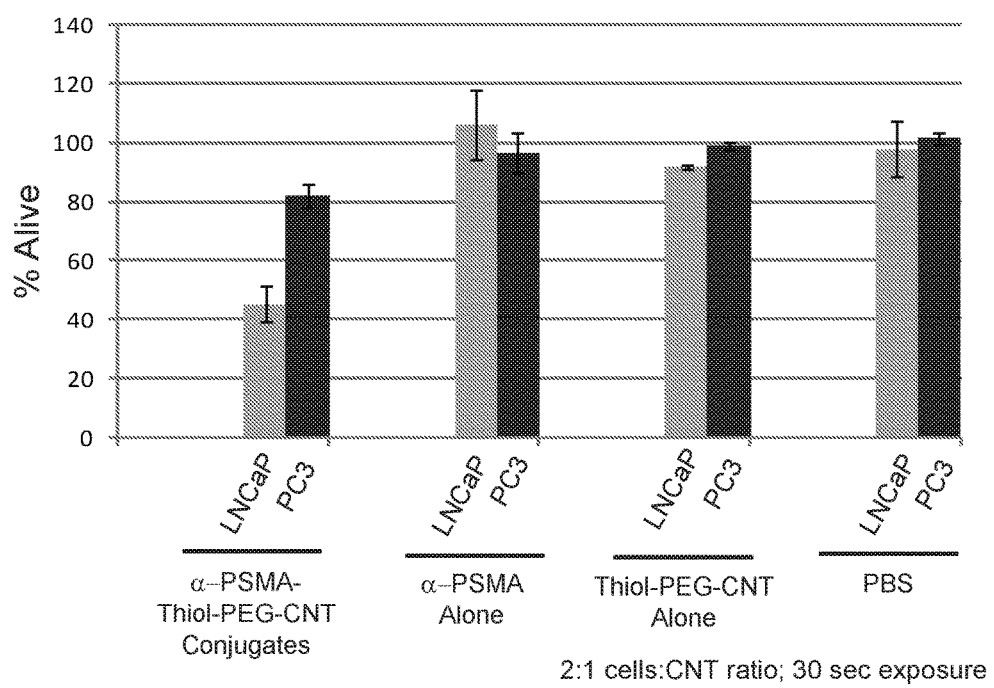

FIG. 33. Cell ablation studies using α-PSMA-Thiol-PEG-CNT, of PSMA positive LNCaP cells vs. PSMA negative-PC3 cells. Cells were mixed with α-PSMA-Thiol-PEG-CNT bionanofluid at 37° C. for 1 hr, cells were washed 5× with PBS and re-suspended in PBS and exposed to 532 nm laser for 30 sec. An aliquot of cells were removed to give a pre-count of cells. 2:1 cell:bionanofluid, and 30 sec exposure was used. Experiment was repeated n=4. Cells counted using a haemocytometer.

Figure 34:
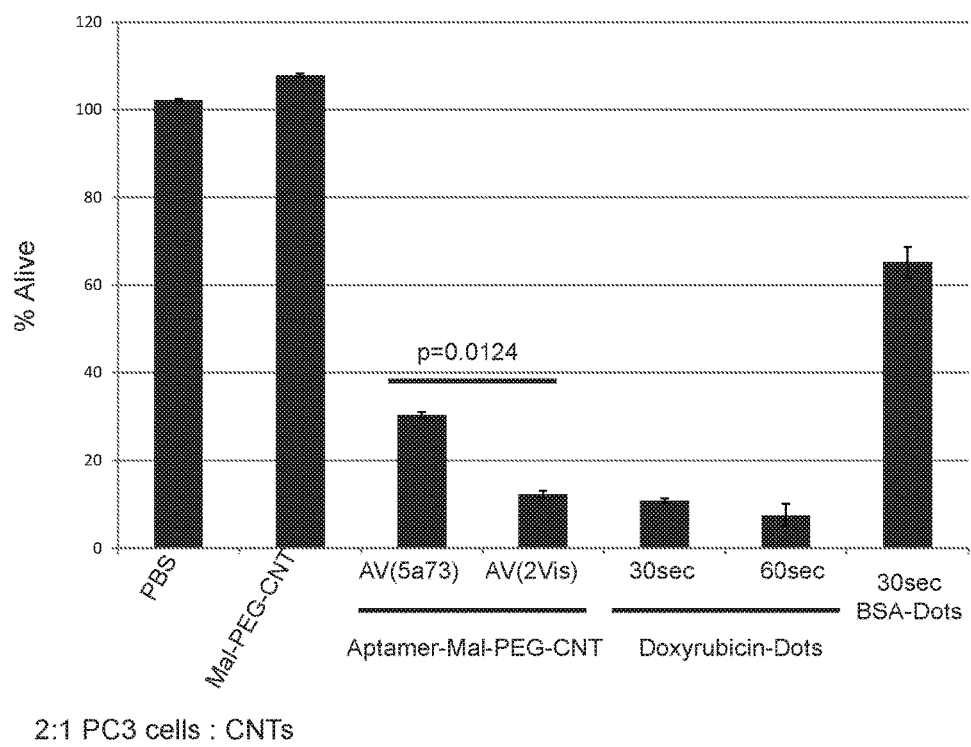

FIG. 34. Cell ablation studies using PC3 cells with SELEX isolated PC3-specific aptamer and Doxyrubicin-linked carbon dots. PC3 cells were mixed with respective bionanofluid or PBS/control at 37° C. for 1 hr, cells were washed 5× with PBS and resuspended in PBS and exposed to 532 nm laser for 30 sec. An aliquot of cells were removed to give a pre-count of cells. 2:1 cell:Mal-PEG-bionanofluid, and 30 sec exposure was used, unless noted otherwise. Experiment was repeated n=4. 5a73 is a known DNA aptamer for PC3 cells, whereas 2Vis is the SELEX-DNA aptamer isolated by the inventors, which show higher and more significant (p=0.0124) cell killing than the commercially available product. Carbon dots were also coupled to doxorubicin and exposed to cells. Observation of a synergistic cell ablation of doxorubicin-dots vs. BSA-dots. Cells counted using a haemocytometer.

Figure 35:
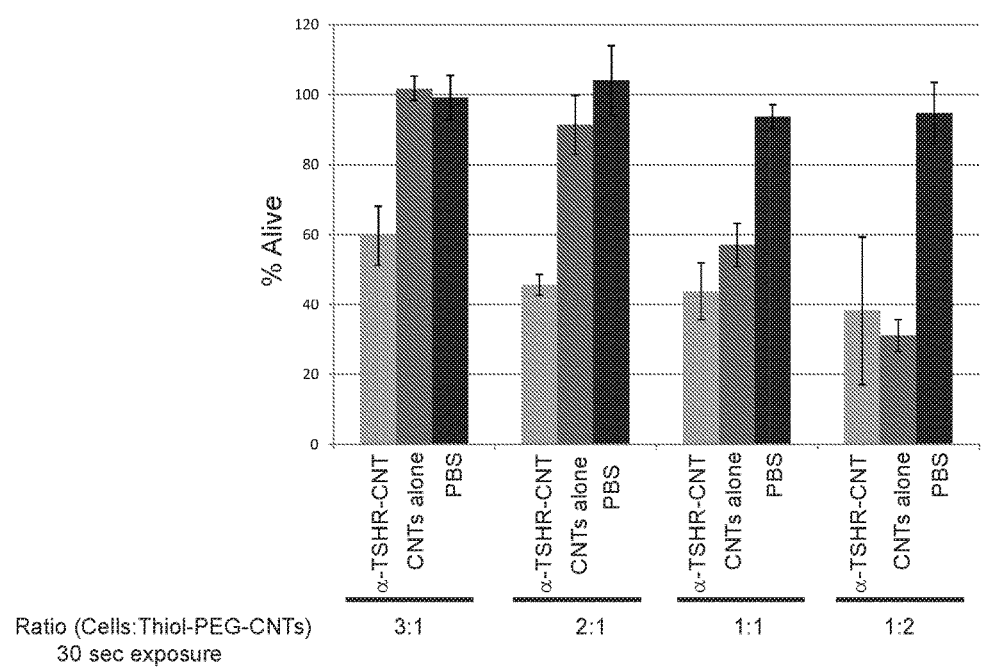

FIG. 35. Cell ablation studies using α-TSHR-Thiol-PEG-CNTs, to determine concentration of cells to CNT particle. Cells were mixed with α-TSHR-Thiol-PEG-CNT-bionanofluid at 37° C. for 1 hr, cells were washed 5× with PBS and re-suspended in PBS and exposed to 532 nm laser for 30 sec. An aliquot of cells were removed to give a pre-count of cells. After laser exposure, cells were mixed with Trypan blue, and white cells or live cells were counted. Results given as Alive and experiment performed n=6. 2:1 ratio cells to bionanofluid was determined optimal, as higher concentrations of bionanofluid results in bulk-heating. Cells counted using a haemocytometer.

Figure 36:
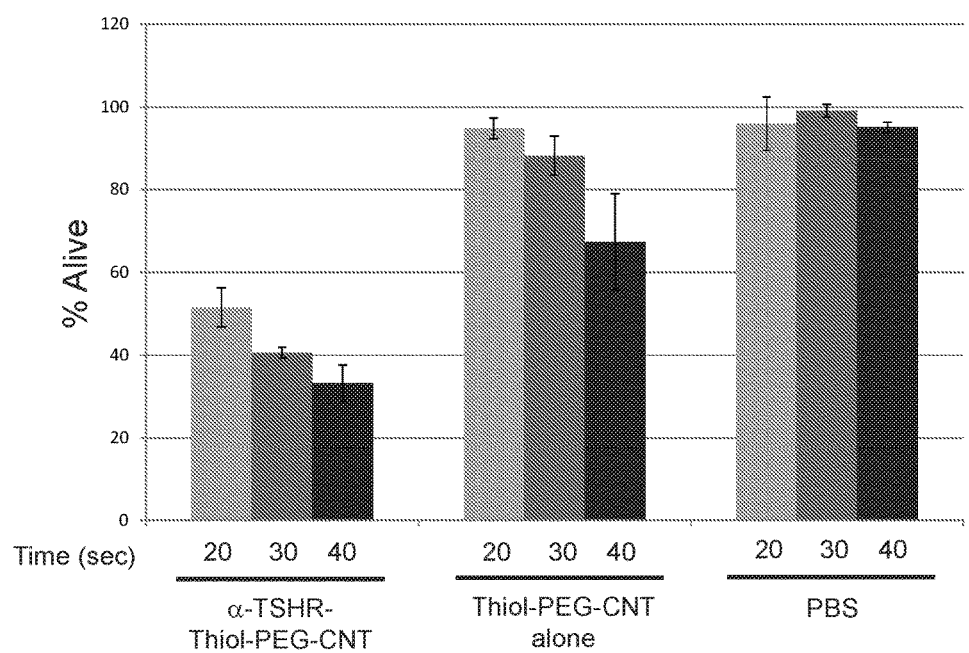

FIG. 36. Cell ablation studies using α-TSHR-Thiol-PEG-CNTs, to exposure time of cells to laser. Cells were mixed with α-TSHR-Thiol-PEG-CNT-bionanofluid at 37° C. for 1 hr, cells were washed 5× with PBS and re-suspended in PBS and exposed to 532 nm laser for 30 sec. An aliquot of cells were removed to give a pre-count of cells. After laser exposure (20, 30, 40 sec) cells were mixed with Trypan blue, and white cells or live cells were counted. Results given as % Alive and experiment performed n=6. 30 sec exposure of the cells to bionanofluid was determined optimal, as longer exposure results in bulk-heating. Cells counted using a haemocytometer.

Figure 37:
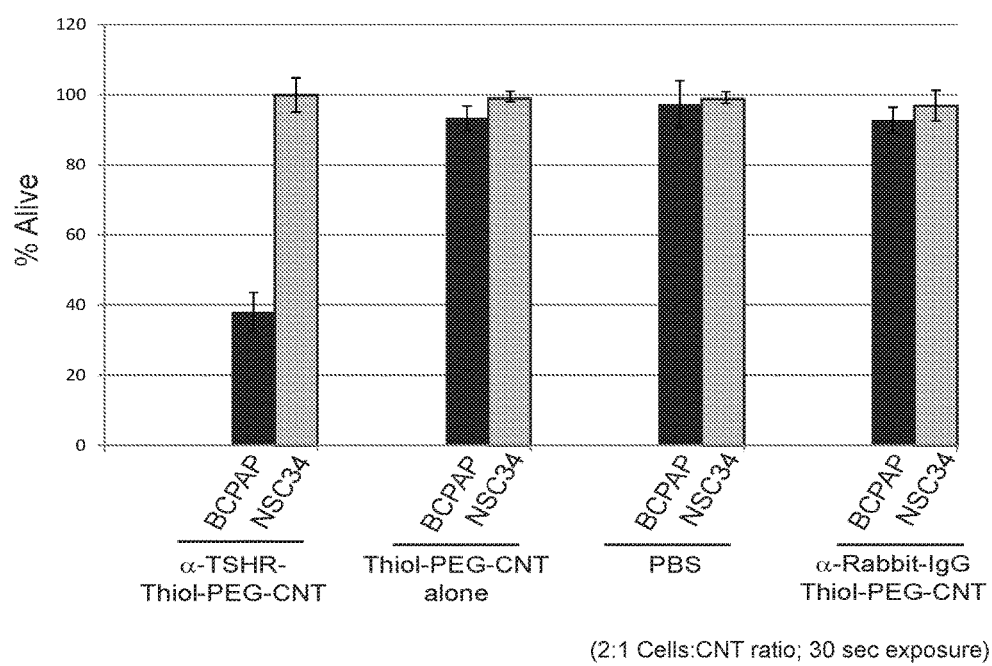

FIG. 37. Cell ablation studies using α-TSHR-Thiol-PEG-CNTs, of TSHR positive BCPAP cells vs. TSHR negative-NSC34 cells. Cells were mixed with α-TSHR-Thiol-PEG-CNT-bionanofluid at 37° C. for 1 hr, cells were washed 5× with PBS and re-suspended in PBS and exposed to 532 nm laser for 30 sec. An aliquot of cells was removed to give a pre-count of cells. 2:1 cell:bionanofluid, and 30 sec exposure was used. Experiment was repeated n=4. Cells counted using a haemocytometer.

Figure 38A:
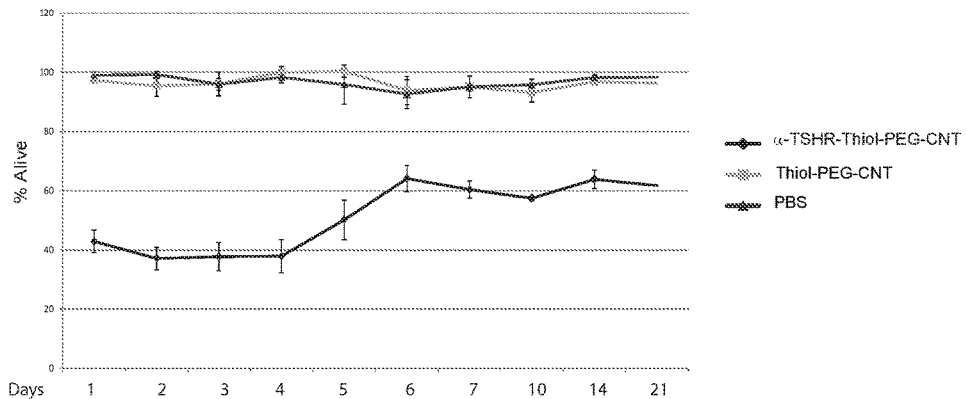
Figure 38B:
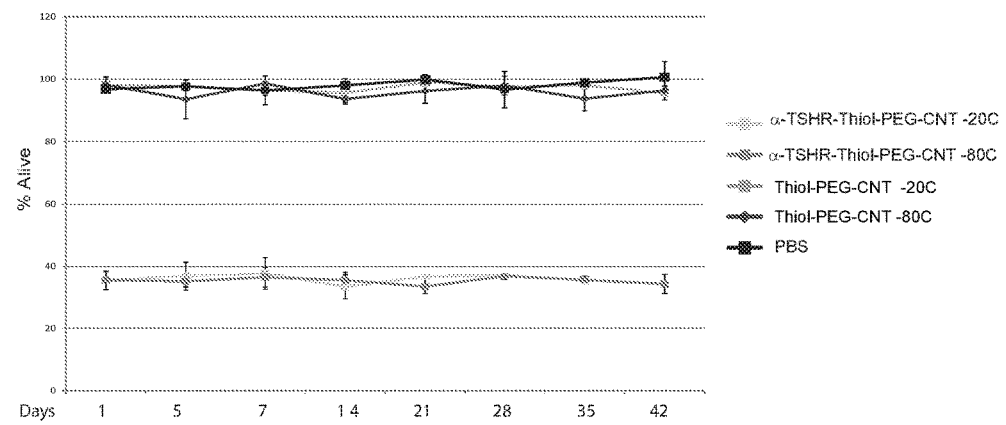

FIG. 38. Cell ablation studies using α-TSHR-Thiol-PEG-CNTs, of TSHR positive BCPAP cells to determine stability carbon-derived bionanofluid, at A. 4° C. or B. −20° C. or −80° C. Cells were mixed with TSHR-bionanofluid at 37° C. for 1 hr, cells were washed 5× with PBS and re-suspended in PBS and exposed to 532 nm laser for 30 sec. An aliquot of cells was removed to give a pre-count of cells. 2:1 cell:bionanofluid, and 30 sec exposure was used. Experiment was repeated n=4. Cells counted using a haemocytometer.

Figure 39:
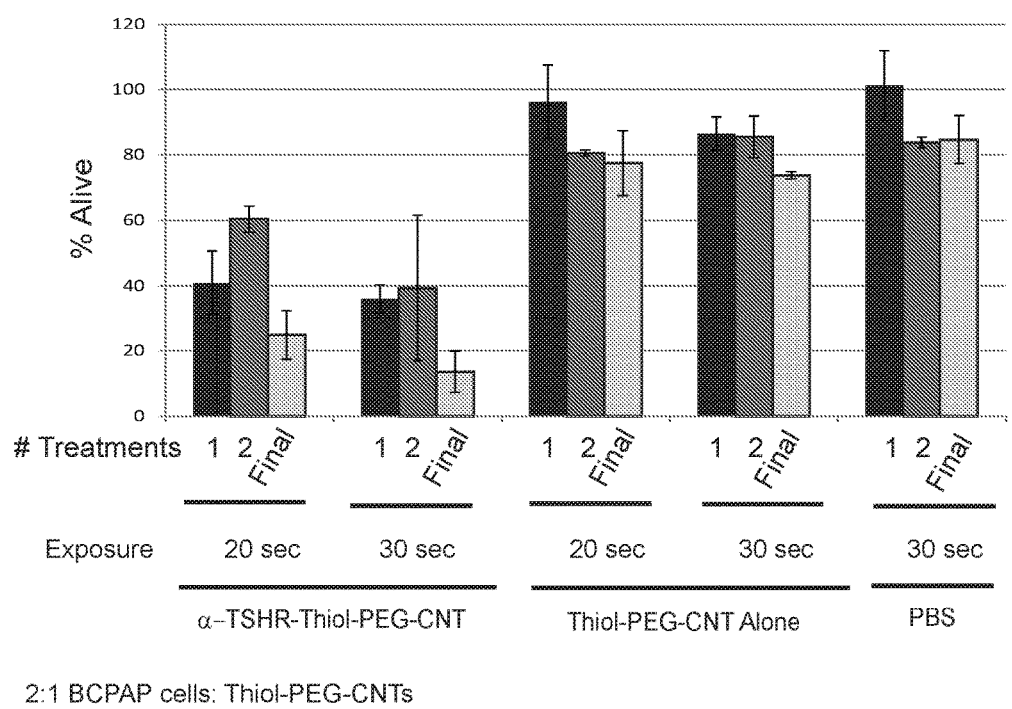

FIG. 39. Multiple treatment cell ablation studies using α-TSHR-Thiol-PEG-CNTs. Cells were mixed with α-TSHR-Thiol-PEG-CNT-bionanofluid at 37° C. for 1 hr, cells were washed 5× with PBS and re-suspended in PBS and exposed to 532 nm laser for 30 sec. An aliquot of cells was removed to give a pre-count of cells. After laser exposure, cells were mixed with Trypan blue, and white cells or live cells were counted. Afterwards, cells were reseed on 6-well plates RMPI1640+10% FBS for 48 hrs. After which cells were collected again And exposed to α-TSHR-Thiol-PEG-CNT-bionanofluid as described previously. Results given as % Alive and experiment performed n=6. 2:1 ratio cells to bionanofluid and 30 sec exposure was determined optimal.

Figure 40:
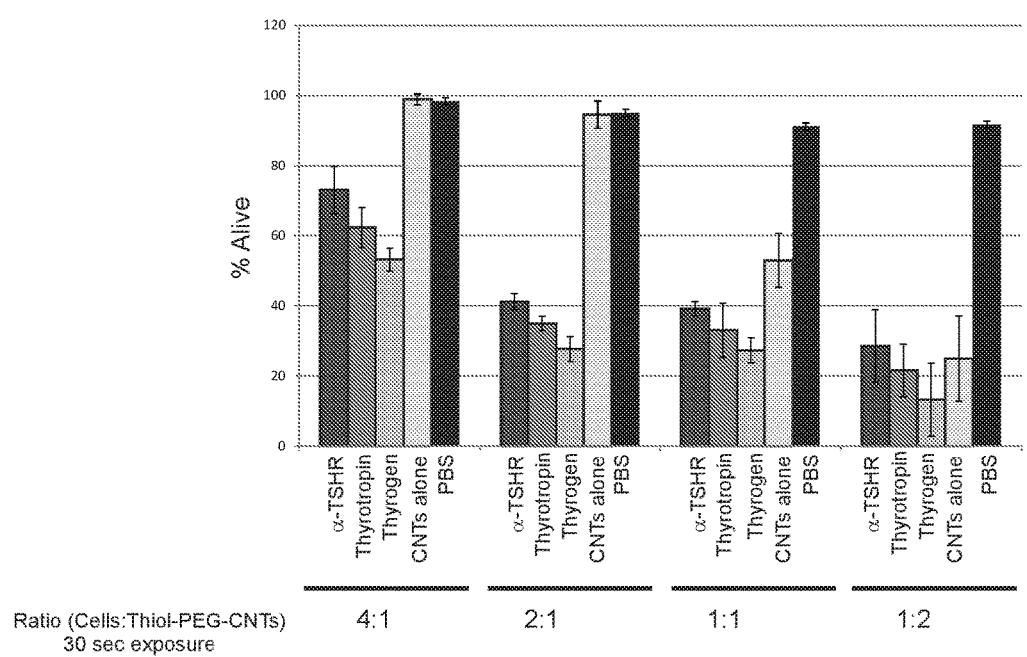

FIG. 40. Cell ablation studies using either Thyrogen (TSH recombinant)- or thyrotropin (TSH purifiied)-Thiol-PEG-CNTs, to determine concentration of cells to CNT particle. Cells were mixed with TSH-bionanofluid at 37° C. for 1 hr, cells were washed 5× with PBS and re-suspended in PBS and exposed to 532 nm laser for 30 sec. An aliquot of cells was removed to give a pre-count of cells. After laser exposure, cells were mixed with Trypan blue, and white cells or live cells were counted. Results given as % Alive and experiment performed n=6. 2:1 ratio cells to bionanofluid was determined optimal, as higher concentrations of bio-nanofluid results in bulk-heating. Cells counted using a haemocytometer.

Figure 41:
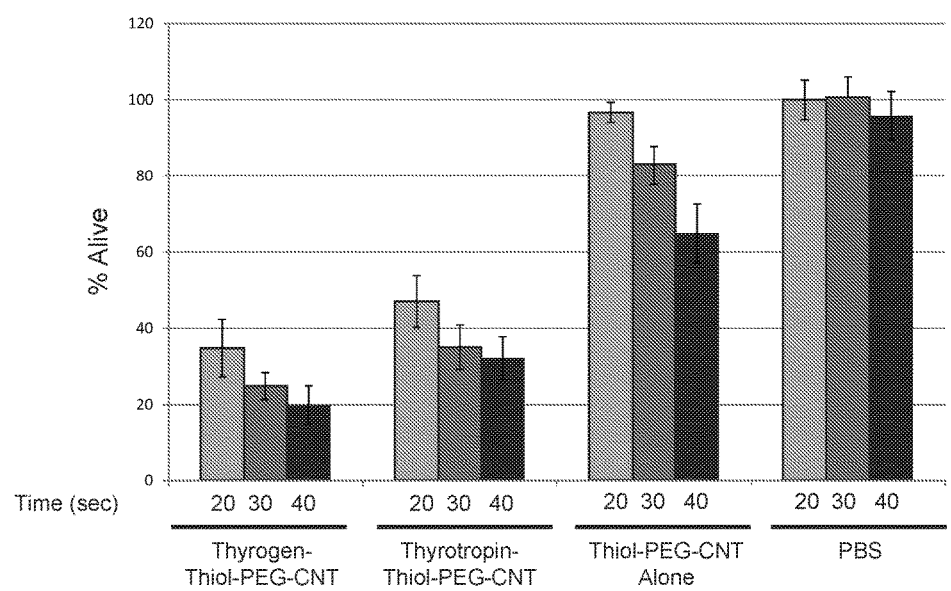

FIG. 41. Cell ablation studies using either Thyrogen (TSH recombinant)- or thyrotropin (TSH purifiied)-Thiol-PEG-CNTs, to determine concentration of cells to CNT particle. Cells were mixed with TSH-Thiol-PEG-bionanofluid at 37° C. for 1 hr, cells were washed 5× with PBS and re-suspended in PBS and exposed to 532 nm laser for 20, 30, or 40 sec. An aliquot of cells was removed to give a pre-count of cells. After laser exposure, cells were mixed with Trypan blue, and white cells or live cells were counted. Results given as % Alive and experiment performed n=6. 30 seconds laser exposure of cells to bionanofluid was determined optimal, as higher concentrations of bionanofluid results in bulk-heating. Cells counted using a haemocytometer.

Figure 42:
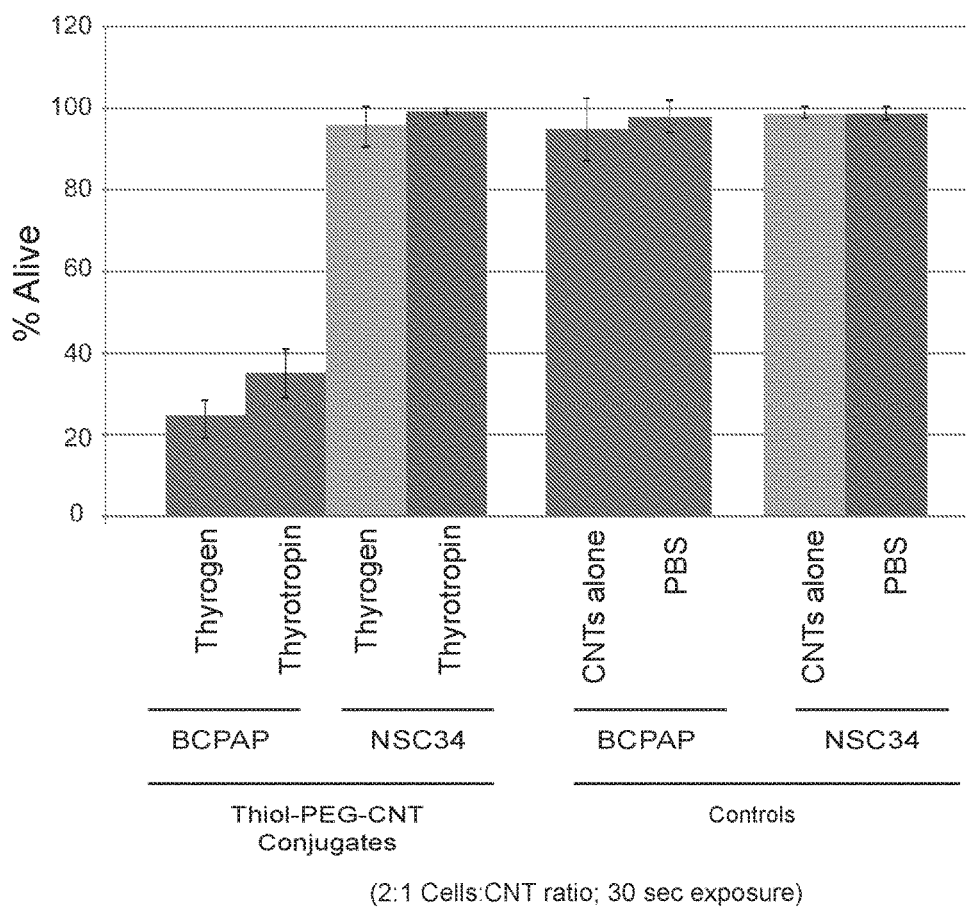

FIG. 42. Cell ablation studies using either Thyrogen (TSH recombinant)- or thyrotropin (TSH purified)-Thiol-PEG-CNTs, against TSHR-positive BCPAP cell lines vs. TSHR-negative NSC34 cell lines. Cells were mixed with TSH-Thiol-PEG-bionanofluid at 37° C. for 1 hr, cells were washed 5× with PBS and re-suspended in PBS and exposed to 532 nm laser for 30 sec. An aliquot of cells was removed to give a pre-count of cells. After laser exposure, cells were mixed with Trypan blue, and white cells or live cells were counted. Results given as % Alive and experiment performed n=4. Cells counted using a haemocytometer.

Figure 43:
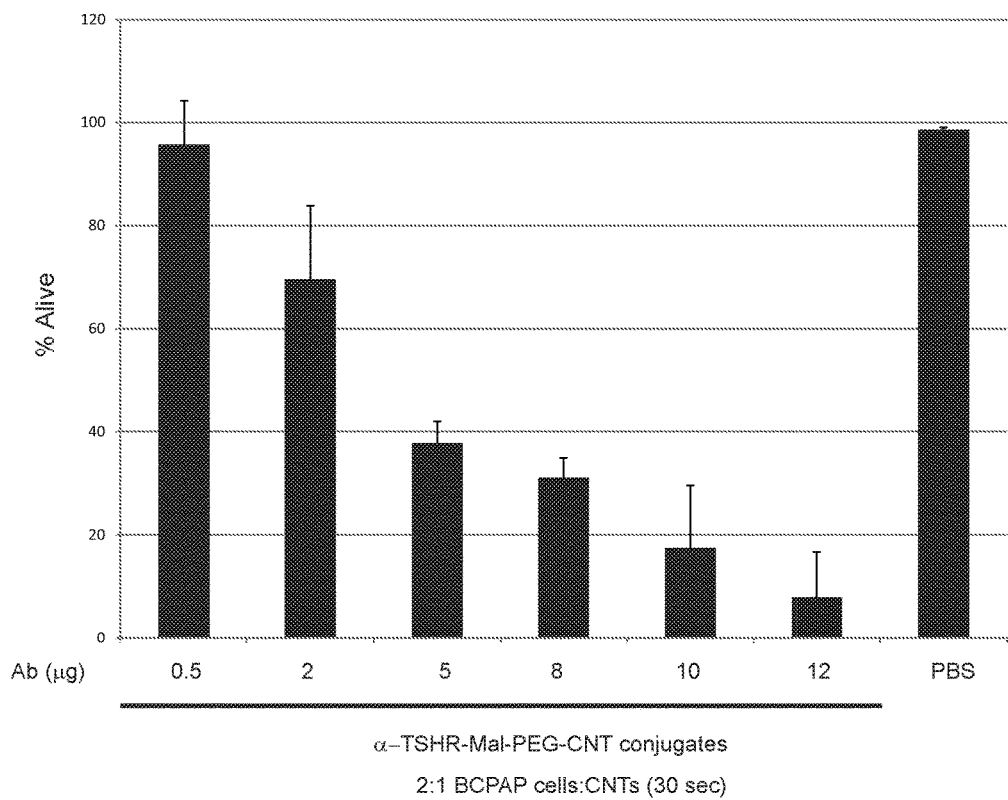

FIG. 43. Cell ablation studies using different amounts of TSHR antibody conjugated to Mal-PEG-CNTs. Cells were mixed with α-TSH-Mal-PEG bionanofluid at 37° C. for 1 hr, cells were washed 5× with PBS and re-suspended in PBS and exposed to 532 nm laser for 30 sec. An aliquot of cells was removed to give a pre-count of cells. After laser exposure, cells were mixed with Trypan blue, and white cells or live cells were counted. Results given as % Alive and experiment performed n=3. Cells counted using a haemocytometer.

Figure 44:
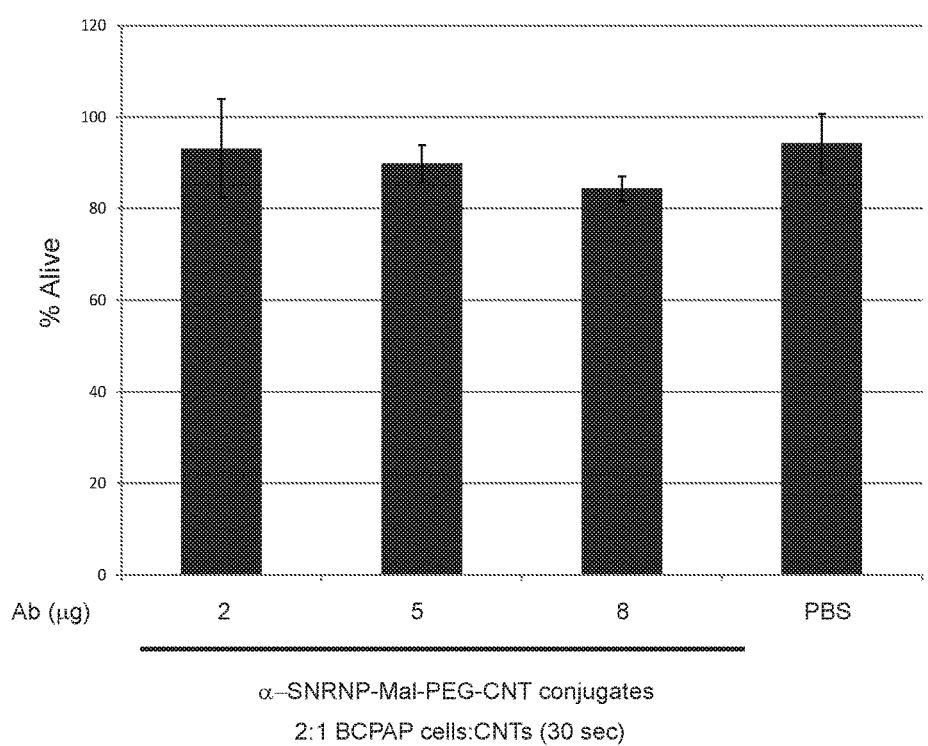

FIG. 44. Cell ablation studies using different amounts of SNRNP antibody conjugated to Mal-PEG-CNTs. SNRNP is an intracellular protein, thus showed negligible effects on cell killing. Cells were mixed with α-SNRNP-Mal-PEG-bionanofluid at 37° C. for 1 hr, cells were washed 5× with PBS and re-suspended in PBS and exposed to 532 nm laser for 30 sec. An aliquot of cells was removed to give a pre-count of cells. After laser exposure, cells were mixed with Trypan blue, and white cells or live cells were counted. Results given as % Alive and experiment performed n=3. Cells counted using a haemocytometer.

Figure 45:
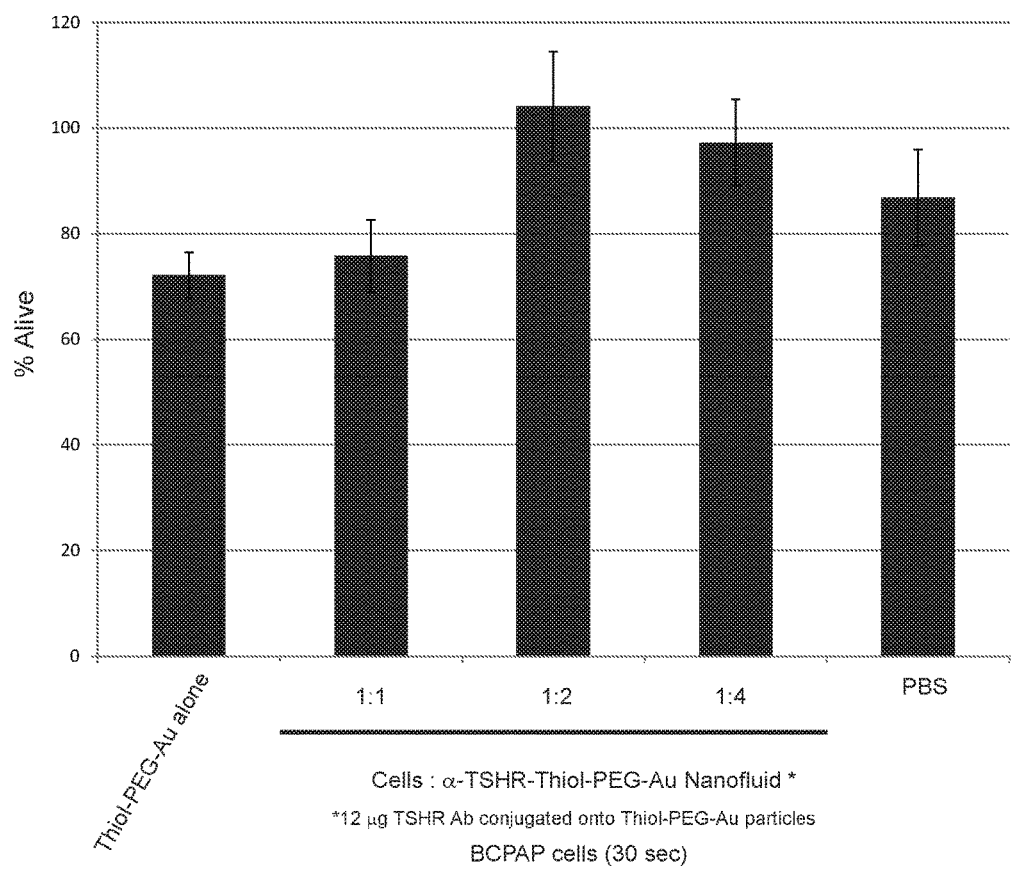

FIG. 45. Cell ablation studies using different ratios of BCPAP cells to TSHR antibody conjugated to Au-Thiol-PEG-CNTs. Cells were mixed with α-TSHR-Au-nanoparticles at 37° C. for 1 hr, cells were washed 5× with PBS and re-suspended in PBS and exposed to 532 nm laser for 30 sec. An aliquot of cells was removed to give a pre-count of cells. After laser exposure, cells were mixed with Trypan blue, and white cells or live cells were counted. Results given as % Alive and experiment performed n=3. Cells counted using a haemocytometer.

Figure 46:
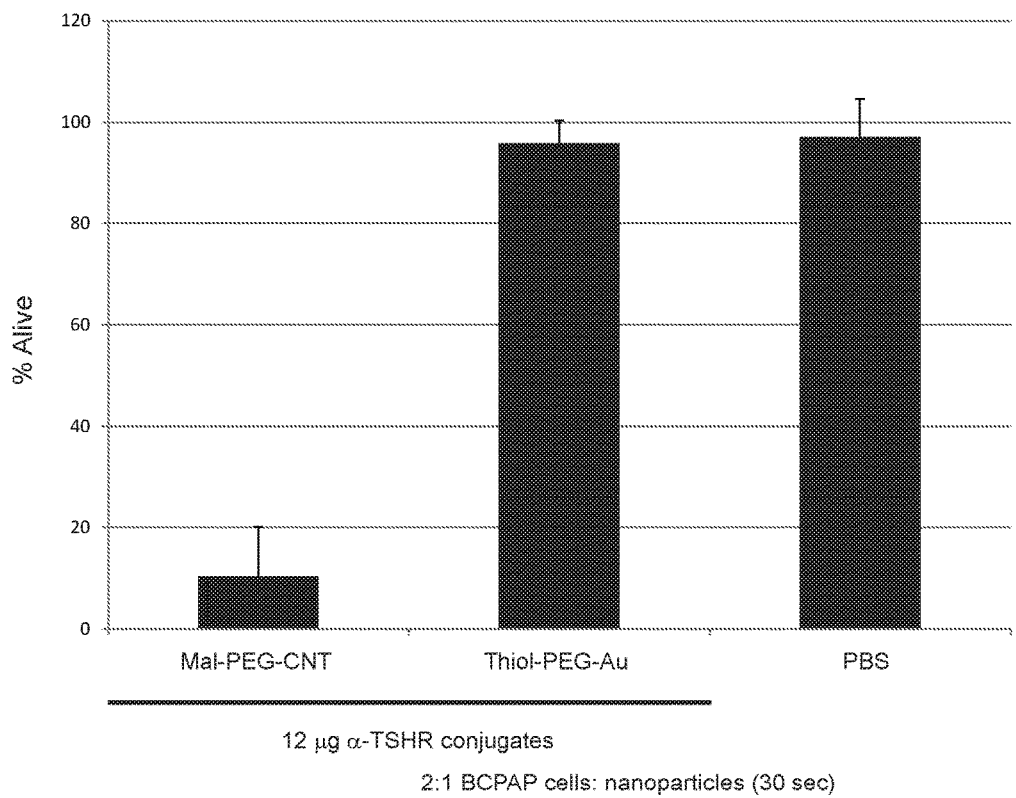

FIG. 46. Cell ablation studies using either α-TSHR-Mail-PEG-CNT vs. α-TSHR-Thiol-PEG-Au particles. Cells were mixed with α-TSHR-Mail-PEG-CNT or α-TSHR-Thiol-PEG-Au-particles bionanofluid at 37° C. for 1 hr, cells were washed 5× with PBS and re-suspended in PBS and exposed to 532 nm laser for 30 sec. An aliquot of cells was removed to give a pre-count of cells. After laser exposure, cells were mixed with Trypan blue, and white cells or live cells were counted. Results given as % Alive and experiment performed n=3. Cells counted using a haemocytometer.

Figure 47:
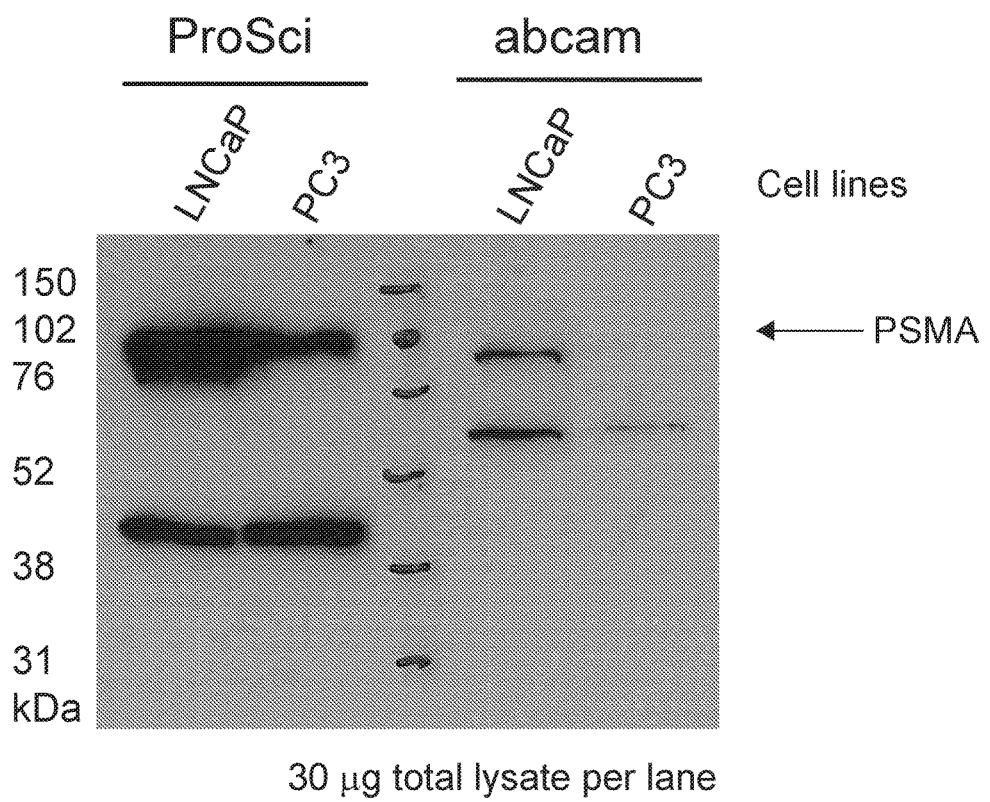

FIG. 47. Western blot analysis of PSMA (prostate specific membrane antigen) from LNCaP and PC3 prostate cancer cell lines. Commercially available PSMA from ProSci (Poway, Calif., USA) and Abcam (Cambridge, Mass., USA), were blotted on 30 μg of total protein lysate. Predicted molecular weight of PSMA is approximately 100 kDa. PSMA antibody from Abcam was chosen for all subsequent cell ablation studies FIG. 48. Western blot analysis of TSHR (thyroid stimulating hormone receptor) from a number of cancer cell lines. Commercially available TSHR from Novus Biologicals (Littleton, Colo., USA), were blotted on 30 μg of total protein lysate. Predicted molecular weight of TSHR is approximately 80 kDa. Papillary thyroid cancer cell line BCPAP and NSC34 cell lines were used in all subsequent experiments.

Figure 49:
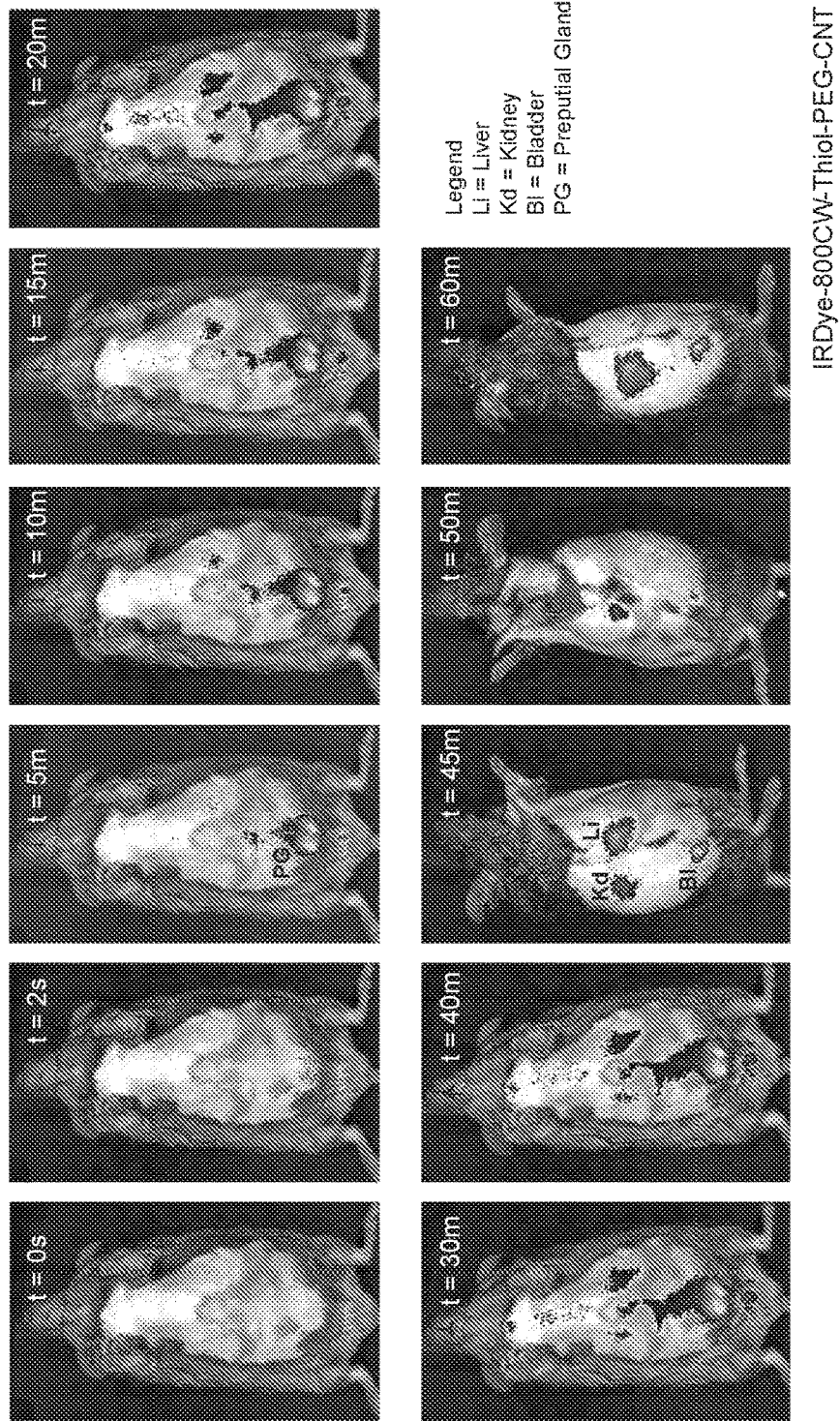

FIG. 49. Bio-distribution analysis. Hybrid-BioNanofluids labelled with IRDye-800CW were injected into the tail vein of a mouse. The distribution was followed over 60 minutes. Particles are shown to distribution through the major organs before removed by fecal and renal excretion. No observable retention of functional ligands for tissues of the heart and lungs.

DETAILED DESCRIPTION OF EMBODIMENTS

As mentioned above, embodiments of the invention relate to a bionanofluid, an hybrid bionanofluid, a hydrogel, foam, cream or spray containing thereof and their use thereof as ultrasound, imaging, disinfecting and/or therapeutic agent.

The bionanofluid contains a carbon-based nanomaterial substantially mono-dispersed in a fluid. The carbon-based nanomaterial is surface modified with polar groups when the fluid is polar or with non-polar groups when the fluid is non-polar. Moreover, the carbon-based nanomaterial is functionalized with targeting moieties to allow specific association of the carbon-based nanomaterial to targeted entities. Hybrid bionanofluids are an additional variant upon carbon derived particles where additional nanomaterials are joined with the biofunctionalized system to extend applications.

Bionanofluid

Generally speaking, the bionanofluid consists of a stable colloidal suspension of nanometer-sized particles in a base fluid. In other words, the bionanofluid can be defined as a base fluid having nanometer-sized particles uniformly dispersed therein. The carbon based-nanomaterial is substantially mono-dispersed in the fluid. Hence, the carbon based-nanomaterial can be substantially homogenously or uniformly dispersed in the fluid. In other words, the carbon-based nanomaterial do not substantially aggregates in the fluid. The dispersibility of the carbon-based nanomaterial is possible thanks to the functional groups present at the surface thereof. As detailed therein, the carbon-based nanomaterial can be functionalized with polar or non-polar groups, thereby providing an overall electric charge at the surface of the carbon-based nanomaterial relative to solvent and biological fluid. A point of differentiation from nano-fluids is the balance of surface charge and interaction with biological molecules. The presence of groups with overall negative or positive charges at the surface of the carbon-base nanomaterials cause repulsion between them that lead to mono-dispersibility. Mono-dispersibility can depend on the concentration of the carbon-based nanomaterial in the fluid, as for the solubility of any chemical species in solution which can eventually reach saturation, where the repulsive charge between particles cannot overcome aggregation. If required, aggregation can be avoided for increased nanomaterial concentration by using chemically-attached detergent molecules and/or unbound detergent as additives in the fluid. Moreover, aggregation can also occur if charge is added to the carbon-based nanomaterial in non-polar solutions and if charge is cancelled in polar solutions. Using suitable combinations of groups on the surface of the carbon-based nanomaterial and fluid can avoid this issue. Suitable combinations can include carbon-based nanomaterial with polar groups dispersed in a polar fluid or carbon-based nanomaterial with non-polar groups dispersed in a non-polar fluid, optionally including a detergent for more concentrated fluids.

The bionanofluid includes carbon-based nanomaterials, such as CarbonNanoTubes (CNT) and/or carbon nanoparticles. Nanometer-sized materials can be defined as materials with at least one dimension below 100 nm. However, materials not meeting this threshold, but still of a small enough size to exhibit properties typically associated with nanoparticles, may however still be considered within the scope of the present bionanofluid. Materials that are larger than the 100 nm limit as part of hybrid carbon-based nanomaterial bionanofluid formulations that are dispersed within a fluid are also included within the scope.

The bionanofluid can be defined as a fluid containing carbon-based materials modified to produce biological specificity and control interactions broadly in biological systems. This can be achieved through the addition of a biological targeting moiety including bio-affinity molecules, polymers and/or ligands that interact with biomolecules to adhere the bionanofluid to a specific target or biological function. The bionanofluid can be useful in multimodal imaging (photo-luminescence, luminescence, photo-acoustic, MRI, ultrasound) and/or cellular targeting.

The concentration of bionanofluid can be adapted upon application and biological need. It is possible to exceed 1 gram per liter concentrations, although, dependent upon functional biomodifications and nanomaterial size, the concentrations can vary substantially from nanograms per liter to grams per liter.

The bionanofluid can be dried, and more particularly air-dried or freeze-dried.

Fluid

The nanofluid requires a base fluid in which the biofunctionalized carbon-based nanomaterial can be dispersed, e.g. mono-dispersed. The fluid or solvent can be polar or non-polar. More particularly, the fluid can be a polar fluid or solvent when the carbon-based nanomaterial is provided with polar groups or it can be a non-polar fluid or solvent when the carbon-based nanomaterial is provided with non-polar groups.

In one embodiment, the polar fluid is a polar solvent. It can be a polar aprotic or a polar protic solvent. For instance, the polar fluid can be a polar aprotic solvent such as a non O—H or N—H containing solvent with a dielectric constant between 5-20 and highly polar bonds, preferably dichloromethane, tetrahydrofuran or ethyl acetate. The polar solvent can also be an aprotic polar solvent such as a non O—H or N—H containing solvent with a dielectric constant over 20 and highly polar bonds, preferably acetone, N,N-dimethylformamide, acetontrilie or dimethyl sulfoxide. The polar fluid can also be a polar protic solvent that has a high dielectric constant and possesses O—H and N—H bonds, such as ammonia, butanol, propanol, ethanol, methanol, acetic acid or water. The polar fluid can also be a combination of any of these polar solvents.

Deionized or reverse osmosis water may preferably be used as the base fluid for biological applications.

In another embodiment, the non-polar fluid can be a non-polar solvent including a liquid alkane such as butane, pentane or hexane; a cyclic alkanes such as cyclohexane; a substituted or unsubstituted aromatic such as toluene; an halogenated alkane such as choloromethane; or diethyl ether. The non-polar fluid can also be any combination of these non-polar solvents.

Moreover, for some specific applications, the fluid making up the bionanofluid has to be biocompatible and sterile. The bionanofluid should be appropriately buffered to maintain a physiological pH and ionic strength such that the biomodifications of the carbon-based nanomaterial are maintained in native and functional structures. Example of buffers can include detergents, glycols, or organic polymers such as chitosan.

Carbon-based Nanomaterial

The principal nanoscale materials dispersed in the base fluid can be carbon-based nanomaterials that are generally understood to be allotropes of carbon having a cylindrical or spherical structure defining an outer surface and an inner surface or planar structure of singular/stacked graphene sheet.

The carbon-based nanomaterial can include a variety of carbon-based nanostructures known in the art. The bionanofluid can also include a combination of different types of carbon-based nanostructures. For instance, the carbon-based nanomaterial can be tubes, spheres and derivative structures including carbon atoms. Hence, the carbon-based nanomaterial can contain carbon-based nanoparticles, nanotubes, nanobuds, graphite-like stacked sheets or any mixtures thereof. In addition, the nanomaterial usually has at least one dimension below 100 nm.

Spherical structures, such as carbon-based nanoparticles can be carbon-based spherical graphitic particles or carbon dots. Tubular structures such as carbon-based nanotubes can include single walled, double walled or multiple walled carbon nanotubes, but also nanotubes with fractured walls or enclosed structures, and fractured carbon nanotubes with non-linear geometries.

In the case of tubes, length can be between 50 microns and 1 nm, with diameter varying over the same range. Spheres such as carbon dots, graphite-like stacked sheets, or structures of carbon 60 and multiples (e.g. graphene flakes) can vary between 1 nm to 300 nm. In some cases, they can be much larger in one dimension than another, such to exceed 1-10 microns.

All carbon-derived geometries are highly variable and performance can be dictated by the dominant structure. Geometries of the carbon-based nanomaterial can include straight structures, but for fractured tubes where the rigidity of concentric graphene walls is diminished, bent, curled and/or waved tubes are also possible. The carbon nanotubes geometries can also be dictated by the orientation of the hexagonal lattice which can exhibit different thirality' e.g. armchair or zig-zag.

Carbon-based nanoparticles/nanotubes having broad range of sizes and geometries can be used in the bionanofluid. The broad range of sizes and geometries can confer a broadband interactivity with acoustic waves utilised by ultrasound for imaging purposes. Moreover, light over the UltraViolet/Visible/NearInfraRed (UV/VIS/NIR) proportion of the spectrum is absorbed by the bionanofluid, as the carbon-base nanomaterial has excellent photonic properties over this range when interacting with suitable laser/light emitting diode (LED)/lamp sources.

Geometric and dimensional properties of the carbon-based nanomaterial can be altered via fractionation using chemical oxidation/reduction, pyrolysis, filtration, controlled growth, or fracturing using high intensity ultrasonic probes. While broad range of sizes and geometries of carbon-based nanomaterials can be used to make various bionanofluids, more closely grouped size distributions can be preferred for some applications. Such grouped size distributions can be obtained by size exclusion filtration, either by dialysis or membrane filtration, of the carbon-based nanomaterials. For instance, gels and foams to be applied externally on a surface (e.g. a surface to be cleaned or disinfected) can be prepared using bionanofluids with carbon-based materials within the micrometer length. Indeed, for such an application, the carbon-based nanomaterials will not need to enter or be required to enter the circulatory system, or be absorbed through membranes (vessel walls, blood brain barrier, etc.). For tumors treatment or imaging purposes, where intravenous injection is the preferred method of delivery, smaller particles and close groupings can prevent issues of clotting and aggregation, aiding rapid distribution through the circulatory system and lymphatic system. Moreover, the use of carbon-based materials having a size range in the low nanometer range can be preferable compared to larger size range materials which can be prevented from passing through the blood brain barrier without the aid of active transport.

Polar and Non-polar Groups

As mentioned above, the carbon-based nanomaterials of the bionanofluid possess polar or non-polar groups, more particularly provided on their surface (outer surface in the case of carbon-based nanotubes or carbon-based nanoparticles). The presence of such groups enhances dispersibility of the carbon-based nanomaterials in the base fluid. More particularly, when the nanomaterial is provided with polar groups, it will be dispersed in a polar fluid and when the nanomaterial is provided with non-polar groups, a non-polar fluid will be required for its dispersion. Moreover, the polar or non-polar groups on the carbon-based nanomaterial's surface can act as attachments means for the targeting moieties and/or for spacer molecules if such spacer molecules are required.

Hydrophilic carbon-based nanomaterials can be achieved by the presence of polar groups that allow hydrogen bonding to occur. Groups added to the carbon-based nanomaterials surface for hydrophilic modification can be alcohols, e.g. methanol, ethanol, propanol, tert-butyl alcohols, cyclodextrins, sugars residues, ionic molecules, molecule or portion therein with polar functional groups (e.g. hydroxyl, thiol, carbonyl) or polar charged groups (amino, carboxyl, phosphate), or polar substituted ring structures. Other examples of polar groups that can be present on the carbon-based nanomaterial include alkene, polyene, ketone, aromatic, ether, alkyl halide, aldehyde, ester, amine, alcohol, carboxylic acid, cyclodextrin, glycoside, protein or sugar residues. Combinations of such polar groups can also be present on the carbon-based nanomaterial.

Groups added for hydrophobic or non-polar dispersion can be alkanes, alkenes, oils, fats, saturated fatty acids, waxes, molecules or portion therein with non-polar groups (e.g. methyl or phenyl groups), silicones, fluorocarbons.

Moreover, addition of halogens can also be considered for bio-fouling prevention.

Targeting Moieties

Another aspect of the bionanofluid that enable its use as a contrast agent, disinfecting agent, imaging agent and/or therapeutic agent is the ability of the carbon-based nanomaterial contained therein to be functionalized with a targeting moiety. As explained therein, functionalization of the carbon-based nanomaterial can provide for their binding to target entities, for example cells.

The targeting moieties can include a variety of biological and/or chemical ligands to enable biological specificity. One can also refer to a bio-affinity molecule or agent. For in vivo and/or in vitro biological applications, such as ultrasound, imaging, disinfecting and/or therapeutic applications, the carbon-based nanomaterial can be modified by the addition of biological and/or chemical ligands specific to each application.

Targeting moieties can be biomolecules as those found native and genetically modified from native molecules found in organisms. They can be molecules that are found to bind to small drug molecules, nucleotide (DNA, RNA and derivatives), protein (structural and globular), co-factors (e.g. NADH, FADH), lipid or glycoside entities. Antibodies, aptamers, oligo-peptides, hormones and small molecules with strong affinity for proteins (for example biotin) can be used for biological recognition and can be defined as targeting moieties or bio-affinity agents.

In an embodiment, targeting moieties can include nucleic acids (DNA, RNA and derivatives), oligonucleotides, peptides (e.g. oligo-peptides), proteins, or any other biocompatible ligands capable to be attached to the groups provided on the surface of the carbon-based nanomaterial.

Other examples of targeting moieties can be antibodies, such as α-TSHR (thyroid stimulating hormone receptor), α-PSMA (prostate specific membrane antigen) or any other monoclonal or polyclonal antibody, nucleic acid (DNA or RNA) aptamers or glycosides. However, the targeting moieties can also be smaller molecules including for example thyrotropin/TSH (recombinant or purified), α-snRNP (small nuclear ribonucleic protein), polyethyleneglycol (PEG) and/or small drug molecules.

Inclusion by physical absorption or chemi-adsorption of bio-compatible molecules such as polyethylene glycol as targeting moieties can enhance dispersibility of the bionanofluid in plasma fluid.

In an embodiment, the carbon-based nanoparticles/tubes are reacted with polyethylene glycol (PEG) to attach PEG to their surface. The PEG molecular weight may range from 250 to 100,000 g/mol, preferably from 1,000 to 50,000 g/mol. A particular PEG has a molecular weight of 5,000 g/mol, but PEG with any other molecular weight can be used as targeting moieties.

In another embodiment, the targeting moieties can include molecules having a p orbital over a delocalized system, such as a doxorubicin, or any molecule where preservation of the $sp^2$ system and molecular structure is possible. Hence a bionanofluid involving pi-stacking interactions can be prepared. In this embodiment, a combined localized cell killing can be enabled with the action of a suitable light with appropriate light power illuminating the cells, thanks to the presence of the carbon-based nanomaterial modified with such targeting moieties which allows specificity to cell and small drug loading, e.g. doxorubicin, through pi-pi interactions.

Figure 1:
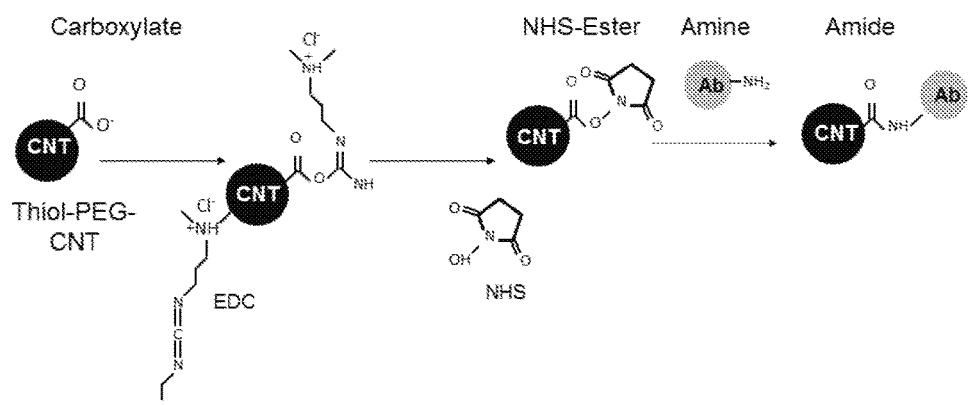
FIGS. 1 to 49 are images and diagrams illustrating various embodiments.
Figure 2:
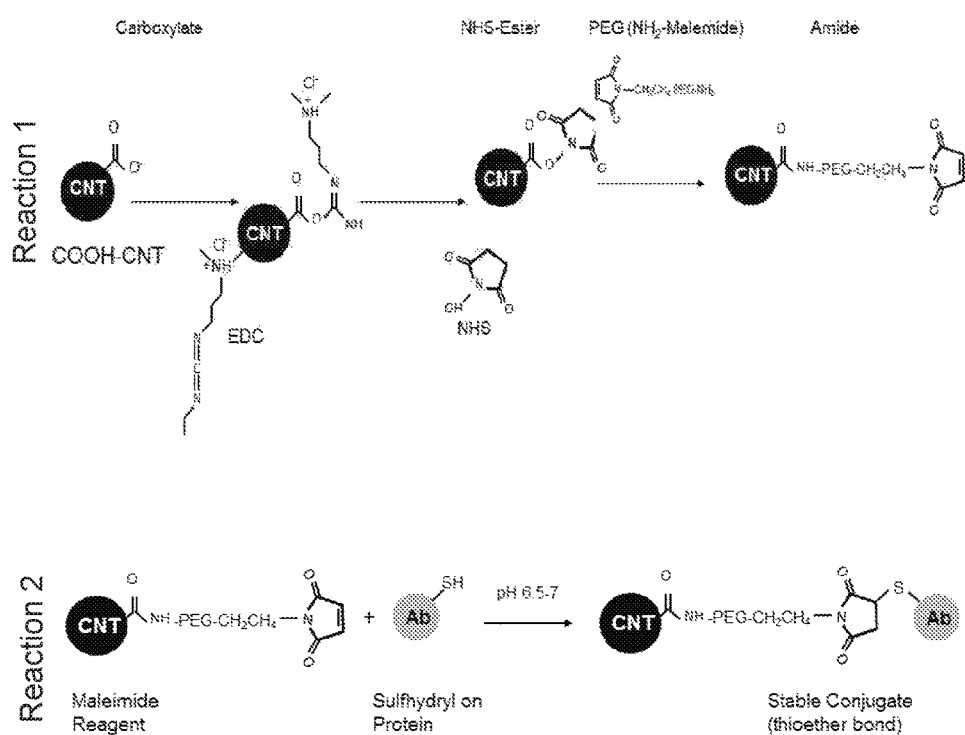
Figure 3:
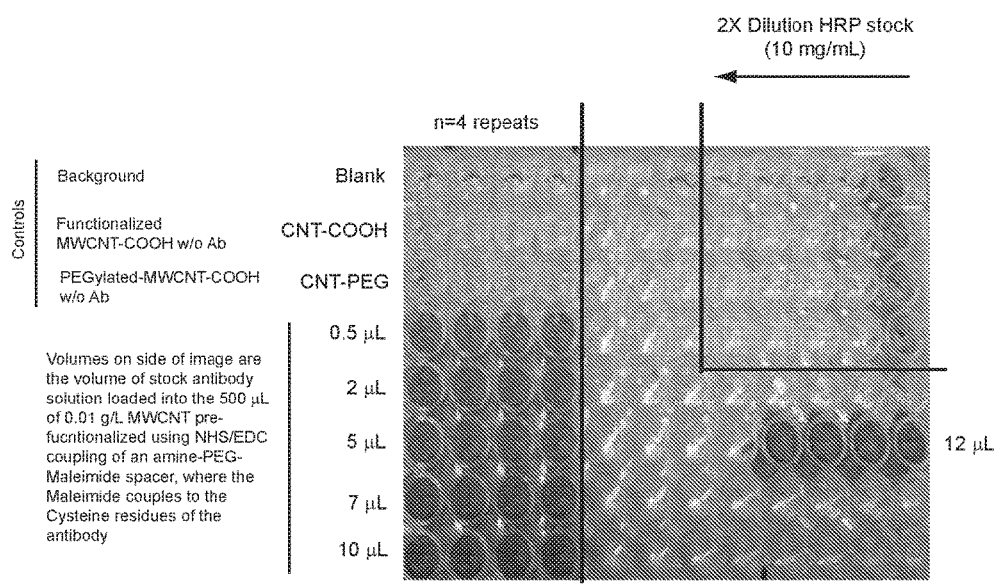

In another embodiment, the targeting moieties can be attached to the carbon-based nanomaterial either directly or through a "spacer" molecule or ligand. FIG. 1 shows the preparation of a carbon-based nanomaterial wherein the targeting moiety is attached directly to the nanomaterial. FIG. 2 and FIG. 3 show carbon-based nanomaterial with the targeting moiety attached directly to the nanomaterial through a spacer.

Spacer

As mentioned above, in some embodiments, the targeting moieties can be attached to the carbon-based nanomaterial through a "spacer" ligand. The "spacer" ligand can be defined as an extended molecule that moves the biological recognition molecule (the targeting moieties) further from the surface of carbon-based nanomaterial. The spacer can be used for example to control the targeting biomolecule attachment and/or provide the best spatial orientations while limiting steric hindrance.

In an embodiment, the spacer can be polyethyleneglycol (PEG), PEG-maleimide, amine-PEG-maleimide, a protein or combinations thereof. Example of proteins can be derivatives of protein A or G that binds globulin, avidin, streptavidin or any avidin based protein variant that binds to biotin.

In an embodiment, the spacer can include polyethylene glycol (PEG) of a molecular weight ranging from 250 to 100,000 g/mol, preferably from 1,000 to 50,000 g/mol. A particular PEG has a molecular weight of 5,000 g/mol, but PEG with any other molecular weight can be used as spacer ligand. One will understand that when the targeting moiety itself is PEG, as mentioned above, a different spacer can be used. Otherwise, PEG directly attached to the carbon-based nanomaterial forms the targeting moiety.

FIGS. 2 and 3 show the preparation of carbon-based nanomaterials (e.g. carbon nanotubes, CNT) functionalized with targeting moieties attached to the nanotubes through a spacer.

Targeted Entities

The bionanofluid is characterized in that it is designed to target various biological entities thanks to the targeting moieties attached to the carbon-based nanomaterial. The targeted entities are preferably biological entities such as prokaryotes or eukaryotes, preferably organs, tissues, cells, virus, bacteria, spores or fungi. More particularly, the targeting moieties can be associated and/or interact with specific sites on the targeted entities. Hence, localization to the targeted entities is enabled by the bio-modification with the targeting moieties on the carbon-based nanomaterial, and will ensure internal or external targeting of the moieties. The bionanofluid's photonic properties can then allow disrupting of the function of the targeted entities to the point where their viability is impossible.

In an embodiment, the targeted entities can include a variety of biological entities such as cells (eukaryotic or prokaryotic cells, mammalian cells), bacteria, virus, spores or fungi.

In an embodiment, the targeting moiety is designed for intracellular or extracellular targeting of the targeted cells.

Hybrid Bionanofluid

The carbon-based nanomaterial making up the bionanofluid can be further functionalized by attachment of other nanoparticles, referred herein to as hybrid nanoparticles, through chemical linkage to the hexagonal lattice of the gross carbon structure. With the additional targeting moieties present on the carbon-based nanomaterial and due to their dispersibility in a biologically-compatible solvent, the hybrid bionanofluid can be used in various interesting applications including for example imaging applications.

The hybrid bionanofluid can include hybrid carbon-based nanomaterial having sizes ranging from 1 to 100 nm. However, hybrid carbon-based nanomaterial of 100 nm to 10 microns can also be present, and one could then refer to a hybrid micro-fluid if the hybrid carbon-based material remains mono-dispersed in the fluid.

The hybrid nanoparticles can include an alloy, transition metal, semi-conductors, semi-metal, polymer based nanoparticle or any combination thereof. In one embodiment, the hybrid nanoparticles can include a noble metal and/or a metal of the II to VI group elements forming the semiconductor sub-groups. Semi-conducting materials can also include those nanoparticles or thin films created either by doping or junction formation and the carbon semi-conductor classes. In another embodiment, the hybrid nanoparticles can include iron (Fe), nickel (Ni), manganese (Mn), silver (Ag), gold (Au), silica and derivative thereof, titanium oxide and derivatives thereof or a combination thereof. Preferred hybrid nanoparticles include gold (Au), iron (Fe), nickel (Ni) or manganese (Mn).

Hybrid bionanofluid can be useful as imaging agents. For instance, multi-walled carbon nanotubes (MWCNT) can be functionalized with the targeting moieties to target specific entities and the presence of gold, semi-conducting, dye-loaded core-shell particles and/or plasmonically enhanced nanoparticles can enhance the imaging properties of the bionanofluid.

Hybrid bionanofluid containing iron, nickel or manganese as hybrid nanoparticles can present magnetic or paramagnetic properties and can be conjugated to proteins for example. The resulting paramagnetic bionanofluid can be particularly useful in cell capture and purification methods.

Bionanofluid and/or Hybrid Bionanofluid Preparation

Carbon nanotubes and other carbon-derived nanoparticles can be prepared by a number of chemical methods, inclusive of chemical vapor deposition (CVD), purification from soot, arc discharge, electrochemically, laser ablation/vaporisation, extraction via purification (electrophoresis, size exclusion chromatography from carbonized waste, fracture from graphite by ultrasonication/milling and/or green chemistry approaches. These methods are well known in the art. All methods commonly have a carbon source and an addition of energy to produce fragments of the starting carbon source, followed by recombination of the carbon atoms as graphene/allotropes. Synthesis may or may not include a metal or chemical catalyst.

Some carbon derived particles are formed as part of caramelization processes such as sugar/sweet manufacture where carbon is broken down to elemental form, or fractioning of the initiating carbon source and recombined as ultra-small carbon particles. Carbon-derived particles formed in this manner contain functional groups common to the starting material. The same chemical decomposition can be achieved using strong acid, high temperature and/or pressure in specific measures Addition of functional groups to carbon-based nanoparticles/tubes can be performed by wet chemistry, plasma and/or physical adsorption of metallic (i.e. gold, silver, platinum, copper, iron and other elements from transition metal section of periodic table or polymer composition) or non-metallic material to the surface of the nanoparticles/tubes. Non-metallic materials can be inclusive of elemental and polymer compositions (e.g. Teflon™) and other pure polymer and co-polymer mixes. Physically adsorbed material can be used to further modify the carbon-derived particles by forming a partial or complete capping layer.

In an embodiment, functionalizing can be achieved with a primary amine on biological or chemical entities. Usually, the reaction is carried out using N-hydroxysuccinimide (NHS) in the presence of ethyl (dimethylaminopropyl) carbodiimide (EDC) as coupling reagent (NHS/EDC coupling method). The primary amine can be any compound in which the amino group is directly bonded to a carbon atom linked to the nanoparticles chemical sub-structure.

In another embodiment, a bionanofluid containing predominantly small carbon-derived nanoparticles or predominantly carbon dots (size 1-40 to 100 nm diameter) and having pronounced photo-luminescence due to semi-conductor properties, which is modified with bio-specific molecules for cell targeting can be prepared. Functionalization with bio-specific molecules can be achieved by attachment of the bio-specific molecules to polar or non-polar groups and/or spacers on the carbon-based nanomaterial surface, described therein. PEG groups can be attached to the carbon-based nanomaterial through either amide bond formation, thiol esterification of carboxylic acid groups (e.g. carboxylic acid groups) or via the formation of Au—S linkages to the carbon-based nanomaterial. The resulting PEG-modified bionanofluid improves suspension in plasma fluid and the carbon-based nanomaterial can be further modified to enable further applications in photothermal treatment and in targeted cancer therapies, as explained further below. In an embodiment, the PEG can serve as a "spacer" ligand to which other targeting moieties can be attached. Alternatively, bi-functional PEGs (e.g. amine-PEG-maleimide) can be substituted for the basic PEG ligand to control biomolecule addition and present biomolecules/small molecule ligands in the best orientations and with limited steric hindrance.

In another embodiment, the carbon-based nanomaterial can be functionalized with biomolecules by thio-esterification. The reaction can involve the use of sulfur-containing biomolecules (thiolated molecules) or the thiol function involved in the thio-esterification reaction can be present on the carbon derived nanoparticles themselves.

Examples of biomolecules that can be attached to the carbon-based nanomaterial using this thio-esterification method include proteins. They can be attached as the targeting moieties or as a spacer to which other biomolecules can be attached. For example, carbon-based nanomaterial functionalized with streptavidin or any avidin-based protein variant that binds biotin can be prepared. In this case, the streptavidin or avidin-based protein variant can act as spacers and biotin is attached thereto as the targeting moiety. However, it is also possible that the carbon-based nanomaterials is functionalized with biotin as a spacer and avidin-based protein variants can then be attached to the biotin as targeting moieties.

In another embodiment, hybrid bionanofluids are created by attachment of hybrid nanoparticles, such as paramagnetic nanoparticles to the carbon-based nanomaterial. While hybrid nanoparticles can be attached or deposited at the surface of the carbon-based nanomaterial, in some other embodiments, the hybrid nanoparticles can be attached to targeting moieties which are themselves bounded to the carbon-based nanomaterial through an amide bond, a thio-ester bond (e.g. a thioester biotin) or by any other known coupling method. Magnetic particles include ferrous particles, nickel, manganese or any variant that possesses magnetic or paramagnetic properties and can be conjugated to proteins. The resulting paramagnetic bionanofluid can be particularly useful in cell capture and/or purification methods and conforms to the definition of bionanofluid expanded therein. Moreover, antibodies or other bio-affinity agents can be further attached to the carbon-based nanomaterial of the so-obtained paramagnetic bionanofluid which can then be used for capture of RNA/DNA using oligonucleotide probes.

Other hybrid bionanofluid can be prepared with carbon-based nanoparticles/tubes having hybrid nanoparticles attached thereto through chemical linkage to the hexagonal lattice of the gross carbon structure. The hybrid nanoparticles can include gold, silver, other noble metals, semi-conducting nanoparticles such as quantum dots and other III-V nanomaterials, just to name a few. Other transitional metal particles such as iron, nickel and manganese or polymer based particles such as silica or titania can also be attached as hybrid nanoparticles. Attachment can be either through chemi-sorption or physical adsorption, generation of nanoparticles can be either through ablative or wet chemical methods. Dispersal in a suitable solvent allows obtaining a mono-dispersed hybrid bionanofluid.

A variety of "tailored to purpose" bionanofluids can thus be prepared by targeted functionalization of the carbon-based nanomaterial.

Hydrogel, Foam, Cream, Spray, Dried Product

In an embodiment, the bionanofluids or the hybrid bionanofluids can be incorporated in various types of products which can be used for external applications. For example, the bionanofluids or the hybrid bionanofluids can be used to make hydrogels, silica foams, creams or sprays. Moreover, the bionanofluids or the hybrid bionanofluids can be dried to produce dried products, e.g. freeze-dried or air-dried products, for storage and/or transport convenience.

In an embodiment, the hydrogel can contain the bionanofluid which contain water and gelatin. The foam can contain the bionanofluid and silica or a derivative thereof.

Figure 4:
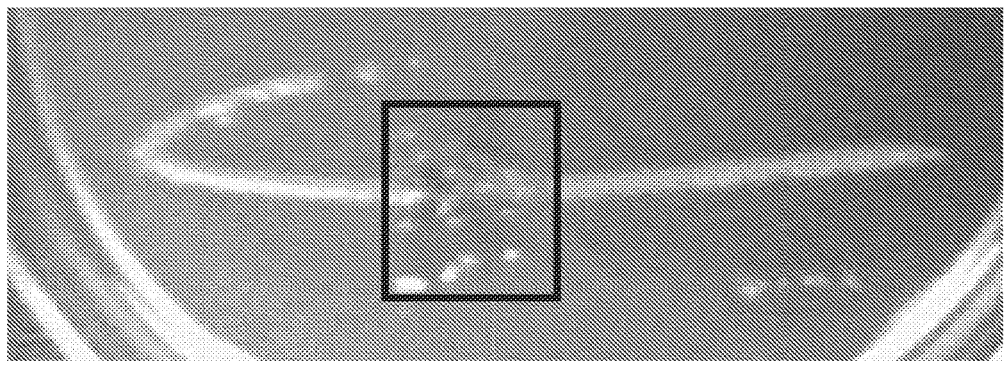

In another embodiment, the hydrogels, foams, creams or sprays can be used for disinfection using photothermal heating. They can be used for sterilization of any type of surface, but preferably to disinfect the skin. The product can be applied topically to the skin or to a surface to be sterilized and then a laser applied to the product can destroy pathogens. FIG. 4 shows a streak of DH5alpha bacteria, streaked on a LB-agar plate. A bionanofluid-containing hydrogel was added to a region and exposed to a laser. The plate was re-incubated at 37° C. overnight. However, the bacteria could not regrow in the area of the bionanofluid-containing hydrogel, thus resulting in a killing/sterilization of the area.

EXAMPLES

Synthesis of carbon-derived nanoparticles/tubes and bionanofluids

Figure 5:
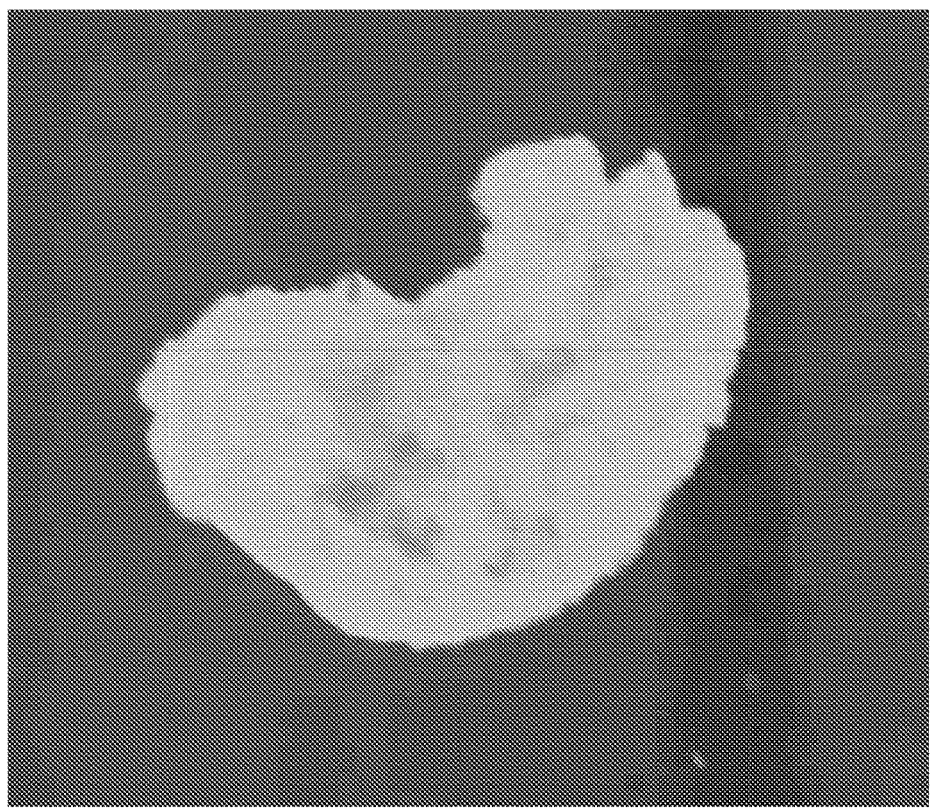
Figure 6A:
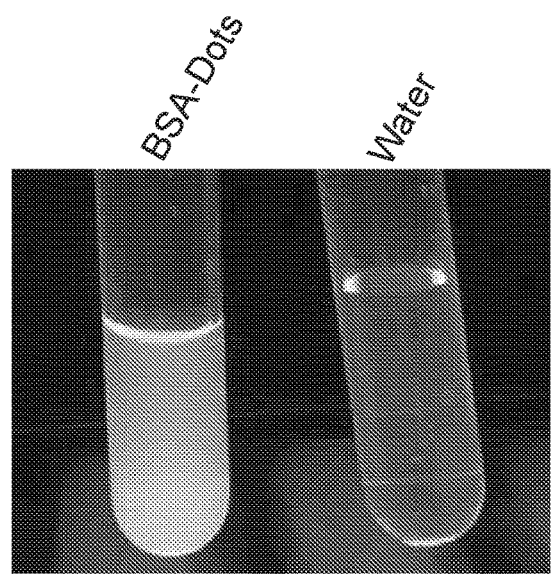
Figure 6B:
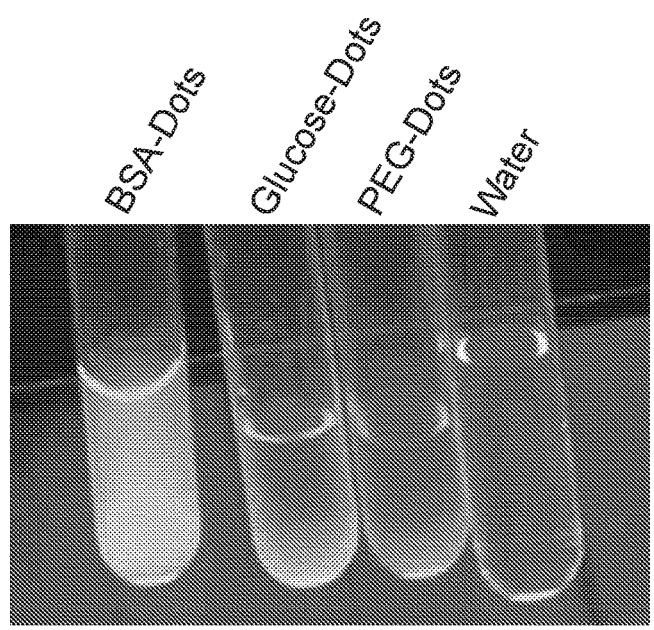

1. Carbon nanotubes (single, double, or multi-walled) are synthesized by plasma/pulsed/AC arc discharge, laser ablation and/or chemical vapour deposition. Material synthesized can have a variety of lengths, but the base material is structurally allotropes of carbon 60/graphene.
2. Other carbon particles, e.g. spherical particles, are synthesised by decomposition, such as carbon dots. Caramelization, hydrolysis, pyrolysis, microwave assisted, acid catalyzed, hydrothermal, laser ablation, arc discharge and/or chemical vapour deposition are examples of methods of synthesis.
3. Creation of a size controlled carbon bionanofluid utilizes carbon-derived particles/nanotubes prepared as mentioned above, in solid form, solubilized in a fluid, e.g. an aqueous solution, with or without detergents (e.g. ionic/non-ionic detergent).
4. Improved size of tubes and particles can be achieved by ultrasonication with tip probes. 0.5 g of carbon derived nanomaterial is placed in aqueous solution and sonicated for 2 and half hours causing tube and particle fracture. Length is reduced to below 1 micron or length appropriate to application based upon time of sonication period. Size control is further improved via filtration through a 0.45 micron filter and or dialysis against a membrane with molecular weight specified by application. For some applications, the length of tubes can be tailored to reach a specific size range. For example, the length of the tubes can be adapted to ensure circulation in the blood. Resultant filtered, size and length controlled nanotubes-nanoparticles are dispersed in the fluid (e.g. water) to form the bionanofluid. The dispersion is stable at room temperature (at 15-30° C.), preferably for about 10 months.
5. Carbon dots were synthesized by various methods as detailed below.
   a. Glucose dots: 0.1 g of glucose in 100 ml dd $H_2O$ (double distilled water) was microwaved (800 W) for 2 mins causing caramelization and dot formation. Purification was via 32,000 dalton dialysis of remaining solution. Dots were dried in 60° C. oven to form a crystalline product (FIG. 5). The bionanofluid was formed by suspension in pure water.
   b. Bovine serum albumin (BSA): Dots were created via acid catalyzed fracture of amide bonds in starting protein. 0.5 g BSA (100%) plus 5 ml concentrated sulphuric acid were mixed in Pyrex™ vessel. Formation of brown suspension occurred immediately. BSA was ground to a powder to increase surface area and solution was mixed as the acid was gradually introduced to ensure even treatment of the starting material. Reduction to elemental carbon and carbon+residual functional groups from protein occurred within seconds. The presence of dots was confirmed using a UV lamp. Purification involved neutralization of sulphuric acid using NaOH and dialysis against dd$H_2O$ (500 ml per 10 ml of neutralized dot solution). Dialysis of neutralized solution removed salts and concentration of dots was performed by evaporation of water, to form dried crystalline dots. Bionanofluid was formed by resuspension in pure water (FIG. 6A).
   c. PEG dots. A solution of PEG (MW 5,000) was dissolved in dd water and micro-waved for 5 minutes total (in 1 minute intervals). Resulting polymer gel was ground to 1 micron particles and washed using excess water. The presence of dots was confirmed with a UV lamp. The starting material could not glow, but by formation of dots, PEG polymer and ground material glowed blue (FIG. 6B). Bionanofluid was formed by suspension in pure water.

Carbon-based Particle Functionalization

Carbon dots synthesized as mentioned above have the same functional groups as their precursor carbon donating molecules. Carbon nanotubes or spherical derivatives require either plasma treatment or wet chemical modification to add functional groups. Many known methods exist for functionalizing graphene-based nanomaterials. The addition of functional groups to carbon nanotubes using standard chemistry requires additions to the carbon at breaks in the hexagonal lattice of carbon atoms. Functional groups can include nitrogen containing groups, carboxylic acids, alcohols, polymers, thiols, benzyl rings, extended rings structure (phenyalanine, anthracene) among others.

PEG Functionalization

PEG Treatment (1)
   Vortex 0.03-1 g/L carbon-based nanomaterial conjugated to gold. Gold modified entity formed by citrate reduction of gold chloride, method involved dispersal of carbon in 8% citrate solution then dilution to 1% citrate with the addition of 8 times the volume of gold chloride solution, concentration 200 mg per decaliter. Addition initiates gold particle formation on tubes. Forming a hybrid bionanofluid solution with requires CNT-gold mixture being added to an aqueous thiolated PEG 5000 MW solution in equal volumes, incubate at 30° C. for 2 hrs (elevated temperature decreases reaction time for formation of carbon-based nanomaterial-thiol-PEG complex). Centrifuge down the particles at 13000 RPM, remove supernatant. Add MilliQ water for wash step, re-suspend particles by vortexing and centrifuge again to form a highly coloured pellet (repeat 5 times). (see FIG. 1).
   Store at 4 CC in enclosed light tight box.

PEG Treatment (2)
   Bifunctional amine-PEG-maleimide was reacted with carboxyl groups of carbon-based nanomaterial (tubes or dots) in the presence of NHS/EDC to form an amide bond. Bond formation occurs within half an hour, sufficient to create an even functionalization on the carbon-based nanomaterial surface. The even functionalization allows for movement of any additional biological targeting moieties (e.g. attached through a maleimide group spacer). The great degree of freedom can enable proper binding with any other biomolecule or biological entities (FIG. 2 and FIG. 3).

Figure 7:
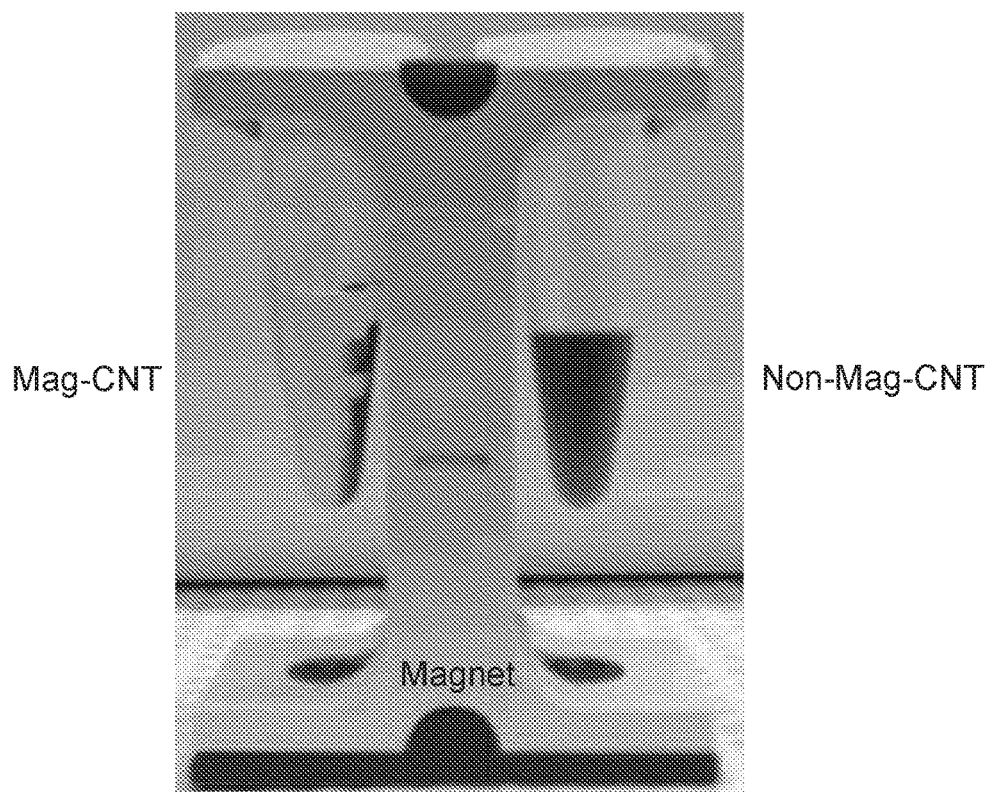
Figure 8A:
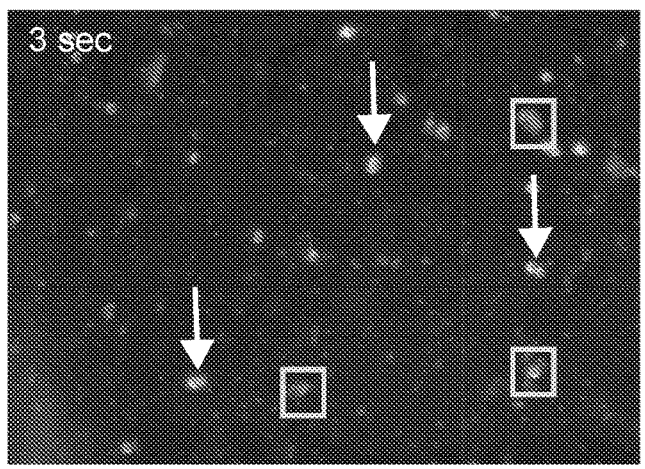
Figure 8B:
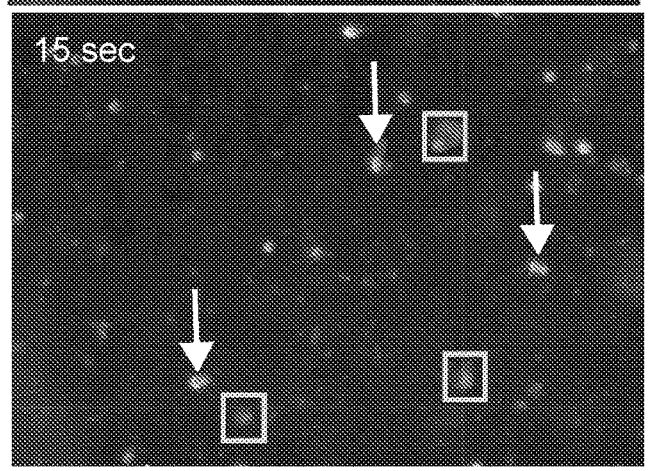
Figure 8C:
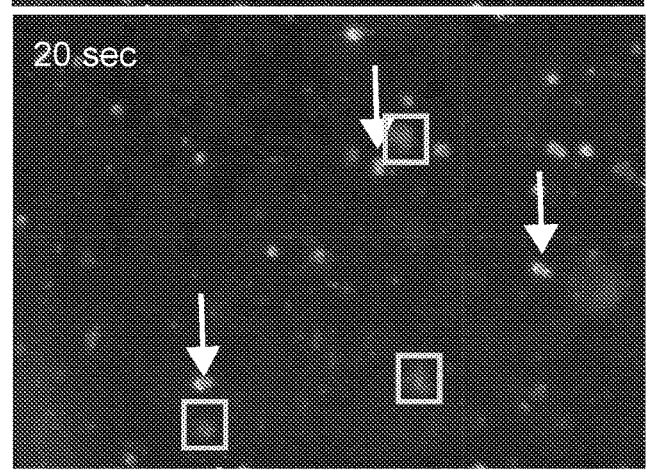
Figure 9A:
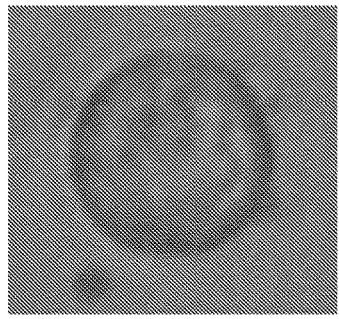
Figure 9A:
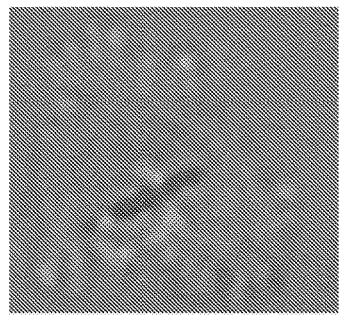
Figure 9B:
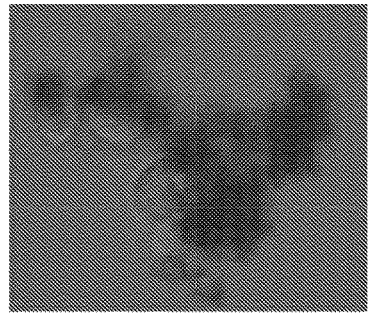
Figure 9B:
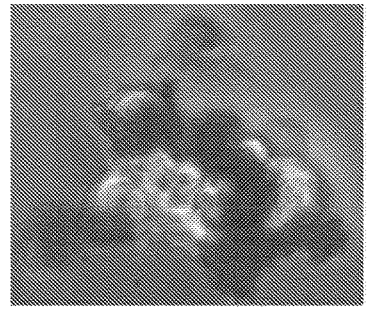
Figure 9B:
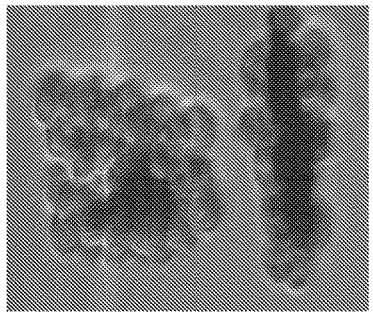

Formulation of Paramagnetic Bionanofluid 400 microliters of 0.01 mg per liter bionanofluid is mixed with 1 microliter of streptavidin-modified particles, concentration 1 mg per liter (quantities scale dependent upon starting carbon-derived nanotubes mass using the ratio 0.1 mg:1 microliter of 20 mg/ml streptavidin particles). In addition, 4 microliters of 1 mg per microliter avidin is added and mixed in. Additional avidin is provided for conjugation to bionanofluid to increase the number of available biotin binding sites to enable functionalization with oligonucleotides and other biotinylated molecules. 91 microliters of NHS is added and then 91 microliters of EDC; the volume of 1 mg/ml NHS or EDC scale with the carbon-derived nanoparticles' mass and volume. Solution is then mixed again using a vortex. The reaction reaches completion in 3 minutes, and is evidenced by the growth of the particle size, as the paramagnetic particles are conjugated through the primary amine to form an ester bond through the carboxylic acid. The individual carbon-nanotubes act as a scaffold for the attachment of the paramagnetic particles. Purification is achieved by applying a magnet and particles are re-suspended in phosphate-buffered saline. FIGS. 7, 8 and 9 contain images of the magnetized bionanofluid being used to capture cells after further modification with antibodies to confer specificity for individual cell types.

Paramagnetic particles can also be formed in a highly efficient manner using the PEG treatment (2) using the PEG maleimide functionality to bind avidin.

Sterilization of Bionanofluids

In some embodiment, the bionanofluids can be sterilized before to be used. This can involve combinations of autoclaving, ionising radiation, heat, excess UV treatment to crosslink any nucleotides present, or preparation of all solutions with MilliQ™ autoclaved water. Sterilization can also be simply done by applying a laser or light source of sufficient power to induce the photothermal conversion of light to heat.

Synthesis of Bionanofluid-containing Hydrogel

Figure 10:
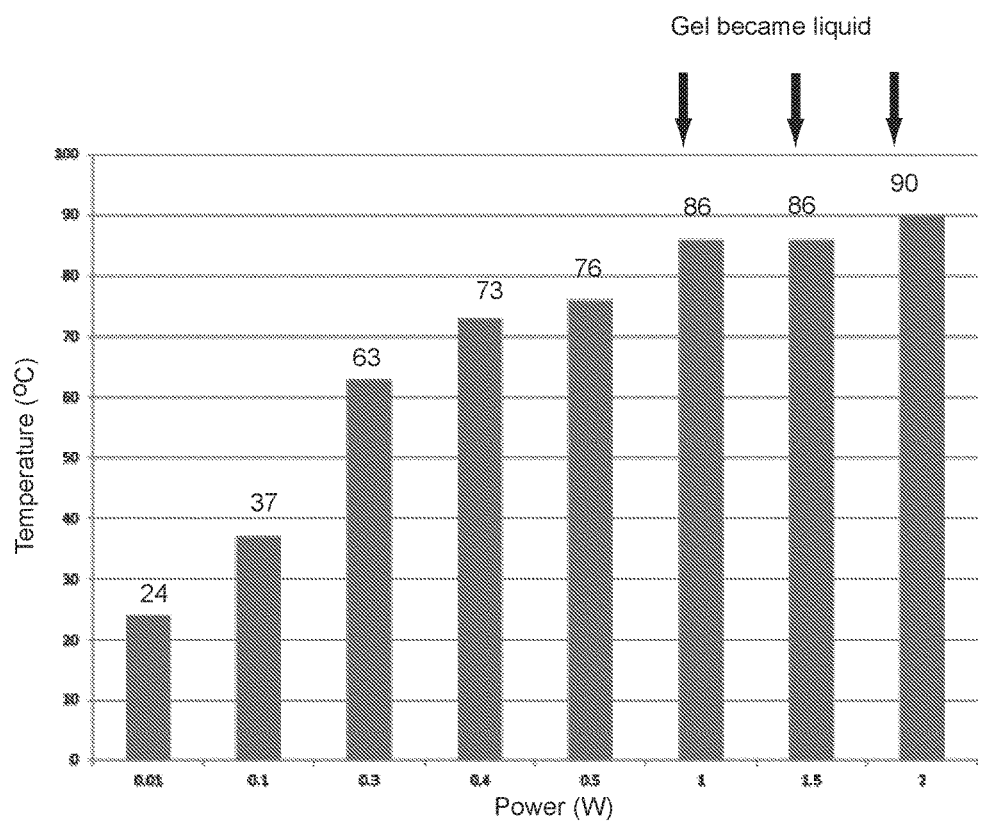
Figure 11:
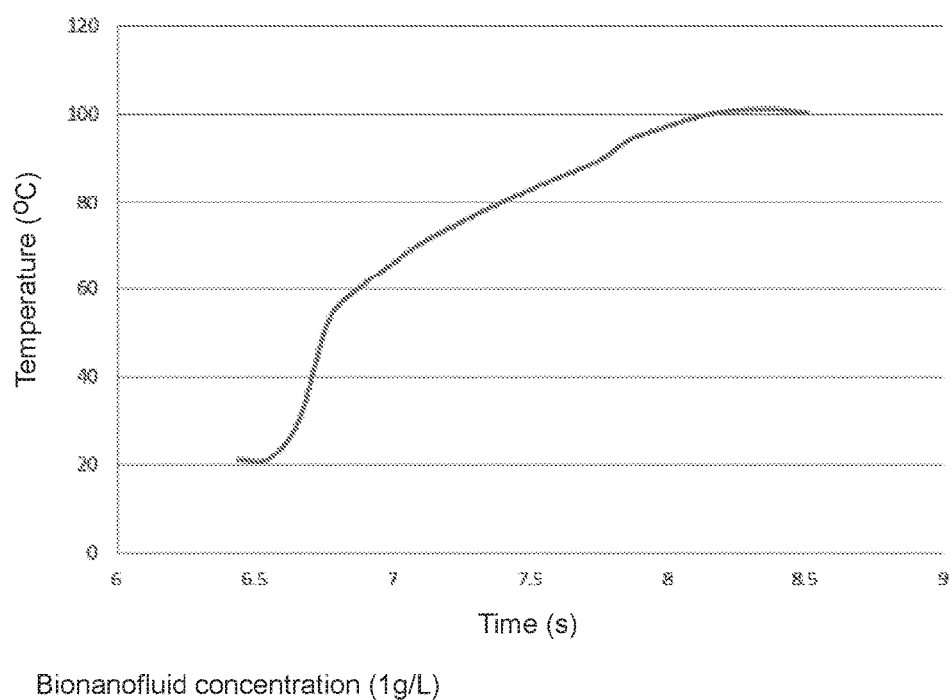

Take 0.05 grams per liter bionanofluid (made biocompatible using PEGylation or alternative grafting of biocompatible polymers), add 0.0089 grams gelatin per 20 microliters of solution. Mix vigorously until the gel is formed. Gel can be applied immediately or dried for later rehydration using the same volume as used to formulate gel. Carbon-based nanomaterial can be tubes, spherical or planar variants of the carbon-based nanoparticles or auxiliary hybrid particles. Heating rate of gel is controlled by particles' absorbance cross-section, concentration of particles in gel and solubility in the hydrogel of the bionanofluid (see FIG. 10 and FIG. 11).

Synthesis of Bionanofluid-containing Foam

Figures 12A, 12B, 12C, 12D:
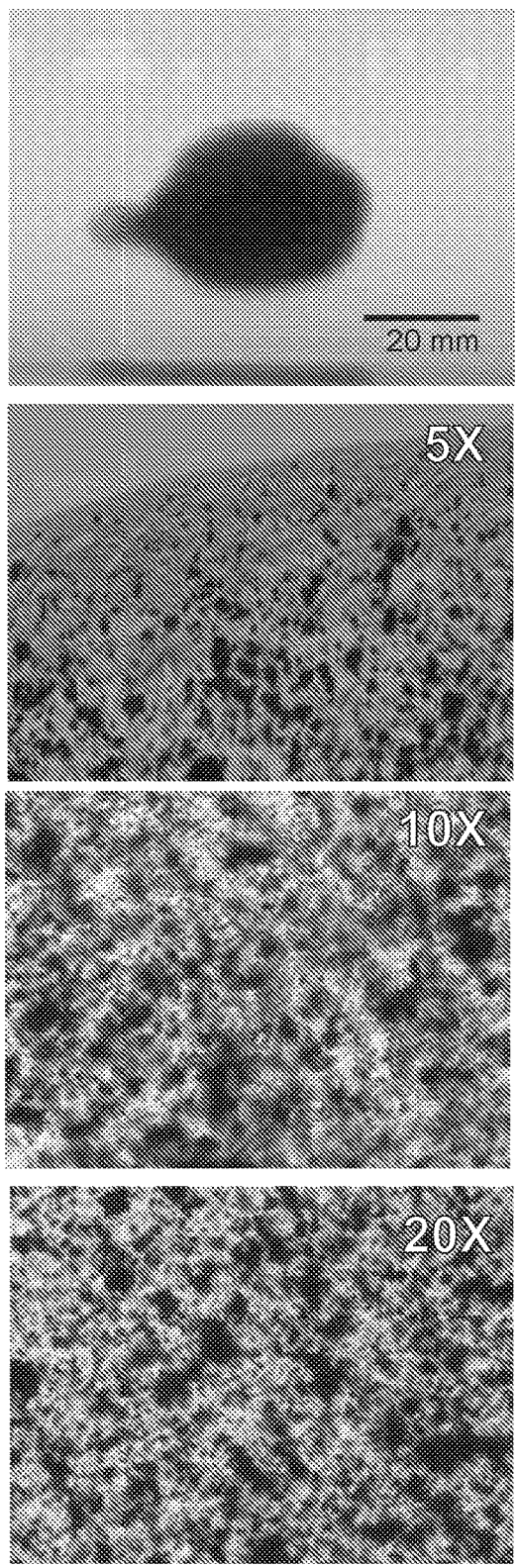

In a 25 ml flask, add 665 microliters of 28% ammonia and 80 microliters of 99% purity trimethoxysilane, 20 microliters of aminopropyltrimethoxysilane and stir vigorously. Take bionanofluid (PEGylated using maleimide amino PEGylation protocol, with any of the carbon-based nanomaterials described therein) (concentration 0.01 g/L, volume 1000 microliters) and add to stirred mixture. Add 8 mL of 100% ethanol and 5 mL MilliQ water and 0.015 grams of sodium dodecyl sulfate. Continue to mix in a closed environment (place rubber stopper on vessel to prevent evaporation). Leave for 12 hrs. The resulting foam is stable for 6 months. FIG. 12 shows images of the foam at different magnifications.

Structural Features and Geometries of the Carbon-based Nanomaterial

Figure 13A:
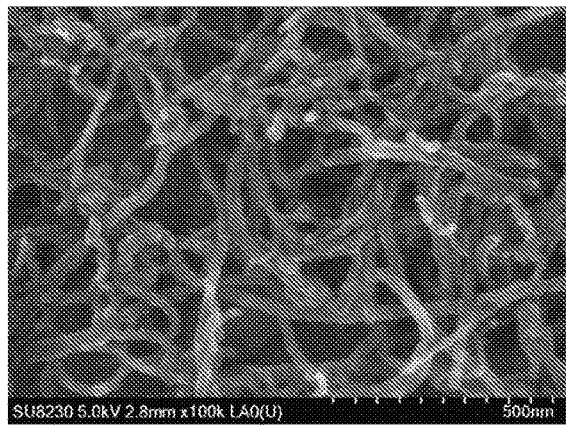
Figure 13B:
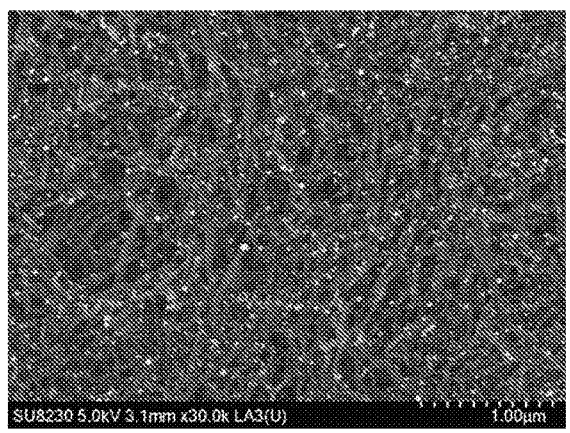
Figure 13C:
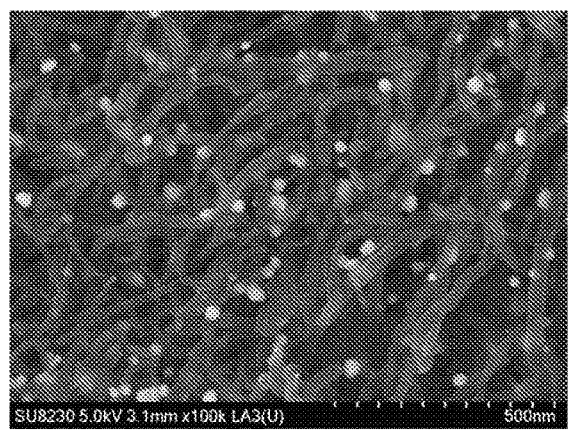
Figure 14A:
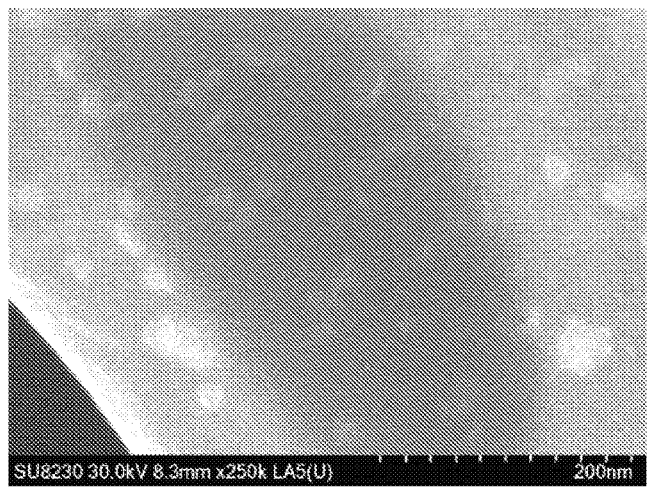
Figure 14B:
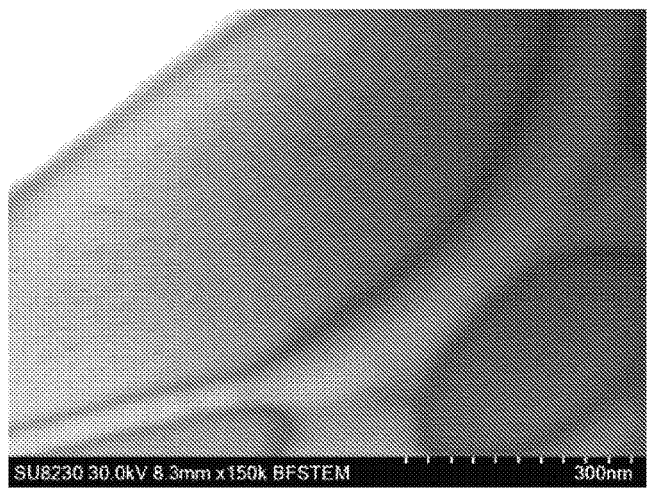

As previously mentioned, the bionanofluid can include a complex and broad distribution of structural features and geometries of the carbon-based nanomaterials. This is also evidenced in FIG. 13 and FIG. 14 representing SEM and TEM images of the carbon-based nanomaterials showing the variety of their lengths and structures.

Figure 15:
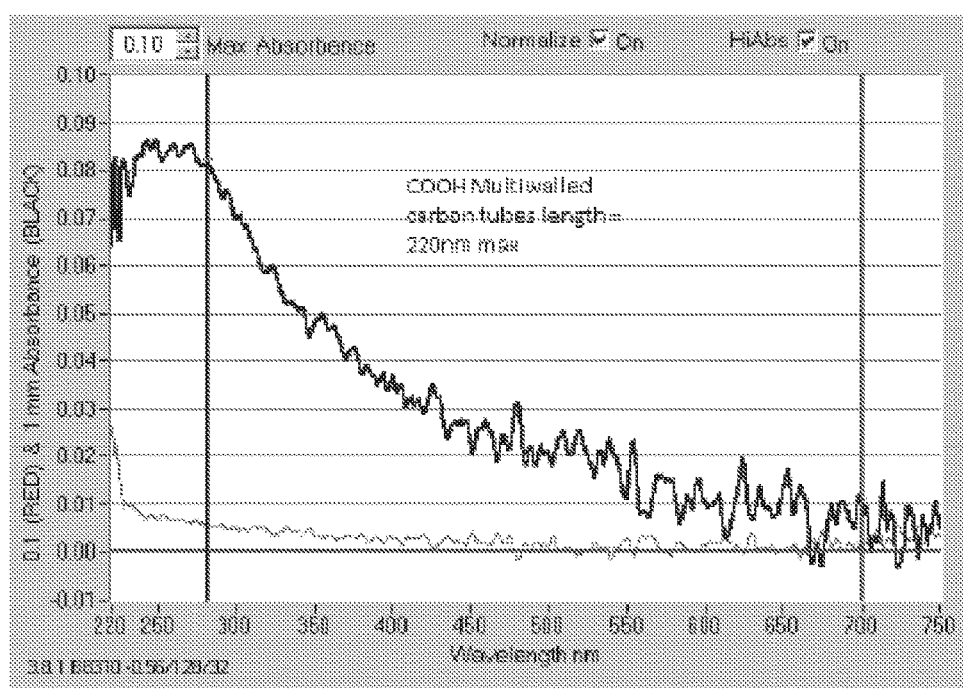

UV/VIS spectroscopy was performed to confirm optical absorbance over the UV/VIS/NIR spectrum. FIG. 15 demonstrates the persistence of absorbance over the UV/VIS/NIR spectrum. NIR measurements are limited by spectrometers sensitivity, as heating with 808 nm laser source has proved as effective as visible sources in heat generation. Size tailoring to below 0.22 micron does not affect the broad band absorbance of the bionanofluid.

Figure 16:
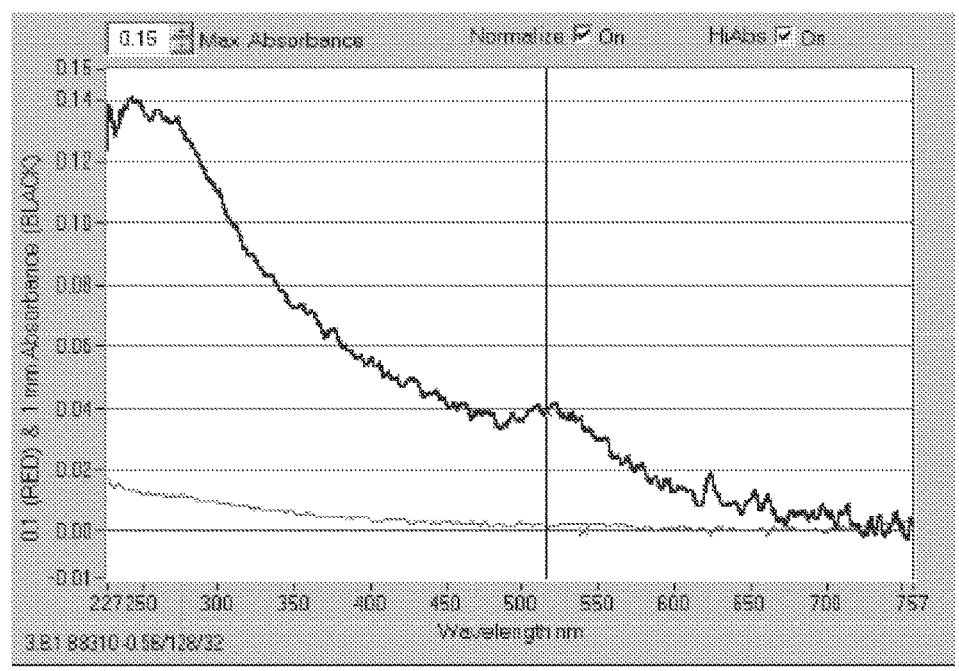

To enhance wavelength absorbance at specific wavelengths, the bionanofluids can be converted into hybrid entities through wet chemical modification with controlled growth of noble metal particles, such as gold. This is demonstrated by FIG. 16, where in comparison with FIG. 17 an additional peak has been created in the bionanofluid spectrum, pertaining to a plasmonic resonance. The resonance is supported by the gold particles attached and grown in situ as evidence by FIG. 13B/C. In FIG. 13B/C the gold nanoparticles are shown on the carbon-based nanomaterial and have clear defined spherical shape.

Figure 17:
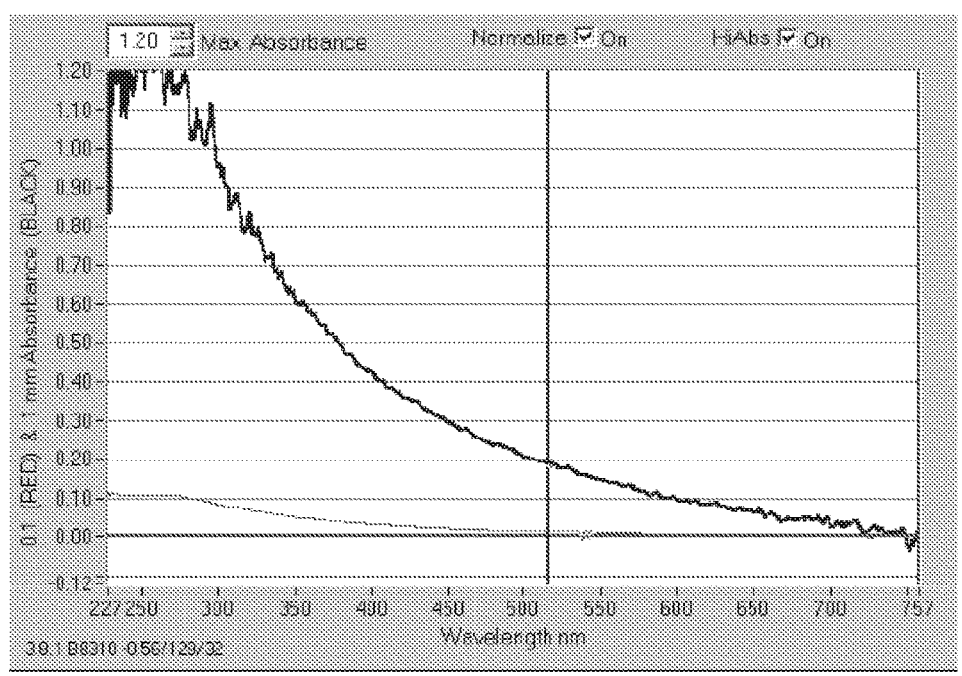

FIG. 17 shows the UV/VIS/NIR spectrum of a filtered bionanofluid including —COOH functionalized carbon-based nanomaterial. Filtration does not affect the absorbance spectrum. Large particles above 2 micron are excluded. Size range can be restricted by lowering the upper limit of the filter to 1 micron and below. Dialysis options based on molecular weight can also be applied. Both are more practical solutions that gradient centrifugation.

Figure 18A:
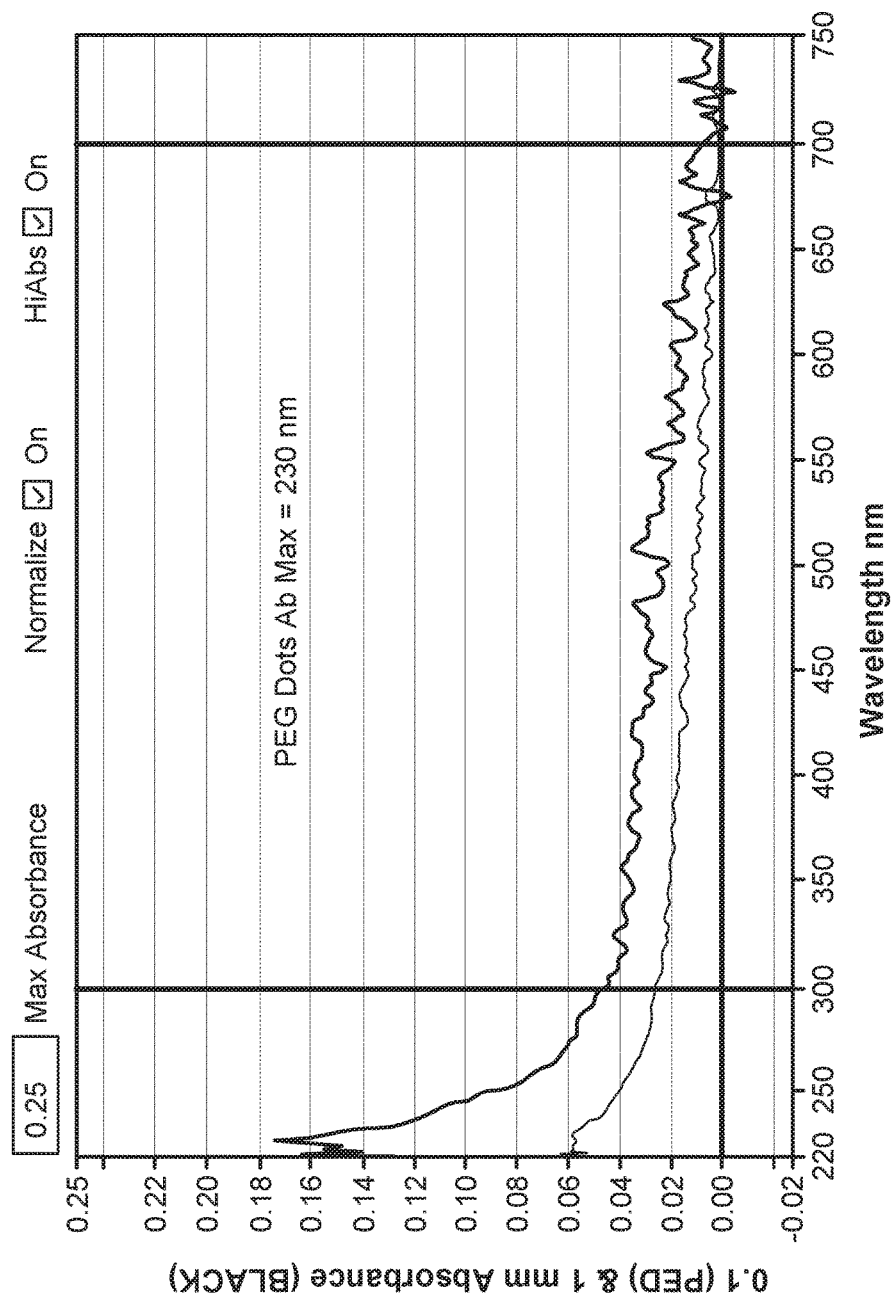
Figure 18B:
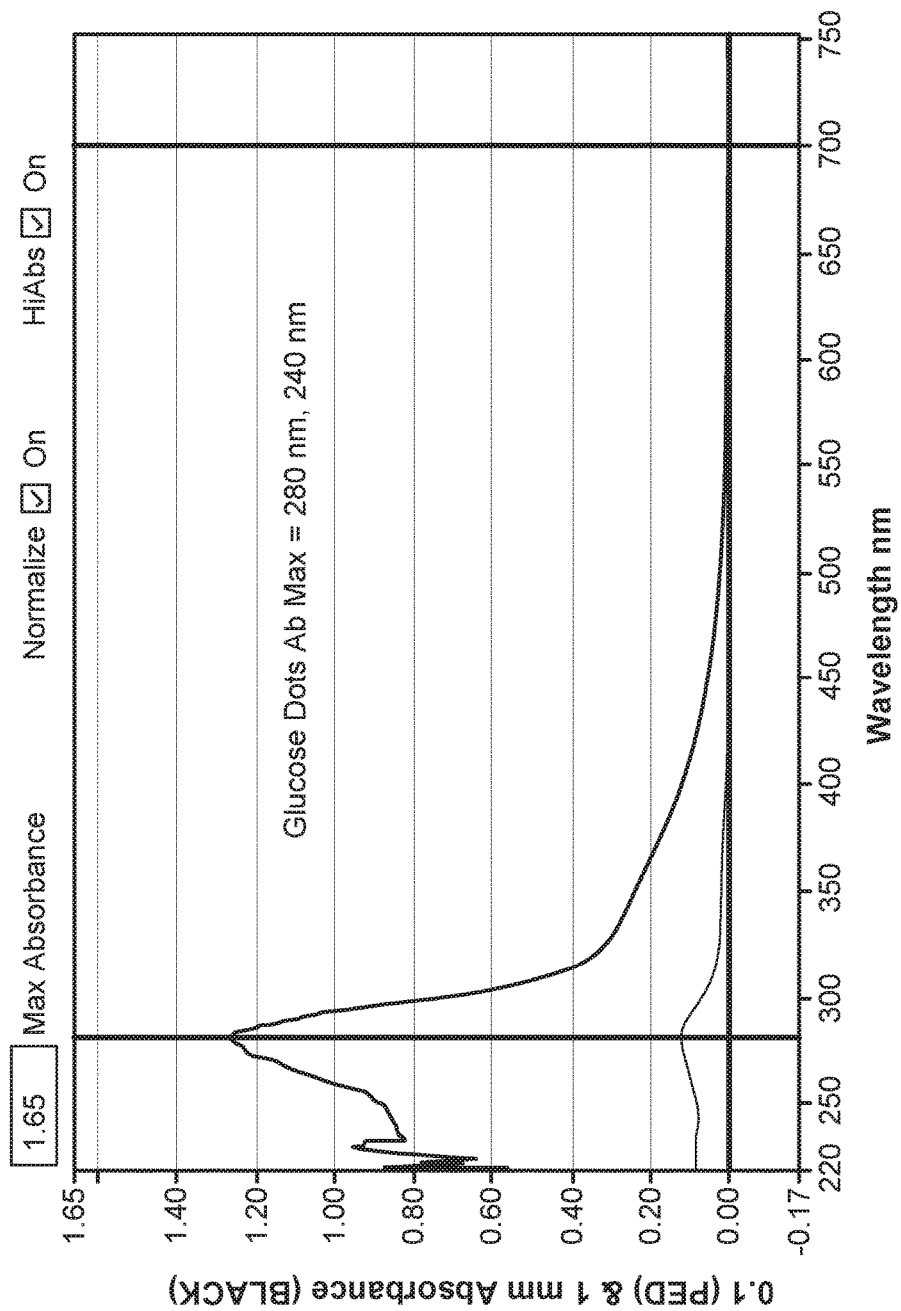
Figure 18C:
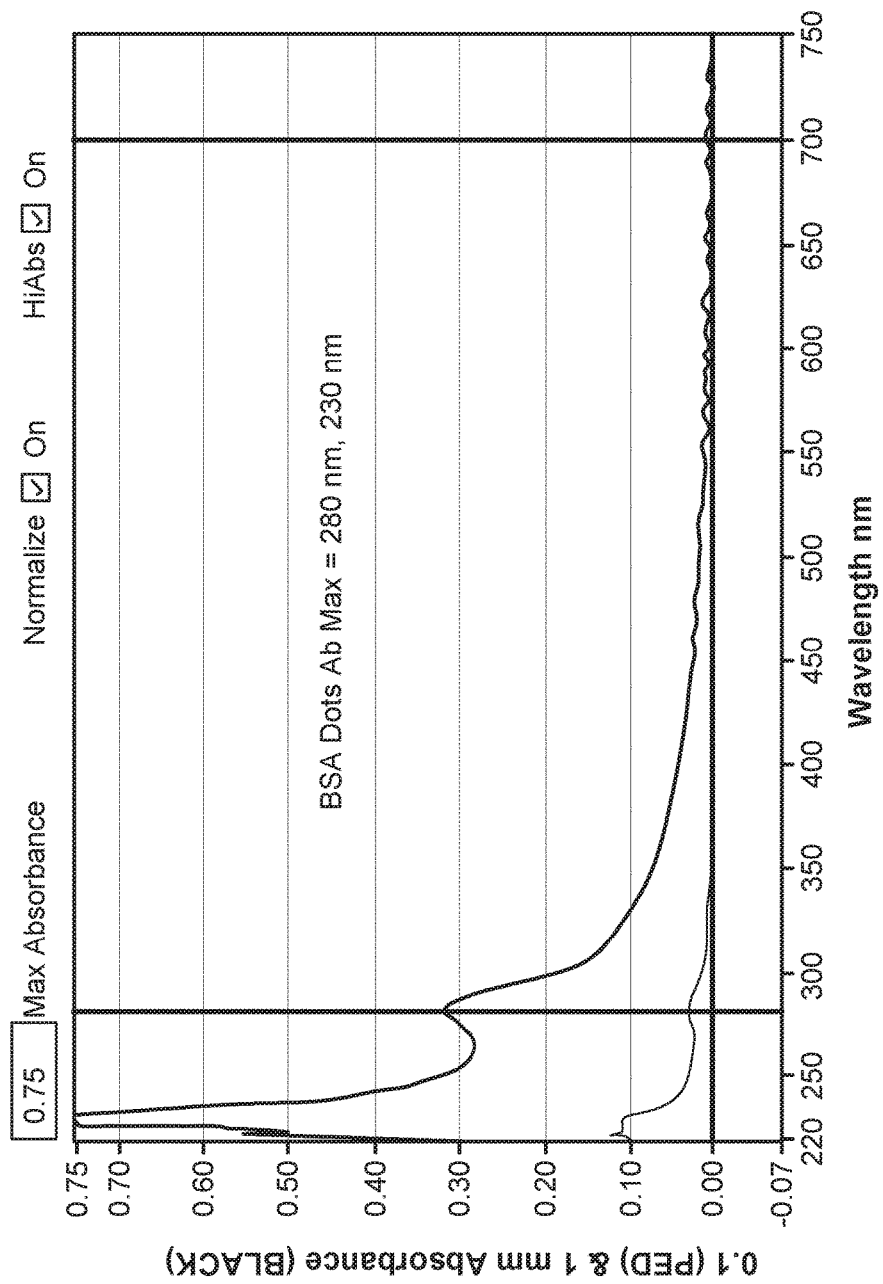

Carbon Dots are an attractive green chemistry synthesized formulation of the bionanofluid concept, where excitation wavelength is matched to a red shifting emission (FIG. 18). The higher the wavelength the further the emission moves into the red portion of the spectrum. UV/VIS spectrums are shown for carbon dots synthesised from PEG, glucose and BSA precursors. Each has different main peaks in the UV portion of the spectrum with a tail extending into the visible.

Figure 19:
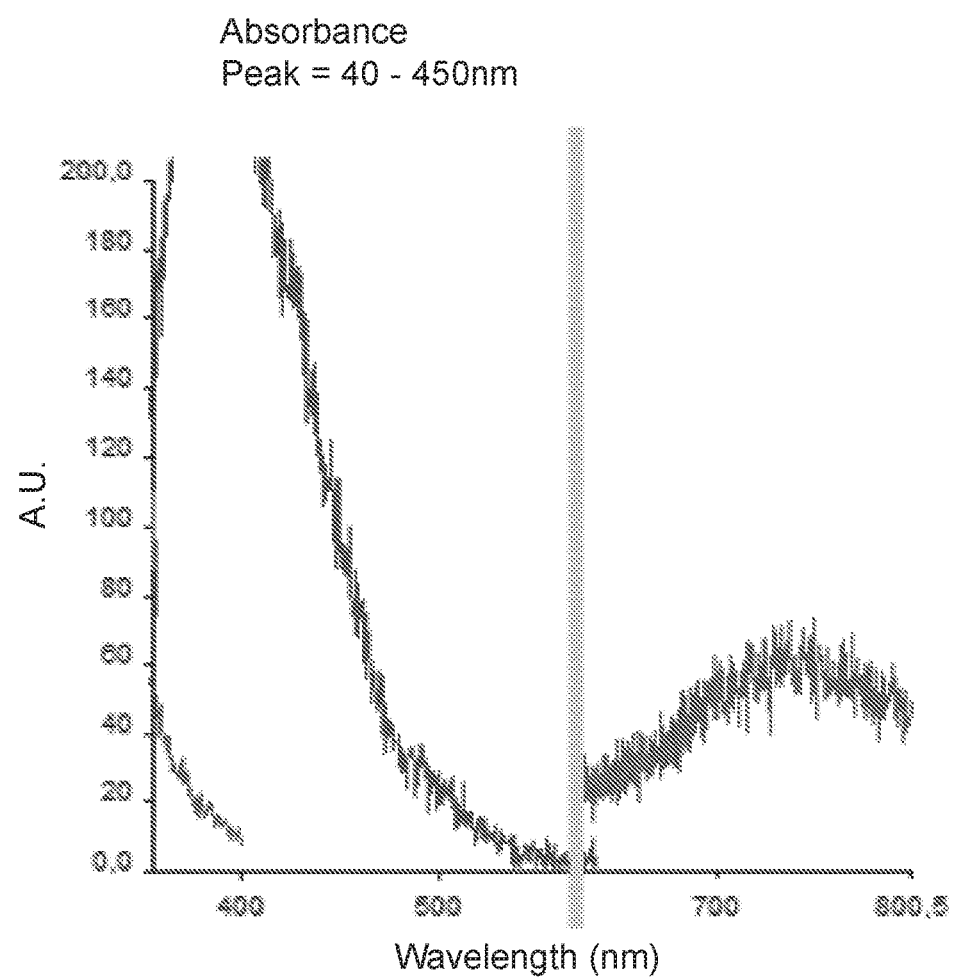

To illustrate the red shift of the carbon dots, the BSA dots were excited at 450 nm and a NIR emission was recorded at 740 nm (FIG. 19).

Ultrasound Imaging

In another embodiment, the bionanofluid is used as a contrast agent for ultrasound imaging.

A suitable contrast agent for ultrasound imaging should oscillate strongly in response to acoustic waves. The bionanofluid can support harmonic vibrations. In particular, the multi-wall variety may have a great number of possible vibrational modes due to oscillations in inner and outer walls.

It has been found that a bionanofluid having a range of geometries such as described therein provides broadband echogenicity, and can therefore be used as a contrast agent for ultrasound imaging applications.

A hypothesis is that a wide range of lengths and diameters confers a broadband interactivity with acoustic waves used for imaging purposes and thus supports various harmonic modes that relate to the acoustic properties of the bionanofluid. Another hypothesis that could explain the improved echogenic properties of the bionanofluid could be the shape range of the graphitic walls of the bionanofluid. As mentioned therein, different bionanofluid structures are produced when growing the nanotubes including, for example, straight carbon nanotubes, bamboo-type carbon nanotubes, waved carbon nanotubes, coiled carbon nanotubes, hybrid particles and branched carbon nanotubes. It may be possible that this range of shapes plays a role in making the tubes more echogenic.

Another aspect of the bionanofluid that enables their use as contrast agent for ultrasound imaging is their ability to be functionalized. As explained therein, functionalization of the bionanofluid can provide for their binding to target cells. The bio-functionalized bionanofluid can therefore be directed to intended tissues via bio-distribution, and also contribute to slowing the rate of excretion from the body. Advantageously, ultrasound imaging using the bionanofluid as contrast agent can be performed using standard equipment and methodology.

Figure 20A:
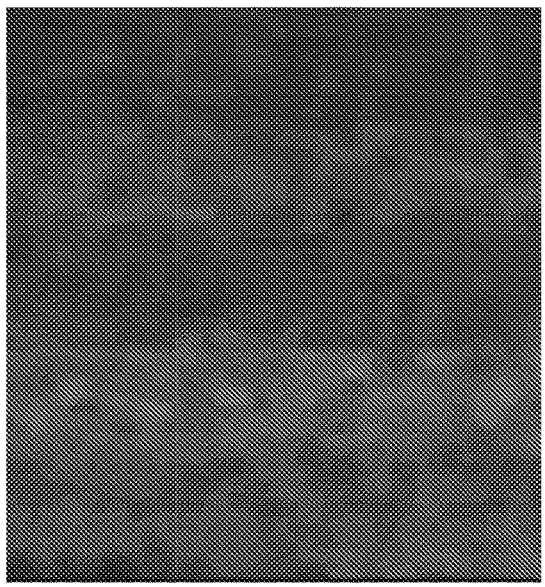
Figure 20B:
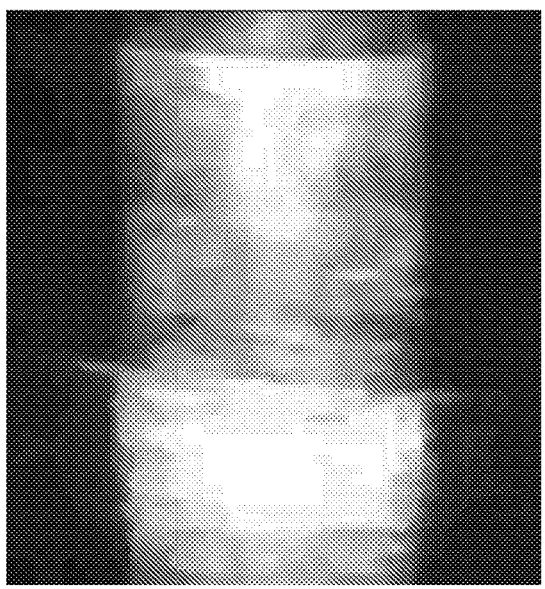

A first demonstration of the effectiveness of the bionanofluid as an ultrasound contrast agent was made at an ultrasound frequency of about 3 MHz, using a commercial ultrasound imager from General Electric (GE) commonly used for investigating internal organs of humans. FIG. 20 compares the obtained image of the same vessel with the bionanofluid (FIG. 20B) and without the bionanofluid (FIG. 20A). The contrast is very clearly visible.

Figure 21:
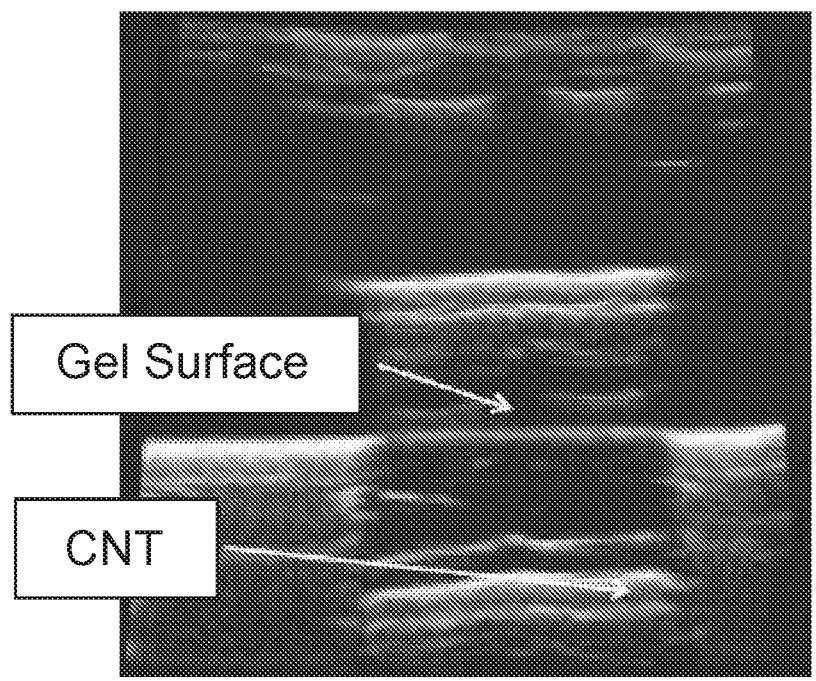

Preliminary trial experiments to test the bionanofluid response to acoustic waves were performed. An agarose gel is used to encase the bionanofluid and imaging was attempted at different probe frequencies (30, 40, 55 MHz). FIG. 21 shows the results at 30 MHz taken from above the plane of the gel surface. The image label shows the gel surface and positions. The reflections caused by the interaction with the nanomaterials above the plane of the gel can be noted.

Figure 22A:
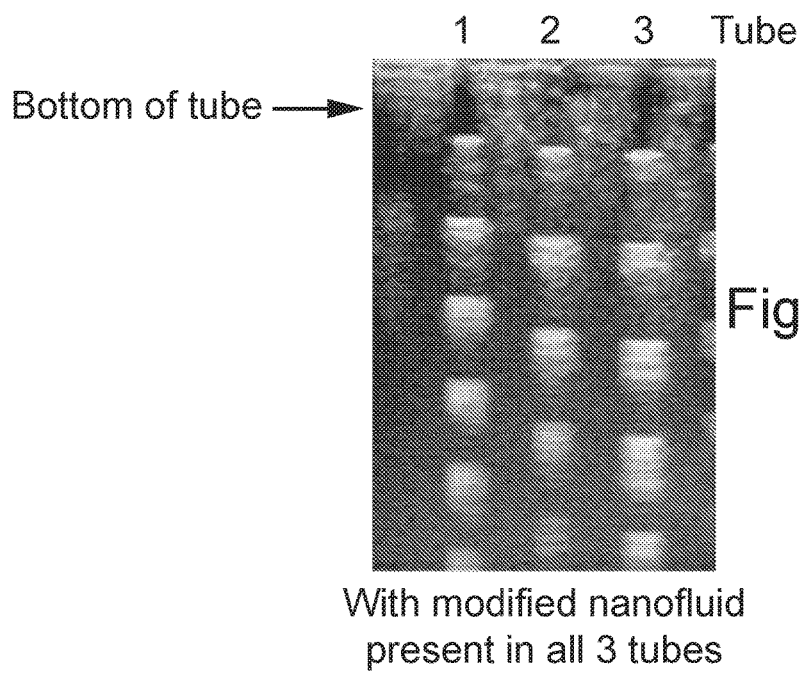
Figure 22B:
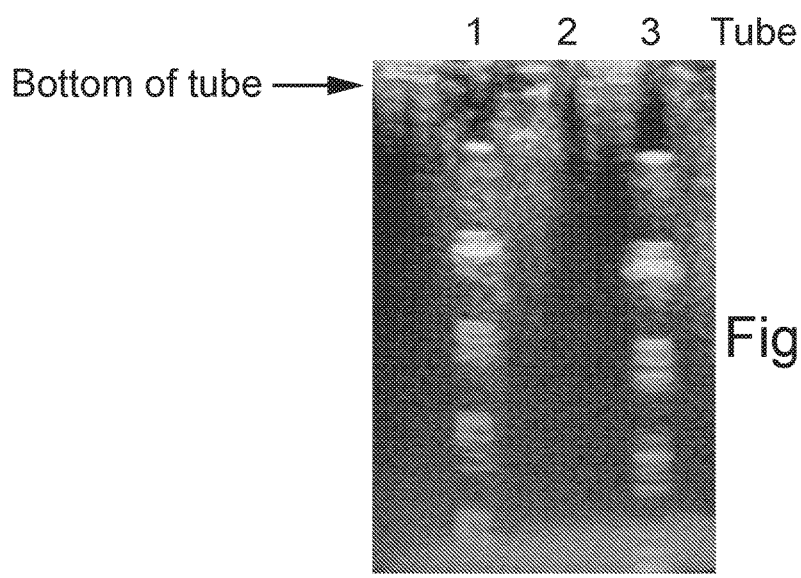

This work was also supported by an investigation with lower frequency ultrasound with harmonic capacity at 10 and 12 MHz. In moving to lower frequency, greater penetration depth means sacrificing spatial resolution of the higher frequency systems. An advantage of lower frequencies is that it moves near to suggested first harmonic resonances of around 1-5 MHz, reflecting greater signal. Harmonics of these resonances are also considered alternative measurement ranges. Imaging of the contrast at 12 MHz was achieved with 25 µL of bionanofluid within a 0.2 µL tube. FIG. 22 shows that the nanotubes' ends are orientated longitudinally to the probe face, covered with gel and brought into contact with the probe face. At this point the interaction at the bottom of the tube becomes clear in addition to vibrations. When the bionanofluids are removed from tube 2 no signal is seen, demonstrating that tubes are not contributing to the image and the contrast is purely a function of the bionanofluid interaction with the ultrasound.

Figure 23:
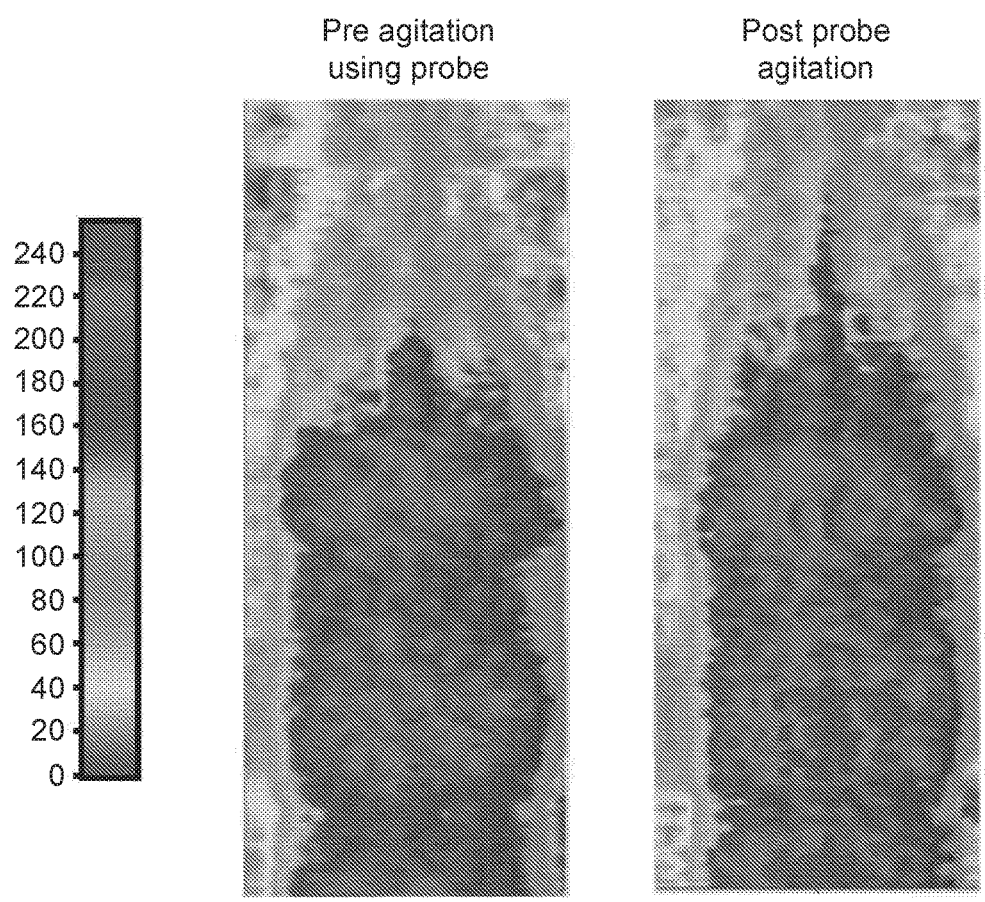

The bionanofluid in a tube can be agitated by the non-contact movement of the ultrasonic probe. FIG. 23 shows the agitation of the bionanofluid with an ultrasonic probe. In this demonstrative image, the black and white ultrasound image has been transposed into false color to show intensity of acoustic reflected signal from the echogenic bionanofluid. The image was taken across the glass vessel contacting the bionanofluid mimicking the dimension of a large blood vessel. Looking at the increase in the red portion of the spectra, this demonstrates firstly that the bionanofluid can be manipulated by sounds waves, but it is also highly echogenic, making it an ideal system for image contrast in cardiovascular disease, tracking of nanoparticle therapeutics and as a broad clinical tool.

Referring to FIG. 23 the potential to agitate or manipulate the bionanofluid by non-contact movement of the probe at a distance of 2-5 cm from the glass vessel they were contained in was demonstrated. To perform the measurements, the probe was moved away from the tube, moved up and down over the length of the tube (8 cm) and returned to a stable contact position. Without agitation the image had high contrast, but by creating movement in the vessel, using ultrasound non-contact agitation, the acoustic field intensity was increased due to local movement and collection of particles within the probe field, in effect inducing an oscillation. The increase in signal reflects a localized concentration returning more signal to the probe than when particles are static and in a non-moving acoustic field. The implication is that particles that collect at either organs or at points of restricted blood flow such as in arthrosclerosis. The modification with biomolecules and ligands extends the sensitivity of bionanofluids as sono-acoustic particles that are sensitive to ultrasound. The inventors demonstrate here the ability to further cause motion through the interaction of the probes acoustic emission without direct contact with the bionanofluid or container. Post agitation increases are observed in the red and purple regions denoting increased intensity in the profile image taken at 12 MHz and with harmonic enhancement using the GE Ultrasound machine.

The investigation of ultrasound contrast enhancement by bionanofluid aids the imaging of prostate morphology (as well as other hard tissues or organs to define structures by ultrasound) and structure within mice, and has wider applications in ultrasound-guided investigations in larger animals and, ultimately, humans. The first step is to determine with mouse studies the ideal concentrations and effect of flow rates upon ability to image (see FIGS. 24, 25, 26, 27). It is clear at lower frequencies nearer the 1-5 MHz acoustic resonance of the bionanofluid that interaction with acoustic waves is stronger.

Figure 24A:
Figure 24B:
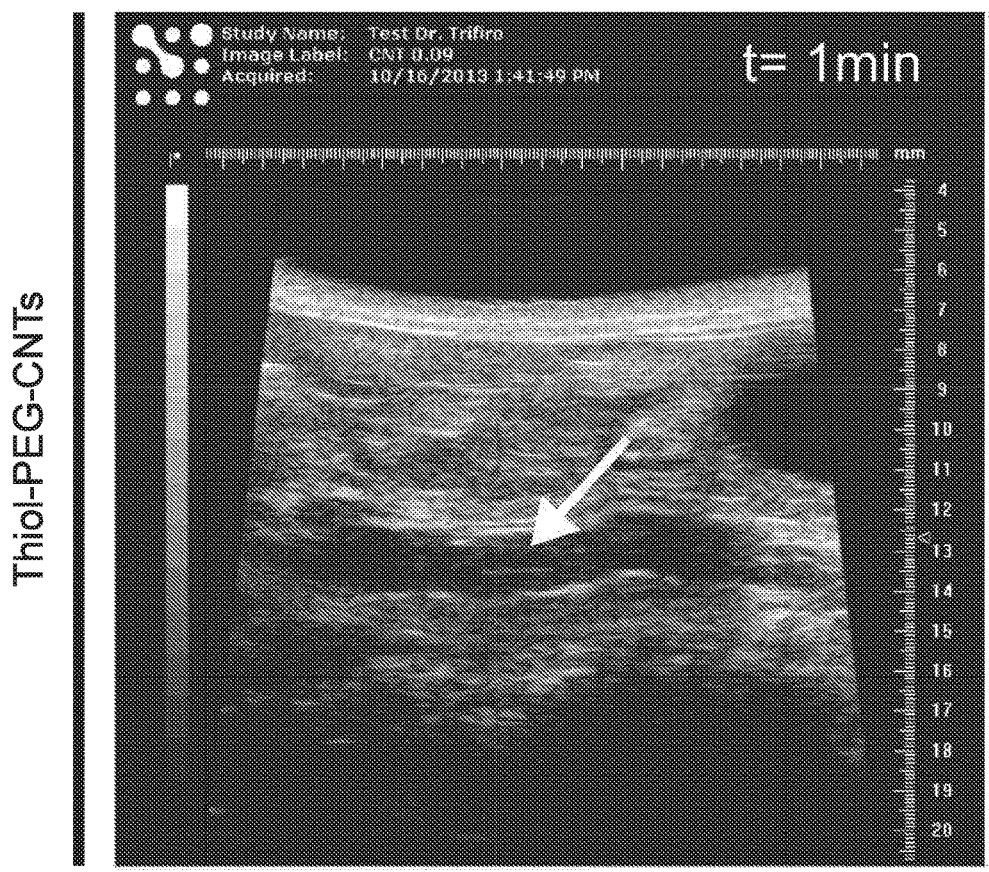
Figure 24C:
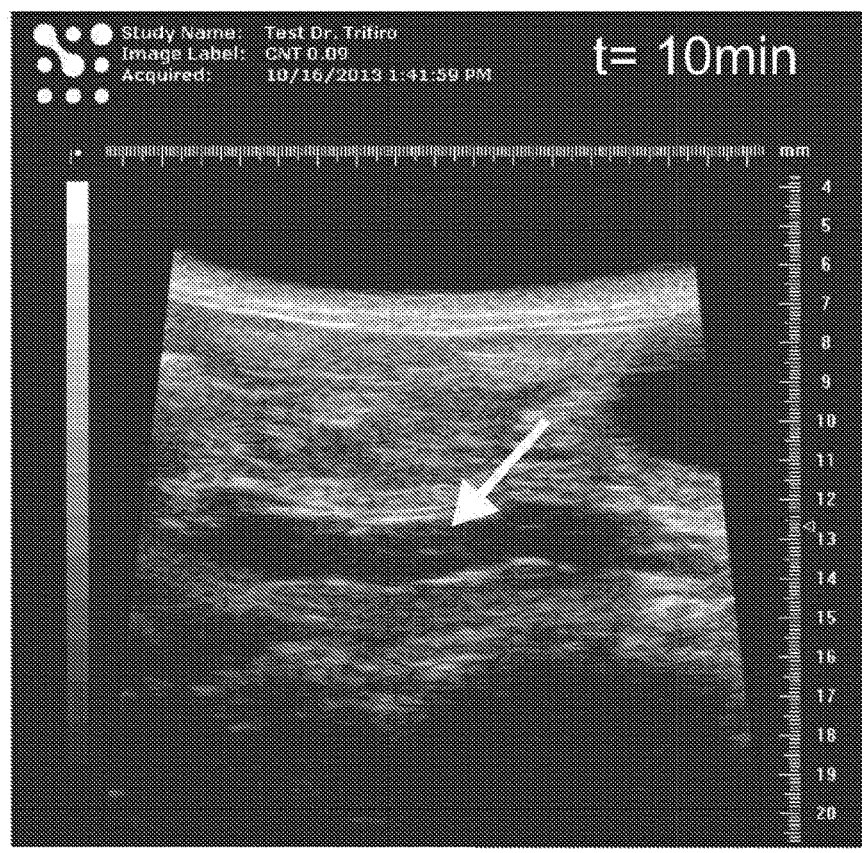

Studies using ultrasound experiments were conducted with intravenous injection to the tail vein of a mouse. The ultrasonic probe was position and above the longitudinal axis of the vena cava prior to injection (FIG. 24). A saline injection of 200 microliters was performed and no change in reflection, hence contrast was observed within the vessel. When the bionanofluid (carbon derived and modified for biocompatibility) was injected reflections within the blood flow become apparent with the vessel (indicated by arrows on FIG. 24). Biomodification of base materials for bionanofluids is essential as dispersion has to be achieved within blood (red blood cells and plasma), unmodified carbon tubes lacking bio-compatibility cannot be used and will aggregate in solution. This is a specific claim of bionanofluids that they must be bio-compatible to elicit function in vivo, failure to modify is not a bionanofluid.

Figure 25A:
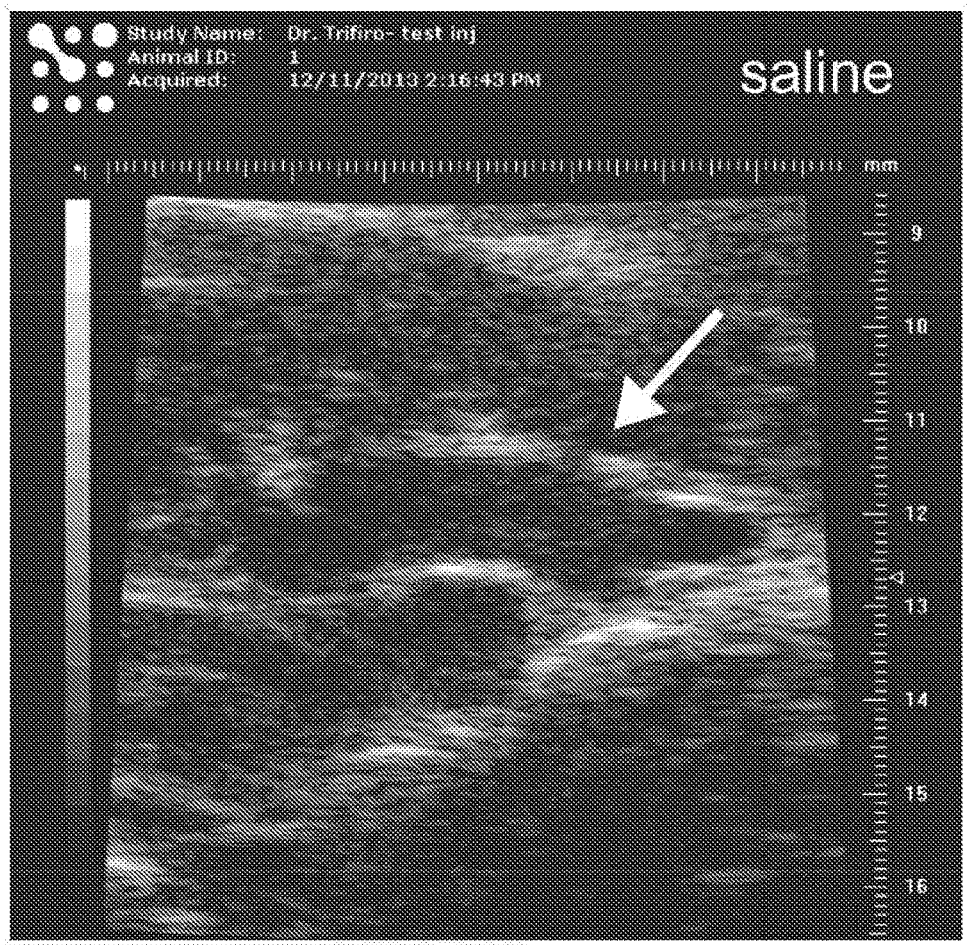
Figure 25B:
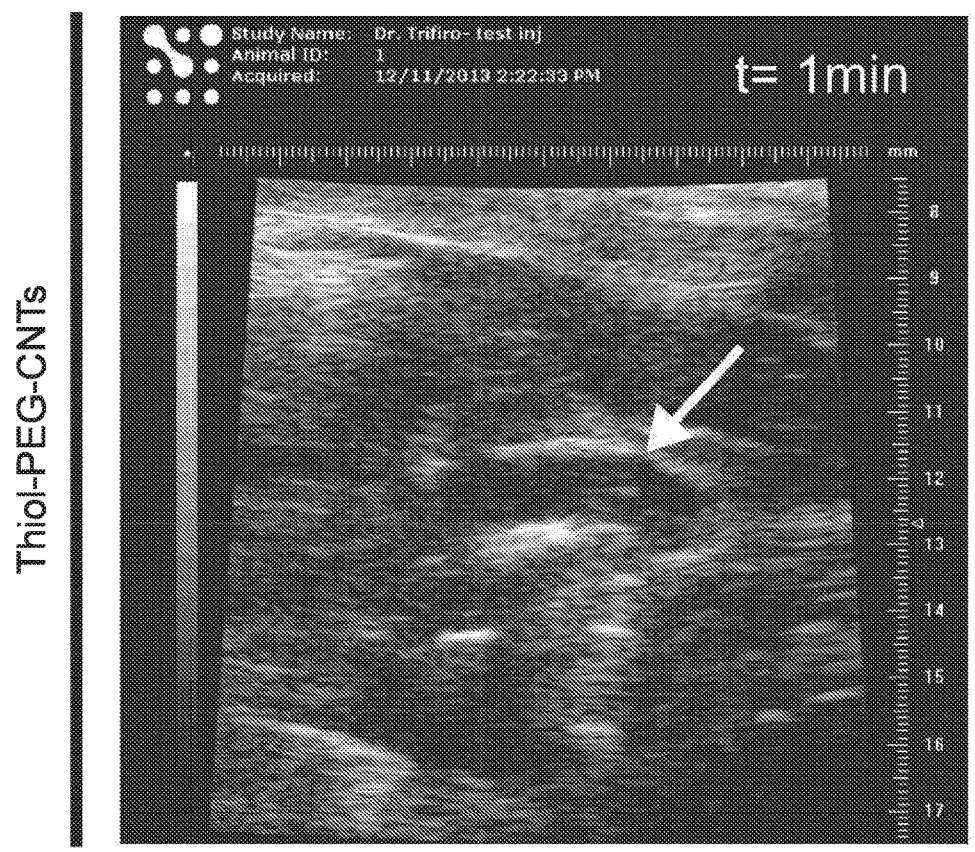
Figure 25C:
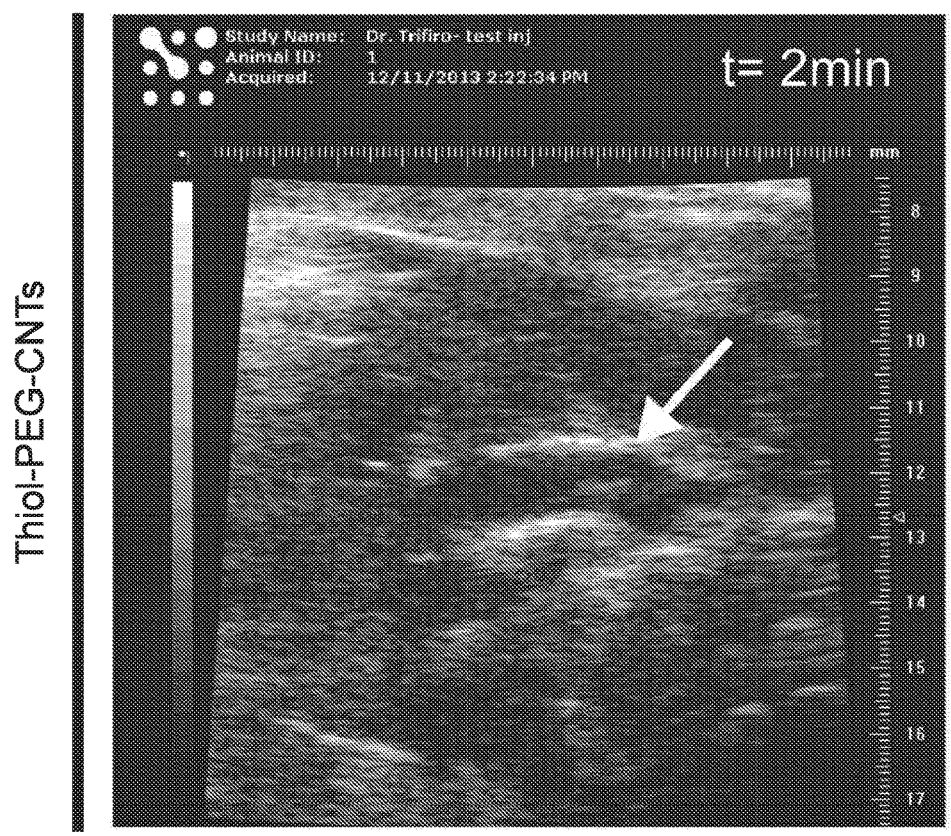
Figure 26A:
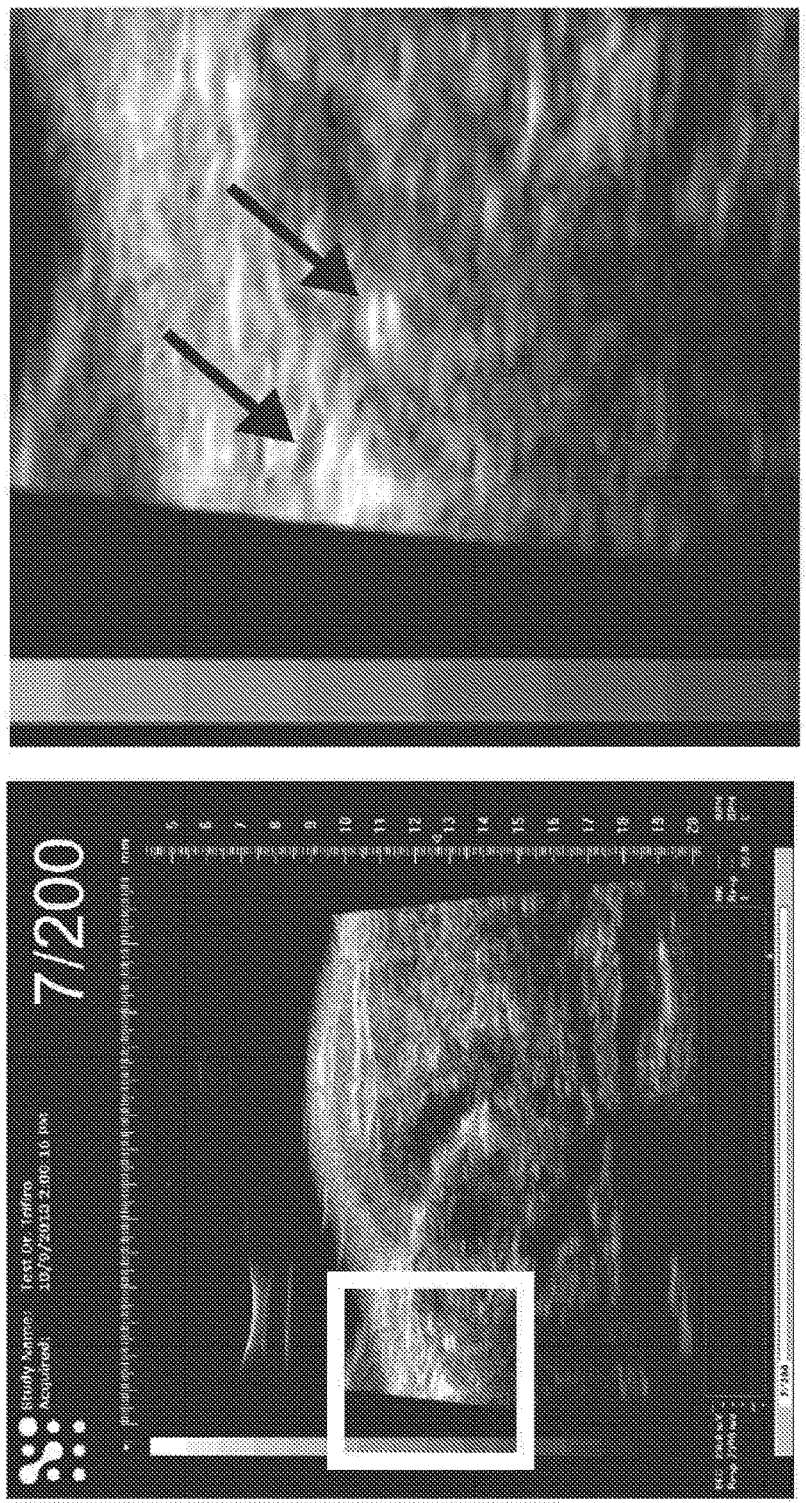
Figure 26B:
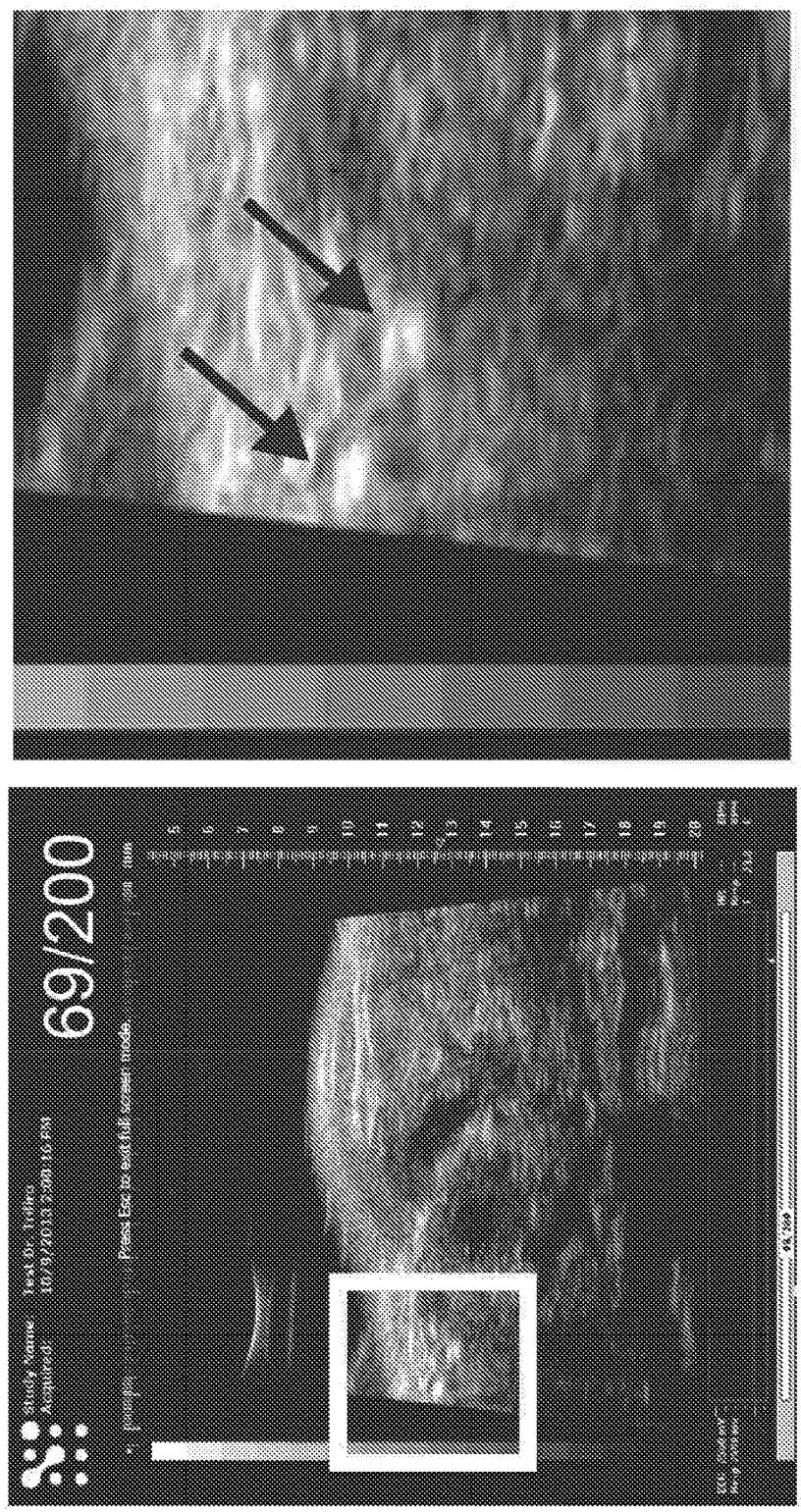
Figure 26C:
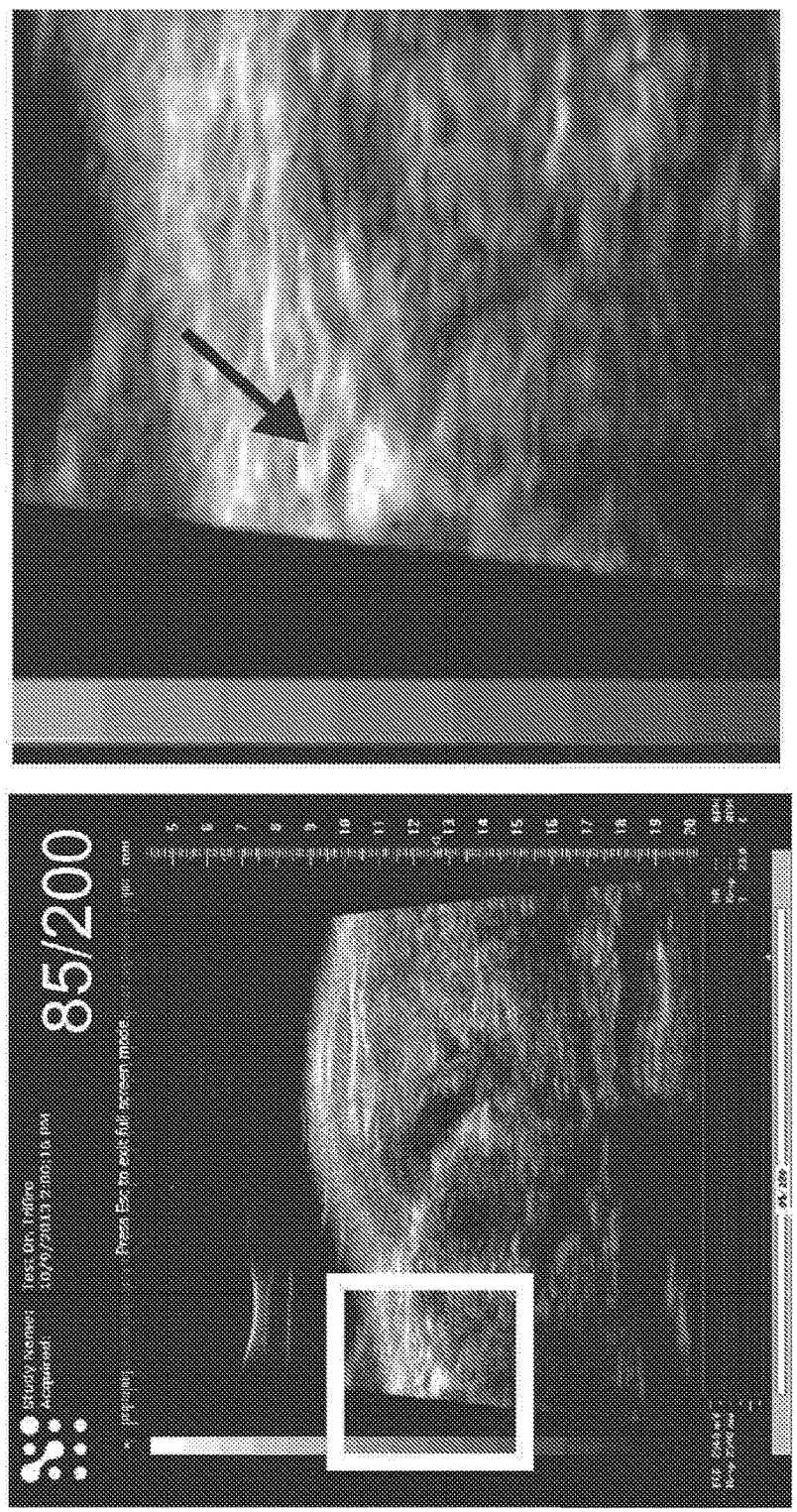
Figure 26D:
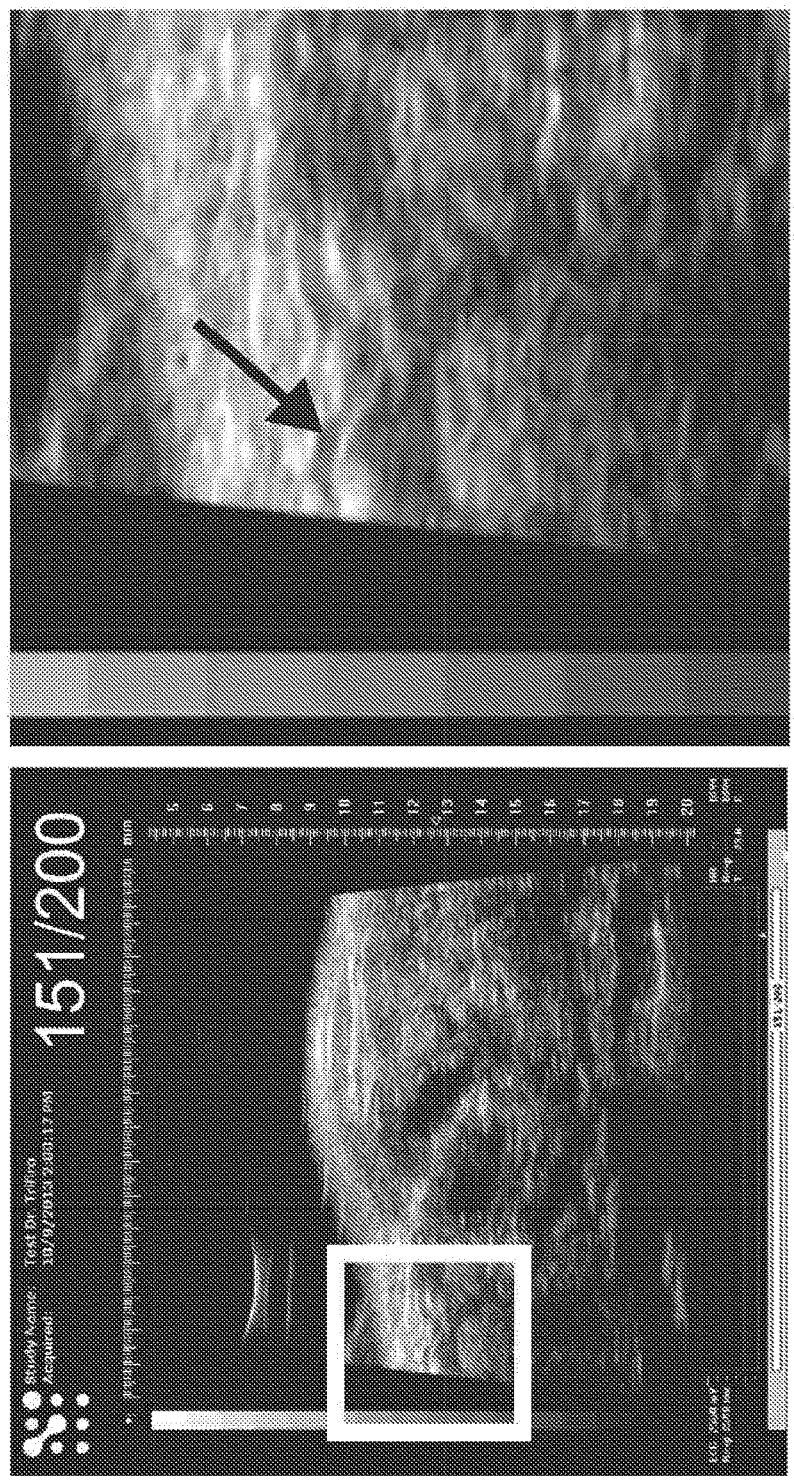

Further experiments to investigate circulation of the carbon derived bionanofluids were performed using injection into the jugular vein, through a stent (FIG. 25). The purpose was to study the progress of the bionanofluid with the circulatory system and observe its passage through the heart's major chambers before exiting through the aortic arch. The bionanofluid loaded blood stream must pass through the jugular vein, right atrium and right ventricle before exiting through the pulmonary arteries to the lungs. The injection then has to return to the heart before exiting the left atrium and ventricle through the aorta. The aortic arch is branched and represents a complex flow system. To firstly deliver the bionanofluid loaded blood to the arch involves interaction with two major organs and large blood vessels, in FIG. 25 the absence of injection is seen in the furthest left image (aortic arch indicated by arrow). The passage of the injection is shown in the following images, again by increased reflective contrast caused by the bionanofluid dispersed in the blood stream.

Injections of the bionanofluid were also studied by direct injection through the mouse bladder (FIG. 26). Injection was made into the urine and the flow out of the urethra observed. FIG. 30 enlarges the section where the bionanofluid passes through with the urine.

Studies were continued with consideration of smaller vessels. A needle was introduced to the kidney, such that ultrafiltration of the bionanofluid could be considered (FIG. 27). Careful size modification of the carbon derived bionanofluid differentiates it from base nanofluid both by length, diameter and bio-compatibility. Size modification relates to filtration and dialysis treatments to tailor size. As stated previously size ranges have different biological impacts and size range relates to area/targeted region of application. Specifically for tumour perfusion below 0.22 micron, for external surface of tumour retention 0.22 to 1 micron is favoured and for external/topic treatments such as for gel/foams where no issues of perfusion, or circulation within the blood stream is not required. Further, longer fibrils of any material are known to cause fibrosis and general skin irritation. Any nanomaterial preparation, liquid, solid, composite or otherwise, is carefully designed paying attention to size and geometry. In the bionanofluid formulation for cancer treatments, size is tailored to avoid short rigid tubules that can puncture cells, analogous to transfection by electrophoresis. Tubes that are too long are also avoided, as they can induce non-specific mechanical abrasive effects leading to cell death. Consideration is given to evidencing the benefit of this approach in control experiments of FIGS. 28, 29, 30, 31, 32, 33, 34, 35, 36, 37, 38, 39, 40, 41, 42, 43 and FIG. 44. Where controls are applied, the modification performed to avoid non-specific adsorption also protect against mechanical abrasive damage by prevent cell adhesion. If size related cell damage was present, these controls would show significantly worse cell death, the opposite is true where retention of bionanofluids is so slow, longer laser exposure times (FIGS. 32, 36 and FIG. 40) have to be applied to limit damage to cell numbers reflecting very low non-specific retention and mechanical damage. The bionanofluid is seen exiting the tip of the needle before re-concentrating post ultrafiltration in the kidney vein with the solution moving above and to the top right of the image.

It will therefore be readily understood by one skilled in the art that the bionanofluid can be used as a contrast agent for a variety of ultrasound imaging applications, at a wide range of frequencies and that biomolecule-driven adhesion/retention at site of relevance to the practitioner will increase the echogenic effect.

Therapeutic Applications

In accordance with another aspect, a bionanofluid as described therein can further be used in the destruction of targeted entities, preferably biological entities such as prokaryotes or eukaryotes, preferably, organs, tissues, bacteria, viruses, fungi or cells such as cancer cells. This application is not limited to cancer but includes other human cellular diseases and/or infections.

In one embodiment, cancer serves as an application specific tool. Generally speaking, the challenges for developing a cancer treatment include: (1) preparing a therapeutic agent as a stabilized and dispersed bionanofluid; (2) imaging to follow the therapeutic agent; (3) reaching the target (tissue perfusion, biodistribution, solubility and retention in plasma) such as cancer cells; and (4) killing this target (immediately or initiating the process of apoptosis).

With respect to the preparation of a bionanofluid therapeutic agent, the challenges to overcome are: (1) stabilizing the nanoparticles, which tend to agglomerate due to their high surface area and the large Van der Waals forces present between the particles, while balancing excess negative and positive surface charges that can lead to dipole:dipole association with biomolecules in an uncontrolled nonspecific way; (2) using fabrication methods which will not degrade the particles and thus destroy the property which is desired for the bionanofluid. One skilled in the art will readily understand that the preparation of a bionanofluid such as explained therein can readily meet these requirements.

With respect to imaging, as explained therein, only microbubbles are currently used to image blood flow using ultrasound. However, presence of microbubbles is detrimental to patient health, resulting in head pain, nausea and other side effects in a significant number of patients. This provides an incentive to avoid their use from a clinical prospective. The bionanofluid described herein represents an interesting alternative tool.

In some embodiments, because with declining or lower sound frequencies the interaction with the bionanofluid becomes greatly increased based on observations documented herein, it is proposed that HIFU (High Intensity Focused Ultrasound) will be greatly enhanced on a local scale by the presence of particles that will oscillate on a nanoscale, causing acoustic-mechanical damage to cells to which they have been targeted by surface modification.

With respect to reaching the target, the Applicants have found that modifications of the bionanofluid as described therein are useful for directing the bionanofluid to specific tissues via bio-distribution, but also in slowing the rate of excretion from the body. In addition, the potential to image blood is advanced by the presence of the bionanofluid within the flow, coupled with a greater persistence in the blood, reflecting modifications.

The bionanofluid conjugated with antibodies/short peptides/small drug molecules present a platform where quantitative accumulation can be measured by portable ultrasound machines, and treatment initiated.

When developing bionanofluids for heat absorption, the bionanofluid, as well as carbon nanotubes (CNTs) in general, offer a great advantage by being high absorbers of heat and having great thermal conductivity. The inventors found that the bionanofluid described herein could be used as a photothermal agent for cancer treatments, by heating and killing cells, such as cancer cells.

Light from a laser beam at a suitable wavelength and power is absorbed at the surface of the bionanofluid, transitioning electrons to an excited, higher energy state. As the electron relaxes from an excited state, returning to the ground state, a predominantly non-radiative transfer takes place. It has been found that the process is mainly non-radiative as the emission of a photon through photoluminescence in carbon nanotubes occurs at a lower quantum efficiency at UV/Vis and increases with near IR and more so at telecommunication wavelengths. The energy is therefore emitted as heat, which relates directly to a temperature increase at the surface of the carbon nanotube. Heat is then dispersed by conduction when in contact with cells and by convention to the solution.

Two methods using the photothermal conversion of laser light to heat can cause cell death.

The first method is the ablative bulk heating method. The second method is the localized nanoscale heating of the bionanofluid in contact with or adhering to cells through an antibody or other cell specific ligands and delivering high temperatures (between 45° C. and 200° C.) to cell membranes causing lethal damage through heat denaturation of cellular components (lipids, proteins).

Ablative Bulk Heating Method

In this variant, ablative killing relies on the bulk heating of a tissue. Ablative treatment in clinical fields requires a high powered laser that heats the tissue, causing wide spread damage to include adjacent non-cancerous tissue. To aid the process and reduce power, nanoparticle mediators that couple light into heat are used to produce more local effects. The bionanofluid can be effectively used to achieve this. In the demonstration here, the effect of laser exposure time with the bionanofluid present and after 20 seconds showing complete cell death is presented (FIG. 28). Ablative killing relies upon having a high concentration of the bionanofluid in the bulk solution or tissue.

Experiments were carried out using both a near-infrared laser source at 808 nm and a 532 nm laser source, to initiate the photothermal effect. Time in the tables refers to exposure time with a 2.7 W 532 nm laser, while 808 nm laser could also be used. It will however be readily understood that other wavelengths can be used without departing from the scope of the invention.

Before evaluating the bionanofluid on cancer cells, experiments were performed on various cell lines, such as Human Embryonic Kidney Cells, such as HEK 293 cells.

FIG. 28 shows the effect of short exposures of the bionanofluid:HEK 293 cells to the laser light. The result is rapid cell death; after 20 seconds, the cells are all dead. FIG. 29 and FIG. 30 shows the obvious qualitative differences in cell numbers between HEK 293 cell suspensions in the presence of the bionanofluids after different exposure lengths (5, 10 and 20 seconds) to the laser (2.7 W). Few cells are evident at exposure time of 20 seconds and these remaining cells are necrotic. To more accurately quantify the effect of exposure, cell counting was employed in combination with the trypan blue cell viability method in FIG. 29.

In FIG. 29, "Blue" refers to necrotic/dead cells that internalized trypan blue and are stained blue; and "White" refers to non-necrotic/live cells that did not internalize methylene blue and remained white. Dead cells are not observed as no colour change can be determined. Conversion of cells counted by haemocytometer to reflect cell culture concentration: average # cells×dilution (×2)× $10^4$=cells per mL.

Cell death calculation via haemocytometer involves sampling two squares from each repeat sample at 3 different exposure times, at a constant optical power of 2.7 W. Controls showed no blue cells, hence no cell necrosis or death. Averages for blue and white counted cells are produced and used to calculate cells of each possible state (dead/uncountable, necrotic and live). FIG. 30 shows the cell concentrations for each exposure time and condition. Dead or uncountable cells are calculated as the remaining fraction of the starting quantity (650,000 cells per mL).

A clear trend develops indicating that cell death increased, as does necrotic cell count, with increased exposure time. The inversion of the initial white to blue cell ratio reflects the relationship between exposure time and cell death. Cell non-viability extends to the point where so the few cells are left unlysed, with few intact necrotic cells remaining.

To compare between cell lines, breast cancer cells were trialled by the same approach, using HEK293 as a control. Again all cells were sent into at least a necrotic non-viable state or destroyed.

Blue denotes necrotic and white is dead or unidentifiable under the trypan blue viability test.

This method is consistent in cultures with different tissue culture/eukaryotic cell lines.

Directed Therapeutic Methods

Ablative bulk therapy is not appropriate in all cases and it is wise to look at localized killing methods that do not damage the healthy cells.

This approach involves confirming specificity on cells using carefully designed controls. In this approach, without modification of the bionanofluid, specificity for cell death cannot be achieved, even when the bionanofluid are present at the same concentration.

In one embodiment, thyroid cancer, prostate cancer and breast cancer were studied. Cancer application using each formulation is seen as a separate embodiment. The methods of targeting each cancer type and combination of physical and chemical treatments are unique when treated as a whole.

Thyroid cancer incidence is increasing. The current treatment consists of thyroidectomy and radio-iodine ablation, followed by thyroid hormone replacement and TSH suppression. However, there are many side effects and recurrence rates are high. TSH Receptor (TSH-R) was studied as a Target. Modifications of the carboxylic acid groups of the bionanofluid to form thioesters with modified tetrazole compounds and addition of cellular recognition through attachment of thyroid specific hormone (TSH) and TSH-R antibody have been evaluated.

Prostate cancer is the second most common cancer in men in the US. About 1 man in 6 will be diagnosed with prostate cancer during his lifetime. 60% of the patients are above 65 years of age. Treatment options are surgery, radiation therapy, hormone therapy and more. Prostate specific membrane antigen (PSMA) was studied as a target. It is situated on prostatic cells, it is a sensitive and highly specific marker for prostate cancer, and its expression correlates with cancer aggressiveness and represents an independent indicator of poor prognosis.

Selection of the targeting antibody using western blot analysis was performed. Negative and positive cell lines were determined. Antibody-conjugated carbon-derived nanotubes were prepared. Cells were incubated with the conjugated bionanofluid, followed by washes to remove non-specifically bound bionanofluid. Cells were then exposed to laser light, creating localized photothermal damage of cells. Comparison of treated and untreated cells was performed. Cell killing was completed repeatedly and with controls, while controls of experimental variables were approached systematically.

Figure 48:
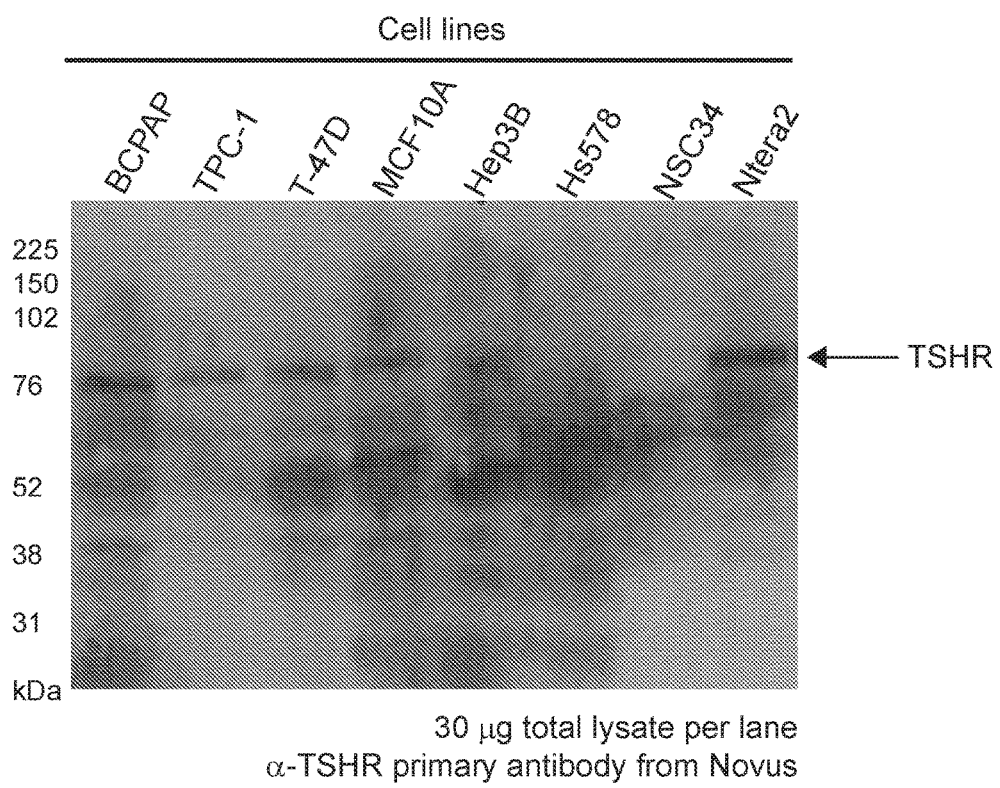

Referring to FIG. 47 and FIG. 48, antibody selection for PSMA (prostate cancer) and TSH-R (thyroid) is shown, respectively. In these Figures:

LNCaP is a human prostate adenocarcinoma cell line, derived from left supraclavicular lymph node metastasis, expressing PSMA.

TABLE 1

Trypan Blue viability test comparing HEK293 cells with MCF7 breast cancer cell line (2.7 W power, 20 second exposure, n = 4)

|  | stock | Blue | White | Blue | White | Blue | White | Blue | White |
|---|---|---|---|---|---|---|---|---|---|
| MCF7 | 12000 | 7000 | 0 | 5000 | 1000 | 4000 | 1000 | 12000 | 0 |
| HEK293 | 61000 | 8000 | 0 | 11000 | 0 | 7000 | 1000 | 7000 | 0 |

PC3 is an aggressive human prostate cancer cell line, it is a prostate adenocarcinoma cell line, derived from bone metastasis.

BCPAP is a TSH-R positive cell line, a poorly differentiated human papillary thyroid cancer cell line.

NSC-34 is a TSH-R negative cell line, an hybrid cell line derived from the fusion of mouse neuroblastoma cells with mouse motor neuron spinal cord cells.

TPC-1 is a human thyroid tumour cell line.

T47D is a human ductal breast epithelial cell line.

MCF10A is a human breast cancer cell line.

Hep38 is a human hepato cell line.

HS578 is a human pancreatic cancer cell line.

Ntera2 is a human neuronal cancer cell line.

Selection was optimized by western blot analysis against the available cell lines. Antibody and protein mass were carefully analyzed to confirm the correct target molecule was being selected for. Laser treatment was optimized with respect to exposure time, conjugate ratio and protein loading.

FIGS. 31, 32, 33, 34 (prostate cancer cell ablation evaluation) and FIGS. 35, 36, 37, 38, 39, 40, 41, 42, 43, 44, 45, 46 (thyroid cancer cell ablation evaluation) contain images and data related to cell death.

Fluorescent Imaging

Application of the detection of the labeled-bionanofluid will be determined by using 710 nm excitation and emission at 780 nm (IVIS requires a 50 nm band-gap between filter peak wavelengths). The uptake in the tumor, as well as different organs such as heart, liver, lung, kidneys, spleen, stomach, small intestines, bone muscle, brain and also blood, urine, and feces will be measured. FIG. 49 highlights an initial proof-of-principle distribution experiment of IRDye-800CW-labeled Hybrid-bionanofluid injected into the tail vain of a control animal and monitored using an IVIS Infrared imager over a 60 minute period. These results indicate that the distribution of the labeled nanoparticles can be visualized in various organs including the liver, kidney and bladder prior to excretion.

Magnetized Particle Cell Capturing

FIGS. 7, 8, 9 relate to Magnetic Cell Capture. Cells were mixed with antibody-conjugated magnetic bionanofluid. By specific attachment to cell surface ligands, cells are associated to the magnetic bionanofluid. Application of a magnet isolates the magnetized carbon nanotubes from the solution. Cells were also subject to the photothermal effect and cell killing resulted.

Disinfecting Application

In another embodiment, carbon derived bionanofluids have also been incorporated in hydrogels and silica foams. The applications are for topic disinfection using photothermal heating, where the foam or gel are applied topically to skin or to surface to be sterilized and the laser applied to destroy pathogens. FIG. 4 shows a streak of DH5alpha bacteria, streaked on a LB-agar plate. The bionanofluid hydrogel was added to a region, exposed to the laser. The plate was reincubated at 37° C. overnight. However, the bacteria could not regrow in the area of the hydrogel bionanofluid, thus resulting in a killing/sterilization of the area.

Numerous modifications could be made to the embodiments above without departing from the scope of the invention. The scope of the claims should not be limited by the preferred embodiments set forth in the Examples, but should be given the broadest interpretation consistent with the description as a whole.

The content of all the references cited in the present patent application is herein incorporated by reference.

The invention claimed is:

1. A method of creating disruption of a targeted entity, the targeted entity being a prokaryote or eukaryote, the method comprising:
providing a bionanofluid comprising multiple walled carbon nanotubes (MWCNTs) mono-dispersed in a polar fluid, the MWCNTS having outer surfaces and being modified on the outer surface with polar groups selected from the group consisting of carboxylic acid, amino and thiol, and functionalized with a targeting moiety attached through a spacer to the MWCNTs;
contacting the targeted entity with the bionanofluid to allow extracellular targeting of the targeted entity with the targeting moiety; and
applying an external energy selected from the group consisting of light, ultrasound or radiowaves to the bionanofluid in contact with the targeted entity;
wherein:
the MWCNTs have a length size above 1 micron and not greater than 2 microns;
the spacer comprises polyethylene glycol (PEG) of a molecular weight of from 5,000 g/mol to 100,000 g/mol; and
the targeting moiety comprises a protein, peptide, nucleic acid, oligonucleotide, biocompatible ligand or a drug molecule.

2. The method of claim 1, wherein the prokaryote or eukaryote is a cell, virus, bacteria, spore, fungus or small multi-cellular organism.

3. The method of claim 1, wherein the targeting moiety comprises an antibody, recombinant and purified thyrotropin (TSH), doxorubicin, α-snRNP or glycoside.

4. The method of claim 1, wherein the targeting moiety comprises α-TSHR or α-PSMA.

5. The method of claim 1, wherein the spacer comprises PEG-maleimide, amino-PEG-maleimide or thiol-PEG.

6. The method of claim 1, wherein the polar fluid comprises a non O—H or N—H containing solvent with a dielectric constant between 5-20 and highly polar bonds; a non O—H or N—H containing solvent with a dielectric constant over 20 and highly polar bonds; or a polar solvent possessing O—H and N—H bonds; or a combination thereof.

7. The method of claim 1, wherein the polar fluid comprises dichloromethane, tetrahydrofuran, ethyl acetate, acetone, N,N-dimethylformamide, acetonitrile, dimethyl sulfoxide, ammonia, butanol, propanol, ethanol, methanol, acetic acid or water; or a combination thereof.

8. The method of claim 1, wherein the polar fluid comprises water.

9. The method of claim 1, wherein the bionanofluid is a hybrid bionanofluid in which the carbon-based nanomaterial is further modified with hybrid nanoparticles which comprise an alloy, transition metal, semi-conductor, semi-metal, polymer-based nanoparticle or a combination thereof.

10. The method of claim 9, wherein the hybrid nanoparticle comprises iron (Fe), nickel (Ni), manganese (Mn), silver (Ag), gold (Au), silica, titanium oxide, or a combination thereof.

11. The method of claim 9, wherein the hybrid nanoparticle comprises gold (Au), iron (Fe), nickel (Ni) and/or manganese (Mn).

12. The method of claim 9, wherein the targeting moiety comprises an antibody, recombinant and purified thyrotropin (TSH), doxorubicin, α-snRNP or glycoside.

13. The method of claim 9, wherein the spacer comprises PEG-maleimide, amino-PEG-maleimide or thiol-PEG.

14. The method of claim 9, wherein the polar fluid comprises dichloromethane, tetrahydrofuran, ethyl acetate, acetone, N,N-dimethylformamide, acetonitrile, dimethyl sulfoxide, ammonia, butanol, propanol, ethanol, methanol, acetic acid or water; or a combination thereof.

15. The method of claim 1, wherein the bionanofluid is in the form of a hydrogel, a foam, a cream or a spray, wherein the hydrogel further comprises gelatin and the foam further comprises silica.

16. The method of claim 1, wherein the external energy is light comprising a light source of sufficient power to induce the photothermal conversion of light to heat, to create disruption of the prokaryote or eukaryote.

17. The method of claim 16, wherein the light is laser light.

18. The method of claim 1, wherein the targeted entity is a tumour cell or cancerous cell and the external energy is a light source of sufficient power to induce the photothermal conversion of light to heat, to create disruption of the cell membrane and cell death.

* * * * *